(12) United States Patent
Scola et al.

(10) Patent No.: US 7,132,504 B2
(45) Date of Patent: Nov. 7, 2006

(54) HEPATITIS C VIRUS INHIBITORS

(75) Inventors: Paul Michael Scola, Glastonbury, CT (US); Fiona McPhee, Wallingford, CT (US); Nicholas A Meanwell, East Hampton, CT (US); Piyasena Hewawasam, Middletown, CT (US); Jeffrey Allen Campbell, Glen Gardner, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/985,106

(22) Filed: Nov. 10, 2004

(65) Prior Publication Data

US 2005/0187165 A1 Aug. 25, 2005

Related U.S. Application Data

(60) Provisional application No. 60/519,124, filed on Nov. 12, 2003.

(51) Int. Cl.
A61K 38/00 (2006.01)
(52) U.S. Cl. .................................................. 530/18
(58) Field of Classification Search ................. 530/331
See application file for complete search history.

(56) References Cited

U.S. PATENT DOCUMENTS

| | | | |
|---|---|---|---|
| 5,633,388 | A | 5/1997 | Diana et al. |
| 5,866,684 | A | 2/1999 | Attwood et al. |
| 5,869,253 | A | 2/1999 | Draper et al. |
| 6,018,020 | A | 1/2000 | Attwood et al. |
| 6,225,284 | B1 | 5/2001 | Albert et al. |
| 6,265,380 | B1 | 7/2001 | Tung et al. |
| 6,268,207 | B1 | 7/2001 | Bailey et al. |
| 6,323,180 | B1 | 11/2001 | Llinas-Brunet et al. |
| 6,410,531 | B1 | 6/2002 | Llinas-Brunet et al. |
| 6,420,380 | B1 | 7/2002 | Llinas-Brunet et al. |
| 6,534,523 | B1 | 3/2003 | Llinas-Brunet et al. |
| 6,642,204 | B1 | 11/2003 | Llinas-Brunet et al. |
| 6,869,964 | B1 | 3/2005 | Campbell et al. |
| 6,872,805 | B1 | 3/2005 | Campbell et al. |
| 6,878,722 | B1 | 4/2005 | Campbell et al. |
| 6,919,423 | B1 * | 7/2005 | Llinas-Brunet ............... 514/18 |
| 2002/0111313 | A1 | 8/2002 | Campbell et al. |
| 2004/0048802 | A1 | 3/2004 | Ripka et al. |
| 2004/0077551 | A1 | 4/2004 | Campbell et al. |
| 2005/0020503 | A1 * | 1/2005 | Llinas-Brunet et al. ........ 514/18 |

FOREIGN PATENT DOCUMENTS

| | | |
|---|---|---|
| EP | 1162196 A1 | 12/2000 |
| WO | WO 95/33764 | 12/1995 |
| WO | WO 97/06804 | 2/1997 |
| WO | WO 97/43310 | 11/1997 |
| WO | WO 98/17679 | 4/1998 |
| WO | WO 98/22496 | 5/1998 |
| WO | WO 98/46597 | 10/1998 |
| WO | WO 98/46630 | 10/1998 |
| WO | WO 99/07733 | 2/1999 |
| WO | WO 99/07734 | 2/1999 |
| WO | WO 99/38888 | 8/1999 |
| WO | WO 99/50230 | 10/1999 |
| WO | WO 99/64442 | 12/1999 |
| WO | WO 00/06529 | 2/2000 |
| WO | WO 00/09543 | 2/2000 |
| WO | WO 00/09558 | 2/2000 |
| WO | WO 00/10573 | 3/2000 |
| WO | WO 00/13708 | 3/2000 |
| WO | WO 00/18231 | 4/2000 |
| WO | WO 00/59929 | 10/2000 |
| WO | WO 01/32153 A2 | 5/2001 |
| WO | WO 01/85172 A1 | 11/2001 |
| WO | WO 02/04425 A2 | 1/2002 |
| WO | WO 02/06246 A1 | 1/2002 |
| WO | WO 02/060926 A2 | 8/2002 |
| WO | WO 03/064416 A1 | 8/2003 |
| WO | WO 03/064455 A2 | 8/2003 |
| WO | WO 03/064456 A1 | 8/2003 |
| WO | WO 03/066103 A1 | 8/2003 |
| WO | WO 03/099274 | 12/2003 |
| WO | WO 03/099316 | 12/2003 |
| WO | WO 2004/032827 | 4/2004 |
| WO | WO 2004/043339 | 5/2004 |
| WO | WO 2005/046712 | 5/2005 |

OTHER PUBLICATIONS

U.S. Appl. No. 10/992,566, filed Nov. 18, 2004, Tu et al.

(Continued)

*Primary Examiner*—Bruce R. Campell
*Assistant Examiner*—Thomas S. Heard
(74) *Attorney, Agent, or Firm*—Pamela A. Mingo; Warren K. Volles

(57) ABSTRACT

Compounds are disclosed having the general formula:

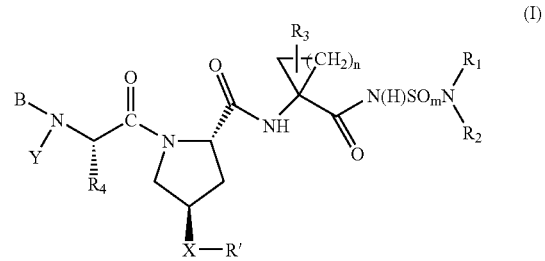

wherein $R_1$, $R_2$, $R_3$, $R_4$, R', B, Y and X are described in the description. Compositions comprising the compounds and methods for using the compounds to inhibit HCV are also disclosed.

51 Claims, No Drawings

OTHER PUBLICATIONS

U.S. Appl. No. 10/992,548, filed Nov. 18, 2004, Scola et al.

Lauer, G. M. et al., "Hepatitis C Virus Infection," The New England Journal of Medicine, vol. 345, No. 1, pp. 41-52 (2001).

Zeuzem, S. et al., "Peginterferon Alfa-2a In Patients with Chronic Hepatitis C," The New England Journal of Medicine, vol. 343, No. 23, pp. 1666-1672 (2000).

Poynard, T. et al., "Randomised trial of interferon α2b plus ribavirin for 48 weeks or for 24 weeks versus interferon α2b plus placebo for 48 weeks for treatment of chronic infection with hepatitis C virus," The Lancet, vol. 352, pp. 1426-1432 (1998).

Poupart et al., "Solid-Phase Synthesis of Peptidomimetic Inhibitors for the Hepatitis C Virus NS3 Protease," The Journal of Organic Chemistry, vol. 66, No. 14, pp. 4743-4751 (2001).

Steinkuhler et al., "Product Inhibition of the Hepatitis C Virus NS3 Protease," Biochemistry, vol. 37, pp. 8899-8905 (1998).

Ingallinella et al., "Potent Peptide Inhibitors of Human Hepatitis C Virus NS3 Protease Are Obtained by Optimizing the Cleavage Products," Biochemistry, vol. 37, pp. 8906-8914 (1998).

Chu et al., "Structure of Sch 68631: A New Hepatitis C Virus Proteinase Inhibitor from Streptomyces sp.," Tetrahedron Letters, vol. 37, No. 40, pp. 7229-7232 (1996).

Matsumoto et al., "3D Modeling of HCV Protease and Computer Screening of its Inhibitors," Antiviral Research, vol. 30, No. 1, pp. A23, Abstract 19 (1996).

* cited by examiner

HEPATITIS C VIRUS INHIBITORS

CROSS REFERENCE TO RELATED APPLICATION

The non-provisional application claims priority from the provisional application U.S. Ser. No. 60/519,124 filed Nov. 12, 2003.

FIELD OF THE INVENTION

The present invention is generally directed to antiviral compounds, and more specifically directed to compounds which inhibit the functioning of the NS3 protease (also referred to herein as "serine protease") encoded by Hepatitis C virus (HCV), compositions comprising such compounds and methods for inhibiting the functioning of the NS3 protease.

BACKGROUND OF THE INVENTION

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma. (Lauer, G. M.; Walker, B. D. N. Engl. J. Med. (2001), 345, 41–52).

Presently, the most effective HCV therapy employs a combination of alpha-interferon and ribavirin, leading to sustained efficacy in 40% of patients. (Poynard, T. et al. Lancet (1998), 352, 1426–1432). Recent clinical results demonstrate that pegylated alpha-interferon is superior to unmodified alpha-interferon as monotherapy (Zeuzem, S. et al. N. Engl. J. Med. (2000), 343, 1666–1672). However, even with experimental therapeutic regimens involving combinations of pegylated alpha-interferon and ribavirin, a substantial fraction of patients do not have a sustained reduction in viral load. Thus, there is a clear and long-felt need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to cleave at the NS2–NS3 junction; the second one is a serine protease contained within the N-terminal region of NS3 and mediates all the subsequent cleavages downstream of NS3, both in cis, at the NS3–NS4A cleavage site, and in trans, for the remaining NS4A–NS4B, NS4B–NS5A, NS5A–NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

Among the compounds that have demonstrated efficacy in inhibiting HCV replication, as selective HCV serine protease inhibitors, are the peptide compounds disclosed in U.S. Pat. No. 6,323,180.

SUMMARY OF THE INVENTION

The present invention relates to compounds having the formula

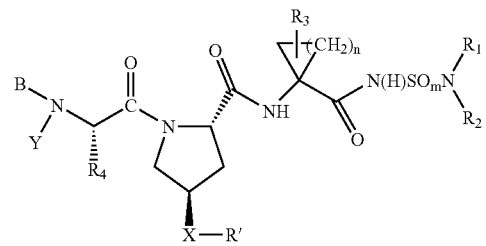

(a) $R_1$ and $R_2$ are each independently $C_{1-8}$ alkyl, $C_{3-7}$ cycloalkyl, $C_{4-10}$ alkylcycloalkyl, $C_{1-6}$ alkoxy, $C_{6-10}$ aryl, $C_{7-14}$ alkylaryl, $C_{9-14}$ cycloalkylaryl, $C_{7-14}$ alkoxyaryl, $C_{9-14}$ cycloalkoxyaryl, 5–7 membered heteroaryl or $C_{7-14}$ alkylheteroaryl; or $R_1$ and $R_2$, together with the nitrogen atom to which they are attached, join to form a 4–8 membered monocyclic heterocycle;

(b) m is 1 or 2;

(c) n is 1 or 2;

(d) $R_3$ is H or $C_{1-6}$ alkyl, $C_{2-6}$ alkenyl or $C_{3-7}$ cycloalkyl, each optionally substituted with halogen;

(e) $R_4$ is $C_{1-8}$ alkyl optionally substituted with halo, cyano, amino, $C_{1-6}$ dialkylamino, $C_{6-10}$ aryl, $C_{7-14}$ alkylaryl, $C_{1-6}$ alkoxy, carboxy, hydroxy, aryloxy, $C_{7-14}$ alkylaryloxy, $C_{2-6}$ alkylester or $C_{8-15}$ alkylarylester; $C_{3-12}$ alkenyl; $C_{3-7}$ cycloalkyl or $C_{4-10}$ alkylcycloalkyl, wherein the cycloalkyl or alkylcycloalkyl are optionally substituted with hydroxy, $C_{1-6}$ alkyl, $C_{2-6}$ alkenyl or $C_{1-6}$ alkoxy; or $R_3$ together with the carbon atom to which it is attached forms a $C_{3-7}$ cycloalkyl group optionally substituted with $C_{2-6}$ alkenyl;

(f) Y is H, phenyl substituted with nitro, pyridyl substituted with nitro, or $C_{1-6}$ alkyl optionally substituted with cyano, hydroxyl or $C_{3-7}$ cycloalkyl; provided that if $R_5$ or $R_6$ is H then Y is H;

(g) B is H, $C_{1-6}$ alkyl, $R_5$—(C=O)—, $R_5O(C=O)$—, $R_5$—N($R_6$)—C(=O)—, $R_5$—N($R_6$)—C(=S)—, $R_5SO_2$—, or $R_5$—N($R_6$)—$SO_2$—;

(h) $R_5$ is (i) $C_{1-10}$ alkyl optionally substituted with phenyl, carboxyl, $C_{1-6}$ alkanoyl, 1–3 halogen, hydroxy, —OC(O)$C_{1-6}$ alkyl, $C_{1-6}$ alkoxy, amino optionally substituted with $C_{1-6}$ alkyl, amido, or (lower alkyl)amido; (ii) $C_{3-7}$ cycloalkyl, $C_{3-7}$ cycloalkoxy, or $C_{4-10}$ alkylcycloalklyl, each optionally substituted with hydroxy, carboxyl, ($C_{1-6}$ alkoxy)carbonyl, amino optionally substituted with $C_{1-6}$ alkyl, amido, or (lower alkyl)amido; (iii) $C_{6-10}$ aryl or $C_{7-16}$ arylalkyl, each optionally substituted with $C_{1-6}$ alkyl, halogen, nitro, hydroxy, amido, (lower alkyl)amido, or amino optionally substituted with $C_{1-6}$ alkyl; (iv) Het; (v) bicyclo(1.1.1)pentane; or (vi) —C(O)OC$_{1-6}$ alkyl, $C_{2-6}$ alkenyl or $C_{2-6}$ alkynyl;

(i) $R_6$ is H; $C_{1-6}$ alkyl optionally substituted with 1–3 halogens; or $C_{1-6}$ alkoxy provided $R_5$ is $C_{1-10}$ alkyl;

(j) X is O, S, SO, SO$_2$, OCH$_2$, CH$_2$O or NH;

(k) R' is Het, $C_{6-10}$ aryl or $C_{7-14}$ alkylaryl, each optionally substituted with $R^a$; and (l) $R^a$ is $C_{1-6}$ alkyl, $C_{3-7}$ cycloalkyl, $C_{1-6}$ alkoxy, $C_{3-7}$ cycloalkoxy, halo-$C_{1-6}$ alkyl, CF$_3$, mono- or di-halo-$C_{1-6}$ alkoxy, cyano, halo, thioalkyl, hydroxy, alkanoyl, NO$_2$, SH, amino, $C_{1-6}$ alkylamino, di($C_{1-6}$) alkylamino, di($C_{1-6}$)alkylamide, carboxyl, ($C_{1-6}$)carboxyester, $C_{1-6}$ alkylsulfone, $C_{1-6}$ alkylsulfonamide, di($C_{1-6}$)alkyl (alkoxy)amine, $C_{6-10}$ aryl, $C_{7-14}$ alkylaryl, or a 5–7 membered monocyclic heterocycle;

or a pharmaceutically acceptable salt, solvate or prodrug thereof.

The present invention also provides compositions comprising the compounds or pharmaceutically acceptable salts, solvates or prodrugs thereof and a pharmaceutically acceptable carrier. In particular, the present invention provides pharmaceutical compositions useful for inhibiting HCV NS3 comprising a therapeutically effective amount of a compound of the present invention, or a pharmaceutically acceptable salt, solvate or prodrug thereof, and a pharmaceutically acceptable carrier.

The present invention further provides methods for treating patients infected with HCV, comprising administering to the patient a therapeutically effective amount of a compound of the present invention, or a pharmaceutically acceptable salt, solvate or prodrug thereof. Additionally, the present invention provides methods of inhibiting HCV NS3 protease by contacting the NS3 protease with a compound of the present invention.

By virute of the present invention, it is now possible to provide improved drugs comprising the compounds of the invention which can be effective in the treatment of patients infected with HCV. Specifically, the present invention provides peptide compounds that can inhibit the functioning of the NS3 protease, e.g., in combination with the NS4A protease. Further, the present invention makes it possible to administer combination therapy to a patient whereby a compound in accordance with the present invention, which is effective to inhibit the HCV NS3 protease, can be administered with another compound having anti-HCV activity, e.g., a compound which is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH and a nucleoside analog for the treatment of an HCV infection.

DETAILED DESCRIPTION OF THE INVENTION

Stereochemical definitions and conventions used herein generally follow McGraw-Hill Dictionary of Chemical Terms, S. P. Parker, Ed., McGraw-Hill Book Company, New York (1984) and Stereochemistry of Organic Compounds, Eliel, E. and Wilen, S., John Wiley & Sons, Inc., New York (1994). Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory and (+) or d, meaning the compound, is dextrorotatory. For a given chemical structure, these compounds, called stereoisomers, are identical except that they are mirror images of one another. A specific stereoisomer of a mirror image pair may also be referred to as an enantiomer, and a mixture of such isomers is often called an enantiomeric mixture. With reference to the instances where (R) or (S) is used, it is to designate the absolute configuration of a substituent in context to the whole compound and not in context to the substituent alone.

Unless otherwise specifically noted herein, the terms set forth below will have the following definitions.

The terms "racemic mixture" and "racemate" refer to an equimolar mixture of two enantiomeric species, devoid of optical activity.

The term "chiral" refers to molecules which have the property of non-superimposability of the mirror image partner, while the term "achiral" refers to molecules which are superimposable on their mirror image partner.

The term "stereoisomers" refers to compounds which have identical chemical composition, but differ with regard to the arrangement of the atoms or groups in space.

The term "diastereomer" refers to a stereoisomer which is not an enantiomer, e.g., a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

The term "enantiomers" refers to two stereoisomers of a compound which are non-superimposable mirror images of one another.

The term "pharmaceutically acceptable salt" is intended to include nontoxic salts synthesized from a compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p. 1445. The compounds of the present invention are useful in the form of the free base or acid or in the form of a pharmaceutically acceptable salt thereof. All forms are within the scope of the invention.

The term "therapeutically effective amount" means the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "compounds of the invention", and equivalent expressions, are meant to embrace compounds of formula I, and pharmaceutically acceptable enantiomer, diastereomer salts, and solvates, e.g. hydrates, and prodrugs. Similarly, references to intermediates, are meant to embrace their salts, and solvates, where the context so permits. References to the compound of the invention also include the preferred compounds, e.g. formula II and A-M.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates and the like.

The term "prodrug" as used herein means derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner with a functional group of the compounds such as with an amino, hydroxy or carboxy group when present. The prodrug derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine.

The term "patient" includes both human and other mammals.

The term "pharmaceutical composition" means a composition comprising a compound of the invention in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable riskibenefit ratio.

The term "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and (iii) relieving the disease, disorder or condition, i.e., causing regression of the disease, disorder and/or condition.

The term "substituted" as used herein includes substitution at from one to the maximum number of possible binding sites on the core, e.p., organic radical, to which the subsitutent is bonded, e.g., mono-, di-, tri- or tetra-substituted, unless otherwise specifically stated.

The nomenclature used to describe organic radicals, e.g., hydrocarbons and substituted hydrocarbons, generally follows standard nomenclature known in the art, unless otherwise specifically defined. Combinations of groups, e.g., alkylalkoxyamine or arylalkyl, include all possible stable configurations, unless otherwise specifically stated. Certain radicals and combinations are defined below for purposes of illustration.

The term "halo" as used herein means a halogen substituent selected from bromo, chloro, fluoro or iodo. The term "haloalkyl" means an alkyl group that in substituted with one or more halo substituents.

The term "alkyl" as used herein means acyclic, straight or branched chain alkyl substituents having the specified number of carbon atoms and includes, for example, methyl, ethyl, propyl, butyl, tert-butyl, hexyl, 1-methylethyl, 1-methylpropyl, 2-methypropyl, 1,1-dimethylethyl. Thus, $C_{1-6}$ alkyl refers to an alkyl group having from one to six carbon atoms. The term "lower alkyl" means an alkyl group having from one to six, preferably from one to four carbon atoms. The term "alkylester" means an alkyl group additionally containing on ester group. Generally, a stated carbon number range, e.g., $C_{2-6}$ alkylester, includes all of the carbon atoms in the radical.

The term "alkenyl" as used herein means an alkyl radical containing at least one double bond, e.g., ethenyl(vinyl) and alkyl.

The term "alkoxy" as used herein means an alkyl group with the indicated number of carbon atoms attached to an oxygen atom. Alkoxy includes, for example, methoxy, ethoxy, propoxy, 1-methylethoxy, butoxy and 1,1-dimethylethoxy. The latter radical is referred to in the art as tert-butoxy. The term "alkoxycarbonyl" means an alkoxy group additionally containing a carbonyl group.

The term "cycloalkyl" as used herein means a cycloalkyl substituent containing the indicated number of carbon atoms and includes, for example, cyclopropyl, cyclobutyl, cyclopentyl, cyclohexyl, cycloheptyl and spiro cyclic groups such as spirocyclopropyl as spirocyclobutyl. The term "cycloalkoxy" as used herein means a cycloalkyl group linked to an oxygen atom, such as, for example, cyclobutyloxy or cyclopropyloxy. The term "alkylcycloalkyl" means a cycloalkyl group linked to an alkyl group. The stated carbon number range includes the total number of carbons in the radical, unless otherwise specfically stated. This a $C_{4-10}$ alkylcycloalkyl may contain from 1–7 carbon atoms in the alkyl group and from 3–9 carbon atoms in the ring, e.g., cyclopropylmethyl or cyclohexylethyl.

The term "aryl" as used herein means an aromatic moiety containing the indicated number of carbon atoms, such as, but not limited to phenyl, indanyl or naphthyl. For example, $C_{6-10}$ aryl refers to an aromatic moiety having from six to ten carbon atoms which may be in the form of a monocyclic or bicyclic structure. The term "haloaryl" as used herein refers to an aryl mono, di or tri substituted with one or more halogen atoms. The terms "alkylaryl", "arylalkyl" and "aralkyl" mean an aryl group substituted with one or more alkyl groups. Unless the carbon range of each group is specified, the stated range applies to the entire substituent.

Thus, a $C_{7-14}$ alkylaryl group many have from 1–8 carbon atoms in the alkyl group for a monocyclic aromatic and from 1–4 carbon atoms in the alkyl group for a fused aromatic. The attachment of the group to bonding site on the molecule can be either at the aryl group or the alkyl group. Unless a specific aryl radical is specified, e.g., fluoro-phenyl, or the radical is stated to be unsubstituted, the aryl radicals include those substituted with typical substituents known to those skilled in the art, e.g., halogen, hydroxy, carboxy, carbonyl, nitro, sulfo, amino, cyano, dialkylamino haloalkyl, $CF_3$, haloalkoxy, thioalkyl, alkanoyl, SH, alkylamino, alkylamide, dialkylamide, carboxyester, alkylsulfone, alkylsulfonamide and alkyl(alkoxy)amine. Examples of alkylaryl groups include benzyl, butylphenyl and 1-naphthylmethyl.

The term "alkanoyl" as used herein means straight or branched 1-oxoalkyl radicals containing the indicated number of carbon atoms and includes, for example, formyl, acetyl, 1-oxopropyl(propionyl), 2-methyl-1-oxopropyl, 1-oxohexyl and the like.

The term "alkylamide" as used herein means an amide mono-substituted with an alkyl, such as

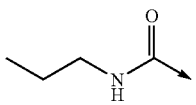

The term "heterocycle", also referred to as "Het", as used herein means 7–12 membered bicyclic heterocycles and 5–7 membered monocyclic heterocycles.

Preferred bicyclic heterocycles are 7–12 membered fused bicyclic ring systems (both rings share an adjacent pair of atoms) containing from one to four heteroatoms selected from nitrogen, oxygen and sulfur, wherein both rings of the heterocycle are fully unsaturated. The nitrogen and sulfur heteroatoms atoms may be optionally oxidized. The bicyclic heterocycle may contain the heteroatoms in one or both rings. Unless a specific heterocycle is specified, e.g., a fluorinated 7–12 membered bicyclic heterocycle, or the heterocycle is stated to be unsubstituted, the heterocycles include those substituted with typical substituents known to those skilled in the art. For example, the bicyclic heterocycle may also contain substituents on any of the ring carbon atoms, e.g., one to three substituents. Examples of suitable substituents include $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono- or di-halo-$C_{1-6}$ alkoxy, cyano, halo, thioalkyl, hydroxy, alkanoyl, $NO_2$, SH, amino, $C_{1-6}$ alkylamino, di($C_{1-6}$)alkylamino, di($C_{1-6}$)alkylamide, carboxyl, ($C_{1-6}$)carboxyester, $C_{1-6}$ alkylsulfone, $C_{1-6}$ alkylsulfonamide, $C_{1-6}$ alkylsulfoxide, di($C_{1-6}$)alkyl(alkoxy)amine, $C_{1-6}$ aryl, $C_{7-14}$ alkylaryl, and a 5–7 membered monocyclic heterocycle. When two substituents are attached to vicinal carbon atoms of the bicyclic heterocycle, they can join to form a ring, e.g., a five, six or seven membered ring system containing up to two heteroatoms selecting from oxygen and nitrogen. The bicyclic heterocycle may be attached to the molecule, e.g. $R_1$ in formula I, at any atom in the ring and preferably carbon.

Examples of bicyclic heterocycles include, but are not limited to, the following ring systems:

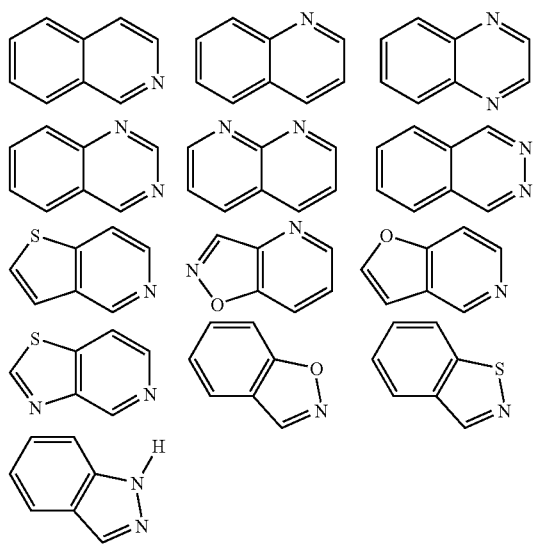

Preferred monocyclic heterocycles are 5–7 membered saturated, partially saturated or fully unsaturated ring system (this latter subset also herein referred to as unsaturated heteroaromatic) containing in the ring from one to four heteroatoms selected from nitrogen, oxygen and sulfur, wherein the sulfur and nitrogen heteroatoms may be optionally oxidized. Unless a specific heterocycle is specified, e.g., a $C_{1-6}$ alkoxy substituted 5–7 membered monocyclic heterocycle, or the heterocycle is stated to be unsubstituted, the heterocycles include those substituted with typical substituents known to those skilled in the art. For example, the monocyclic heterocycle may also contain substituents on any of the ring atoms, e.g., one to three substituents. Examples of suitable substituents include $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono- or di-halo-$C_{1-6}$ alkoxy, cyano, halo, thioalkyl, hydroxy, alkanoyl, $NO_2$, SH, , amino, $C_{1-6}$ alkylamino, di($C_{1-6}$)alkylamino, di($C_{1-6}$)alkylamide, carboxyl, ($C_{1-6}$)carboxyester, $C_{1-6}$ alkylsulfone, $C_{1-6}$ alkylsulfoxide, $C_{1-6}$ alkylsulfonamide, di($C_{1-6}$)alkyl(alkoxy)amine, $C_{6-10}$ aryl, $C_{7-14}$ alkylaryl and an additional 5–7 membered monocyclic heterocycle. The monocyclic heterocycle may be attached to the molecule, e.g. $R_1$ in formula I, at any atom in the ring.

Examples of monocyclic heterocycles include, but are not limited to, the following (and their tautomers):

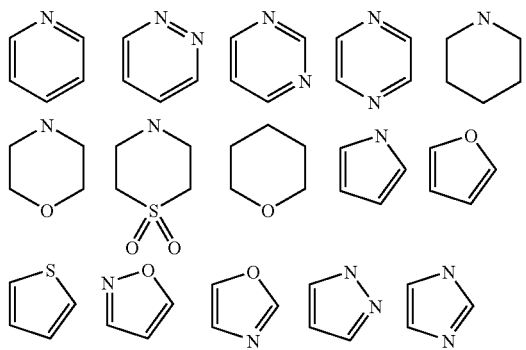

-continued

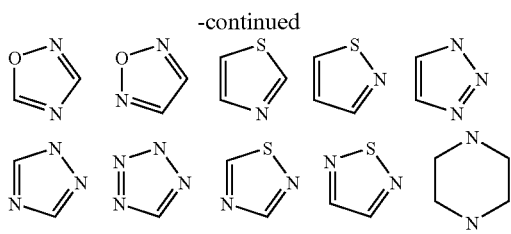

Those skilled in the art will recognize that the heterocycles used in the compounds of the present invention should be stable. Generally, stable compounds are those which can be synthesized, isolated and formulated using techniques known the those skilled in the art without degradation of the compound.

The term "substituent" with reference to an amino acid or amino acid derivative means a radical derived from the corresponding α-amino acid. For instance, the substituents methyl, iso-propyl, and phenyl represent the amino acids alanine, valine, and phenyl glycine, respectively.

Where used in naming compounds of the present invention, the designations "P1', P1, P2, P3 and P4", as used herein, map the relative positions of the amino acid residues of a protease inhibitor binding relative to the binding of the natural peptide cleavage substrate. Cleavage occurs in the natural substrate between P1 and P1' where the nonprime positions designate amino acids starting from the C-terminus end of the peptide natural cleavage site extending towards the N-terminus; whereas, the prime positions emanate from the N-terminus end of the cleavage site designation and extend towards the C-terminus. For example, P1' refers to the first position away from the right hand end of the C-terminus of the cleavage site (ie. N-terminus first position); whereas P1 starts the numbering from the left hand side of the C-terminus cleavage site, P2: second position from the C-terminus, etc.)(see Berger A. & Schechter I., Transactions of the Royal Society London series (1970), B257, 249–264].

Thus in the compounds of formula I, the "P1' to P4" portions of the molecule are indicated below:

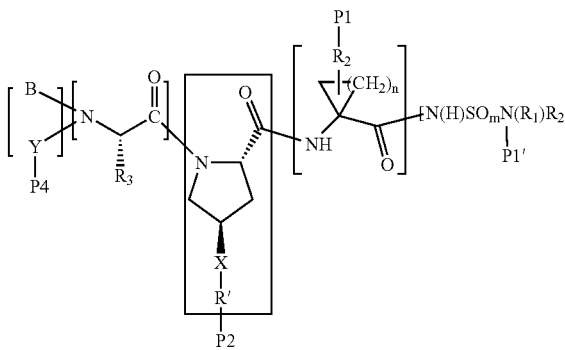

As used herein the term "1-aminocyclopropyl-carboxylic acid" (Acca) refers to a compound of formula:

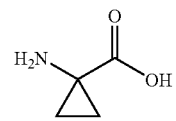

As used herein the term "tert-butylglycine" refers to a compound of the formula:

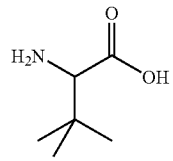

The term "residue" with reference to an amino acid or amino acid derivative means a radical derived from the corresponding α-amino acid by eliminating the hydroxyl of the carboxy group and one hydrogen of the α-amino acid group. For instance, the terms Gln, Ala, Gly, Ile, Arg, Asp, Phe, Ser, Leu, Cys, Asn, Sar and Tyr represent the "residues" of L-glutamine, L-alanine, glycine, L-isoleucine, L-arginine, L-aspartic acid, L-phenylalanine, L-serine, L-leucine, L-cysteine, L-asparagine, sarcosine and L-tyrosine, respectively.

The term "side chain" with reference to an amino acid or amino acid residue means a group attached to the α-carbon atom of the α-amino acid. For example, the R-group side chain for glycine is hydrogen, for alanine it is methyl, for valine it is isopropyl. For the specific R-groups or side chains of the α-amino acids reference is made to A. L. Lehninger's text on Biochemistry (see chapter 4).

The compounds of the present invention have the structure of Formula I:

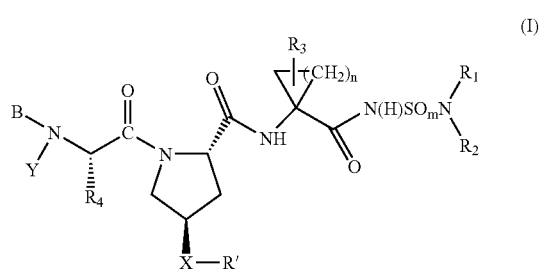

(a) $R_1$ and $R_2$ are each independently $C_{1-8}$ alkyl, $C_{3-7}$ cycloalkyl $C_{4-10}$ alkylcycloalkyl, $C_{1-6}$ alkoxy, $C_{6-10}$ aryl, $C_{7-14}$ alkylaryl, $C_{9-14}$ cycloalkylaryl, $C_{7-14}$ alkoxyaryl, $C_{9-14}$ cycloalkoxyaryl, 5–7 membered heteroaryl or $C_{7-14}$ alkylheteroaryl; or $R_1$ and $R_2$, together with the nitrogen atom to which they are attached, join to form a 4–8 membered monocyclic heterocycle;
(b) m is 1 or 2;
(c) n is 1 or 2;
(d) $R_3$ is H; or $C_{1-6}$ alkyl, $C_{2-6}$ alkenyl or $C_{3-7}$ cycloalkyl, each optionally substituted with halogen;
(e) $R_4$ is $C_{1-8}$ alkyl optionally substituted with halo, cyano, amino, $C_{1-6}$ dialkylamino, $C_{6-10}$ aryl, $C_{7-14}$ alkylaryl, $C_{1-6}$ alkoxy, carboxy, hydroxy, aryloxy, $C_{7-14}$ alkylaryloxy, $C_{2-6}$ alkylester or $C_{8-15}$ alkylarylester;

$C_{3-12}$ alkenyl; $C_{3-7}$ cycloalkyl or $C_{4-10}$ alkylcycloalkyl, wherein the cycloalkyl or alkylcycloalkyl are optionally substituted with hydroxy, $C_{1-6}$ alkyl, $C_{2-6}$ alkenyl or $C_{1-6}$ alkoxy; or $R_3$ together with the carbon atom to which it is attached forms a $C_{3-7}$ cycloalkyl group optionally substituted with $C_{2-6}$ alkenyl;

(f) Y is H, phenyl substituted with nitro, pyridyl substituted with nitro, or $C_{1-6}$ alkyl optionally substituted with cyano, hydroxyl or $C_{3-7}$ cycloalkyl; provided that if $R_5$ or $R_6$ is H then Y is H;

(g) B is H, $C_{1-6}$ alkyl, $R_5$—(C=O)—, $R_5O(C=O)$—, $R_5$—$N(R_6)$—C(=O)—, $R_5$—$N(R_6)$—C(=S)—, $R_5SO_2$—, or $R_5$—$N(R_6)$—$SO_2$—;

(h) $R_5$ is (i) $C_{1-10}$ alkyl optionally substituted with phenyl, carboxyl, $C_{1-6}$ alkanoyl, 1–3 halogen, hydroxy, —OC(O)$C_{1-6}$ alkyl, $C_{1-6}$ alkoxy, amino optionally substituted with $C_{1-6}$ alkyl, amido, or (lower alkyl)amido; (ii) $C_{3-7}$ cycloalkyl, $C_{3-7}$ cycloalkoxy, or $C_{4-10}$ alkylcycloalklyl, each optionally substituted with hydroxy, carboxyl, ($C_{1-6}$ alkoxy)carbonyl, amino optionally substituted with $C_{1-6}$ alkyl, amido, or (lower alkyl)amido; (iii) $C_{6-10}$ aryl or $C_{7-16}$ arylalkyl, each optionally substituted with $C_{1-6}$ alkyl, halogen, nitro, hydroxy, amido, (lower alkyl)amido, or amino optionally substituted with $C_{1-6}$ alkyl; (iv) Het; (v) bicyclo(1.1.1)pentane; or (vi) —C(O)O$C_{1-6}$ alkyl, $C_{2-6}$ alkenyl or $C_{2-6}$ alkynyl;

(i) $R_6$ is H; $C_{1-6}$ alkyl optionally substituted with 1–3 halogens; or $C_{1-6}$ alkoxy provided $R_5$ is $C_{1-10}$ alkyl;

(j) X is O, S, SO, $SO_2$, $OCH_2$, $CH_2O$ or NH;

(k) R' is Het, $C_{6-10}$ aryl or $C_{7-14}$ alkylaryl, each optionally substituted with $R^a$; and (l) $R^a$ is $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono- or di-halo-$C_{1-6}$ alkoxy, cyano, halo, thioalkyl, hydroxy, alkanoyl, $NO_2$, SH, , amino, $C_{1-6}$ alkylamino, di($C_{1-6}$) alkylamino, di($C_{1-6}$)alkylamide, carboxyl, ($C_{1-6}$)carboxyester, $C_{1-6}$ alkylsulfone, $C_{1-6}$ alkylsulfonamide, di($C_{1-6}$) alkyl(alkoxy)amine, $C_{6-10}$ aryl, $C_{7-14}$ alkylaryl, or a 5–7 membered monocyclic heterocycle;

or a pharmaceutically acceptable salt, solvate or prodrug thereof.

Preferably, $R_1$ and $R_2$ are each independently $C_{1-8}$ alkyl, $C_{3-7}$ cycloalkyl, $C_{4-10}$ alkylcycloalkyl, $C_{1-6}$ alkoxy, $C_{6-10}$ aryl, $C_{7-14}$ alkylaryl, 5–7 membered heteroaryl or $C_{7-14}$ alkylheteroaryl; or $R_1$ and $R_2$, together with the nitrogen atom to which they are attached, join to form a 4–8 membered monocyclic heterocycle. More preferably, $R_1$ and $R_2$ are each independently $C_{1-8}$ alkyl, $C_{4-10}$ alkylcycloalkyl, $C_{1-6}$ alkoxy, $C_{6-10}$ aryl, $C_{7-14}$ alkylaryl, 5–7 membered heteroaryl or $C_{7-14}$ alkylheteroaryl, or $R_1$ and $R_2$, together with the nitrogen atom to which they are attached, join to form a 5–6 membered monocyclic heterocycle.

Preferably, $R_3$ is $C_{1-6}$ alkyl, $C_{2-6}$ alkenyl or $C_{3-7}$ cycloalkyl. More preferably, $R_3$ is $C_{2-6}$ alkenyl.

Preferably, $R_4$ is $C_{1-8}$ alkyl optionally substituted with $C_6$ aryl, $C_{1-6}$ alkoxy, carboxy, hydroxy, aryloxy, $C_{7-14}$ alkylaryloxy, $C_{2-6}$ alkylester or $C_{8-15}$ alkylarylester; $C_{3-12}$ alkenyl; $C_{3-7}$ cycloalkyl; or $C_{4-10}$ alkylcycloalkyl. More preferably, $R_4$ is $C_{1-8}$ alkyl optionally substituted with $C_{1-6}$ alkoxy; or $C_{3-7}$ cycloalkyl.

Preferably, Y is H.

Preferably, B is H, $C_{1-6}$ alkyl, $R_5$—(C=O)—, $R_5O(C=O$—, $R_5$—$N(R_6)$—C(=O)—, $R_5$—$N(R_6)$—C(=S)—, $R_5SO_2$—, or $R_5$—$N(R_6)$—$SO_2$—. More preferably, B is $R_5$—(C=O)—, $R_5O(C=O)$—, or $R_5$—$N(R_6)$—C(=O)—. Even more preferably, B is $R_5O(C=O)$— and $R_5$ is $C_{1-6}$ alkyl.

Preferably, $R_5$ is (i) $C_{1-10}$ alkyl optionally substituted with phenyl, carboxyl, $C_{1-6}$ alkanoyl, 1–3 halogen, hydroxy, $C_{1-6}$ alkoxy; (ii) $C_{3-7}$ cycloalkyl, $C_{3-7}$ cycloalkoxy, or $C_{4-10}$ alkylcycloalklyl; or (iii) $C_{6-10}$ aryl or $C_{7-16}$ arylalkyl, each optionally substituted with $C_{1-6}$ alkyl or halogen. More preferably, $R_5$ is (i) $C_{1-10}$ alkyl optionally substituted with 1–3 halogen or $C_{1-6}$ alkoxy; or (ii) $C_{3-7}$ cycloalkyl or $C_{4-10}$ alkylcycloalkyl.

Preferably, $R_6$ is H or $C_{1-6}$ alkyl optionally substituted with 1–3 halogens. More preferably, $R_6$ is H.

Preferably, X is O or NH.

Preferably, R' is Het; or $C_{6-10}$ aryl optionally substituted with $R^a$. More preferably, R' is Het. Even more preferably, the heterocycle contains 1 or 2 nitrogen atoms and optionally a sulfur atom or an oxygen atom in the ring. Preferably, the heterocycle is substituted with at least one of $C_{1-6}$ alkyl, $C_{1-6}$ alkoxy, halo, $C_{6-10}$ aryl, $C_{7-14}$ alkylaryl, or a 5–7 membered monocyclic heterocycle.

Preferably, $R^a$ is $C_{1-6}$ alkyl, $C_{3-7}$ cycloalkyl, $C_{1-6}$ alkoxy, halo-$C_{1-6}$ alkyl, halo, amino, $C_6$ aryl, or a 5–7 membered monocyclic heterocycle.

In a prefered aspect of the invention, there is provided a compound having the formula

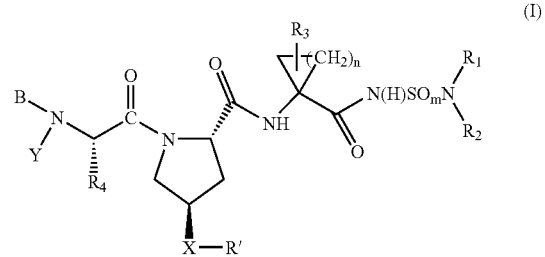

(I)

wherein
(a) $R_1$ and $R_2$ are each independently $C_{1-8}$ alkyl, $C_{3-7}$ cycloalkyl, $C_{4-10}$ alkylcycloalkyl, $C_{1-6}$ alkoxy, $C_{6-10}$ aryl, $C_{7-14}$ alkylaryl, 5–7 membered heteroaryl, $C_{7-14}$ alkylheteroaryl, or $R_1$ and $R_2$, together with the nitrogen atom to which they are attached, join to form a 4–8 membered monocyclic heterocycle;
(b) m is 1 or 2;
(c) n is 1 or 2;
(d) $R_3$ is $C_{1-6}$ alkyl, $C_{2-6}$ alkenyl or $C_{3-7}$ cycloalkyl;
(e) $R_4$ is $C_{1-8}$ alkyl optionally substituted with $C_6$ aryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl, $C_{3-7}$ cycloalkyl, or $C_{4-10}$ alkylcycloalkyl;
(f) B is H, $C_{1-6}$ alkyl, $R_5$—(C=O)—, $R_5O(C=O)$—, $R_5$—$N(R_6)$—C(=O)—, $R_5$—$N(R_6)$—C(=S)—, $R_5SO_2$—, or $R_5$—$N(R_6)$—$SO_2$—;
(g) $R_5$ is (i) $C_{1-10}$ alkyl optionally substituted with phenyl, carboxyl, $C_{1-6}$ alkanoyl, 1–3 halogen, hydroxy, $C_{1-6}$ alkoxy; (ii) $C_{3-7}$ cycloalkyl, $C_{3-7}$ cycloalkoxy, or $C_{4-10}$ alkylcycloalklyl; or (iii) $C_{6-10}$ aryl or $C_{7-16}$ arylalkyl, each optionally substituted with $C_{1-6}$ alkyl or halogen;
(h) $R_6$ is H or $C_{1-6}$ alkyl optionally substituted with 1–3 halogens;
(i) X is O or NH;
(j) R' is Het; or $C_{6-10}$ aryl optionally substituted with $R^a$; and (k) $R^a$ is $C_{1-6}$ alkyl, $C_{3-7}$ cycloalkyl, $C_{1-6}$ alkoxy, halo-$C_{1-6}$ alkyl, halo, amino, $C_6$ aryl, or a 5–7 membered monocyclic heterocycle;

or a pharmaceutically acceptable salt, solvate or prodrug thereof.

Preferably, $R_1$ and $R_2$ are each independently $C_{1-8}$ alkyl, $C_{4-10}$ alkylcycloalkyl, $C_{1-6}$ alkoxy, $C_{6-10}$ aryl, $C_{7-14}$ alkylaryl, 5–7 membered heteroaryl, $C_{7-14}$ alkylheteroaryl, or $R_1$ and $R_2$, together with the nitrogen atom to which they are attached, join to form a 5–6 membered monocyclic heterocycle More preferably, $R_1$ and $R_2$ are each independently $C_{1-3}$ alkyl or $C_{1-3}$ alkoxy.

Preferably, R' is a bicyclic heterocycle. More preferably, the heterocycle contains 1 or 2 nitrogen atoms and optionally a sulfur atom or an oxygen atom in the ring. Preferably, the heterocycle is substituted with at least one of $C_{1-6}$ alkyl, $C_{1-6}$ alkoxy, halo, $C_6$ aryl, and a 5–7 membered monocyclic heterocycle. Even more preferably, R' is a bicyclic heterocycle containing 1 nitrogen atom and substituted with methoxy and at least one of a $C_6$ aryl and a 5–7 membered monocyclic heterocycle.

In another prefered aspect, R' is a monocyclic heterocycle. Preferably, the heterocycle contains 1 or 2 nitrogen atoms and optionally a sulfur atom or an oxygen atom in the ring. More preferably, the heterocycle is substituted with at least one of $C_{1-6}$ alkyl, $C_{1-6}$ alkoxy, halo, $C_{6-10}$ aryl, $C_{7-14}$ alkylaryl, or a 5–7 membered monocyclic heterocycle. Preferably, R' is a monoyclic heterocycle containing 1 or 2 nitrogen atoms and substituted with methoxy and at least one of a $C_6$ aryl and a 5–7 membered monocyclic heterocycle.

In another prefered aspect of the invention, there is provided a compound having the formula

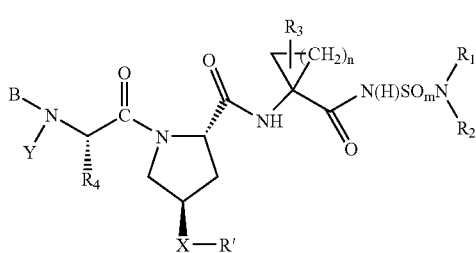

(I)

(a) $R_1$ and $R_2$ are each independently $C_{1-8}$ alkyl, $C_{4-10}$ alkylcycloalkyl, $C_{1-6}$ alkoxy, $C_{6-10}$ aryl, $C_{7-14}$ alkylaryl, 5–7 membered heteroaryl or $C_{7-14}$ alkylheteroaryl; or $R_1$ and $R_2$, together with the nitrogen atom to which they are attached, join to form a 5–6 membered monocyclic heterocycle;

(b) m is 1 or 2;
(c) n is 1 or 2;
(d) $R_3$ is $C_{2-6}$ alkenyl;
(e) $R_4$ is $C_{1-8}$ alkyl;
(f) B is $R_5O(C=O)-$, or $R_5-NH-C(=O)-$;
(g) $R_5$ is $C_{1-10}$ alkyl;
(h) R' is a bicyclic heterocycle optionally substituted with $R^a$; and
(i) $R^a$ is $C_{1-6}$ alkyl, $C_{1-6}$ alkoxy, halo, $C_6$ aryl, or a 5–7 membered monocyclic heterocycle;

or a pharmaceutically acceptable salt, solvate or prodrug thereof.

Preferably, $R_1$ and $R_2$ are each independently $C_{1-3}$ alkyl, or $C_{1-3}$ alkoxy. More preferably, $R_1$ is methyl. Preferably, $R_2$ is methyl or methoxy. Preferably, $R_3$ is vinyl. Preferably, $R_4$ is t-butyl. Preferably, $R_5$ is t-butyl. Preferably, R' is quinoline or isoquinoline optionally substituted with $R^a$.

Preferably, $R_1$ is methyl, $R_2$ is methoxy, $R_3$ is vinyl, $R_4$ is t-butyl, $R_5$ is t-butyl, and R' is isoquinoline substituted with at least one $R^a$. Preferably, $R^a$ is $C_{1-6}$ alkoxy. More preferably, $R^a$ further includes at least one of $C_6$ aryl or a 5–7 membered monocyclic heterocycle.

The compounds of the present invention, which contain a basic moiety, can form salts by the addition of a pharmaceutically acceptable acid. The acid addition salts are formed from a compound of Formula I and a pharmaceutically acceptable inorganic acid, including but not limited to hydrochloric, hydrobromic, hydroiodic, sulfuric, phosphoric, or organic acid such as p-toluenesulfonic, methanesulfonic, acetic, benzoic, citric, malonic, fumaric, maleic, oxalic, succinic, sulfamic, or tartaric. Thus, examples of such pharmaceutically acceptable salts include chloride, bromide, iodide, sulfate, phosphate, methanesulfonate, citrate, acetate, malonate, fumarate, sulfamate, and tartrate.

Salts of an amine group may also comprise quaternary ammonium salts in which the amino nitrogen carries a suitable organic group such as an alkyl, alkenyl, alkynyl or aralkyl moiety.

Compounds of the present invention, which are substituted with an acidic group, may exist as salts formed through base addition. Such base addition salts include those derived from inorganic bases which include, for example, alkali metal salts (e.g. sodium and potassium), alkaline earth metal salts (e.g. calcium and magnesium), aluminum salts and ammonium salts. In addition, suitable base addition salts include salts of physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bishydroabietylamine, glucamine, N-methylglucamine, collidine, quinine, quinoline, ethylenediamine, ornithine, choline, N,N'-benzylphenethylamine, chloroprocaine, diethanolamine, diethylamine, piperazine, tris(hydroxymethyl)aminomethane and tetramethylammonium hydroxide and basic amino acids such as lysine, arginine and N-methylglutamine. These salts may be prepared by methods known to those skilled in the art.

Certain compounds of the present invention, and their salts, may also exist in the form of solvates with water, for example hydrates, or with organic solvents such as methanol, ethanol or acetonitrile to form, respectively, a methanolate, ethanolate or acetonitrilate. The present invention includes each solvate and mixtures thereof.

In addition, compounds of the present invention, or a salt or solvate thereof, may exhibit polymorphism. The present invention also encompasses any such polymorphic form.

The compounds of the present invention also contain two or more chiral centers. For example, the compounds may include P1 cyclopropyl element of formula

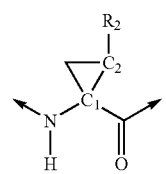

P1 wherein $C_1$ and $C_2$ each represent an asymmetric carbon atom at positions 1 and 2 of the cyclopropyl ring. Not withstanding other possible asymmetric centers at other segments of the compounds, the presence of these two asymmetric centers means that the compounds can exist as racemic mixtures of diastereomers, such as the diastereomers wherein $R_2$ is configured either syn to the amide or syn to the carbonyl as shown below.

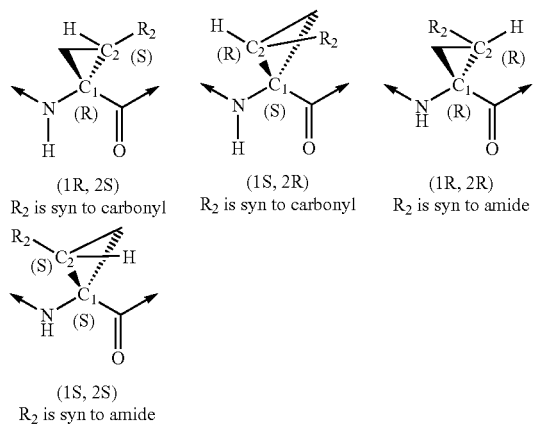

The present invention includes both enantiomers and mixtures of enantiomers such as racemic mixtures.

The enantiomers may be resolved by methods known to those skilled in the art, for example, by formation of diastereoisomeric salts which may be separated by crystallization, gas-liquid or liquid chromatography, selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

The compounds of the present invention may be in the form of a prodrug. Simple aliphatic or aromatic esters derived from, when present, acidic groups pendent on the compounds of this invention are preferred prodrugs. In some cases it is desirable to prepare double ester type prodrugs such as (acyloxy)alkyl esters or (alkoxycarbonyl)oxy)alkyl esters.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

Certain compounds of the present invention may exist in zwitterionic form and the present invention includes each zwitterionic form of these compounds and mixtures thereof.

The starting materials useful to synthesize the compounds of the present invention are known to those skilled in the art and can be readily manufactured or are commercially available.

The compounds of the present invention can be manufactured by methods known to those skilled in the art, see e.g., U.S. Pat. No. 6,323,180 and U.S. Patent Application Publication No. 20020111313 A1, published Aug. 15, 2002.

The following methods set forth below are provided for illustrative purposes and are not intended to limit the scope of the claimed invention. It will be recognized that it may be preferred or necessary to prepare such a compound in which a functional group is protected using a conventional protecting group then to remove the protecting group to provide a compound of the present invention. The details concerning the use of protecting groups in accordance with the present invention are known to those skilled in the art.

The compounds of the present invention may, for example, be synthesized according to a general process as illustrated in Scheme I (wherein CPG is a carboxyl protecting group and APG is an amino protecting group):

Scheme I

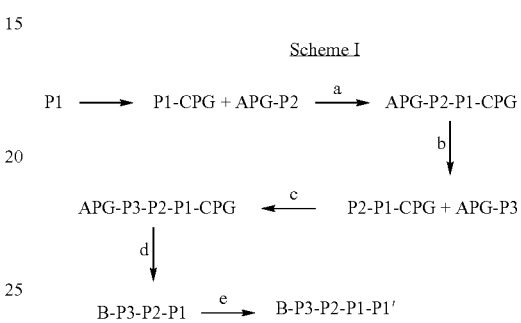

Briefly, the P1, P2, and P3 can be linked by well known peptide coupling techniques. The P1, P2, and P3 groups may be linked together in any order as long as the final compound corresponds to peptides of the invention. For example, P3 can be linked to P2-P1; or P1 linked to P3-P2.

Generally, peptides are elongated by deprotecting the α-amino group of the N-terminal residue and coupling the unprotected carboxyl group of the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme I.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (ρ-nitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole or 4-DMAP. These coupling reactions can be performed in either solution (liquid phase) or solid phase.

More explicitly, the coupling step involves the dehydrative coupling of a free carboxyl of one reactant with the free amino group of the other reactant in the present of a coupling agent to form a linking amide bond. Descriptions of such coupling agents are found in general textbooks on peptide chemistry, for example, M. Bodanszky, "Peptide Chemistry", $2^{nd}$ rev ed., Springer-Verlag, Berlin, Germany, (1993). Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A practical and useful coupling agent is the commercially available (benzotriazol- 1-yloxy)tris-(dimethylamino)phosphonium hexafluorophosphate, either by itself or in the present of 1-hydroxybenzotriazole or 4-DMAP. Another practical and useful coupling agent is commercially available 2-(1H-benzotriazol-1-yl)-N,N,N',N'-tetramethyluronium tetrafluoroborate. Still another practical and useful coupling agent is commercially available O-(7-azabenzotrizol-1-yl)-N,N,N',N'-tetramethyluronium hexafluorophosphate. The coupling reaction is conducted in an inert solvent, e.g. dichloromethane, acetonitrile or dimethylformamide. An excess of a tertiary amine, e.g. diisopropylethylamine, N-methylmorpholine, N-methylpyrrolidine or 4-DMAP is added to maintain the reaction mixture at a pH of about 8. The reaction temperature usually ranges between 0° C. and 50° C. and the reaction time usually ranges between 15 min and 24 h.

The functional groups of the constituent amino acids generally must be protected during the coupling reactions to avoid formation of undesired bonds. Protecting groups that can be used are listed, for example, in Greene, "Protective Groups in Organic Chemistry", John Wiley & Sons, New York (1981) and "The Peptides: Analysis, Synthesis, Biology", Vol. 3, Academic Press, New York (1981), the disclosures of which are hereby incorporated by reference.

The α-amino group of each amino acid to be coupled to the growing peptide chain must be protected (APG). Any protecting group known in the art can be used. Examples of such groups include: 1) acyl groups such as formyl, trifluoroacetyl, phthalyl, and ρ-toluenesulfonyl; 2) aromatic carbamate groups such as benzyloxycarbonyl (Cbz or Z) and substituted bensyloxycarbonyls, and 9-fluorenylmethyloxycarbonyl (Fmoc); 3) aliphatic carbamate groups such as tert-butyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6) trialkylsilyl such as trimethylsilyl; and 7) thiol containing groups such as phenylthiocarbonyl and dithiasuccinoyl.

The preferred α-amino protecting group is either Boc or Fmoc. Many amino acid derivatives suitably protected for peptide synthesis are commercially available. The α-amino protecting group of the newly added amino acid residue is cleaved prior to the coupling of the next amino acid. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature (rt or RT) usually 20–22° C.

Any of the amino acids having side chain functionalities must be protected during the preparation of the peptide using any of the above-described groups. Those skilled in the art will appreciate that the selection and use of appropriate protecting groups for these side chain functionalities depend upon the amino acid and presence of other protecting groups in the peptide. The selection of such protecting groups is important in that the group must not be removed during the deprotection and coupling of the α-amino group.

For example, when Boc is used as the α-amino protecting group, the following side chain protecting group are suitable: p-toluenesulfonyl (tosyl) moieties can be used to protect the amino side chain of amino acids such as Lys and Arg; acetamidomethyl, benzyl (Bn), or tert-butylsulfonyl moieties can be used to protect the sulfide containing side chain of cysteine; bencyl (Bn) ethers can be used to protect the hydroxy containing side chains of serine, threonine or hydroxyproline; and benzyl esters can be used to protect the carboxy containing side chains of aspartic acid and glutamic acid.

When Fmoc is chosen for the α-amine protection, usually tert-butyl based protecting groups are acceptable. For instance, Boc can be used for lysine and arginine, tert-butyl ether for serine, threonine and hydroxyproline, and tert-butyl ester for aspartic acid and glutamic acid. Triphenylmethyl (Trityl) moiety can be used to protect the sulfide containing side chain of cysteine.

Once the elongation of the peptide is completed all of the protecting groups are removed. When a liquid phase synthesis is used, the protecting groups are removed in whatever manner is dictated by the choice of protecting groups. These procedures are well known to those skilled in the art.

Further, the following guidance may be followed in the preparation of compounds of the present invention. For example, to form a compound where $R_4$—C(O)—, $R_4$—S(O)$_2$, a protected P3 or the whole peptide or a peptide segment is coupled to an appropriate acyl chloride or sulfonyl chloride respectively, that is either commercially available or for which the synthesis is well known in the art. In preparing a compound where $R_4$O—C(O)—, a protected P3 or the whole peptide or a peptide segment is coupled to an appropriate chloroformate that is either commercially available or for which the synthesis is well known in the art. For Boc-derivatives (Boc)$_2$O is used.

For example:

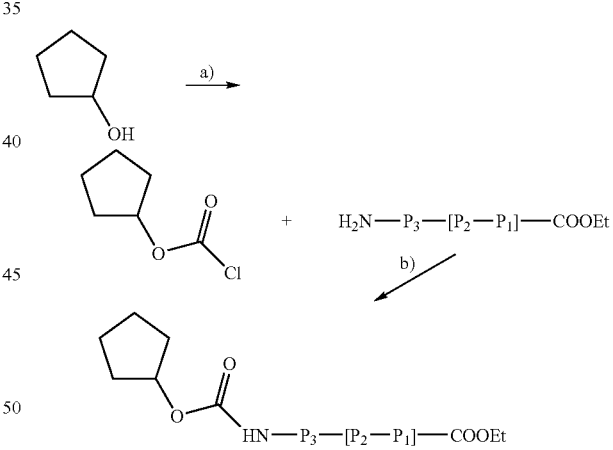

Cyclopentanol is treated with phosgene to furnish the corresponding chloroformate.

The chloroformate is treated with the desired $NH_2$-tripeptide in the presence of a base such as triethylamine to afford the cyclopentylcarbamate.

In preparing a compound where $R_4$—N($R_5$)—C(O)—, or $R_4$—NH—C(S)—, a protected P3 or the whole peptide or a peptide segment is treated with phosgene followed by amine as described in SynLett. February 1995; (2); 142–144 or is reacted with the commercially available isocyanate and a suitable base such as triethylamine.

In preparing a compound where $R_4$—N($R_5$)—S(O$_2$), a protected P3 or the whole peptide or a peptide segment is treated with either a freshly prepared or commercially available sulfamyl chloride followed by amine as described in patent Ger. Offen.(1998), 84 pp. DE 19802350 or WO 98/32748.

The α-carboxyl group of the C-terminal residue is usually protected as an ester (CPG) that can be cleaved to give the carboxylic acid. Protecting groups that can be used include: 1) alkyl esters such as methyl, trimethylsilylethyl and t-butyl, 2) aralkyl esters such as benzyl and substituted benzyl, or 3) esters that can be cleaved by mild base treatment or mild reductive means such as trichloroethyl and phenacyl esters.

The resulting α-carboxylic acid (resulting from cleavage by mild acid, mild base treatment or mild reductive means) is coupled with a $R_1(R_2)NSO_2NH_2$ [prepared by described herein] in the presence of peptide coupling agent such as CDI in the presence of a base such as LiHMDS (lithium bis-hexamethyldisilylamide) to incorporate the P1' moiety, effectively assembling the tripeptide P1'-P1-P2-P3-APG.

Scheme II further shows the general process wherein compounds of Formula I are constructed by the coupling of tripeptide carboxylic acid intermediate (1) with a P1' sulfamide. (It should be noted that the groups $R_6$, $R_7$, $R_8$, $R_9$, $R_{10}$, $R_{11}$ as shown below represent substituents of the heterocyclic system.) Said coupling reaction requires treatment of carboxylic acid (1) with a coupling reagent such as carbonyl diimidazole such as THF, which can be heated to reflux, followed by the addition of the formed derivative of (1), to the P1' sulfamide, in a solvent such as THF or methylene chloride in the presence of a base such as lithium bishexamethyldisilylamide.

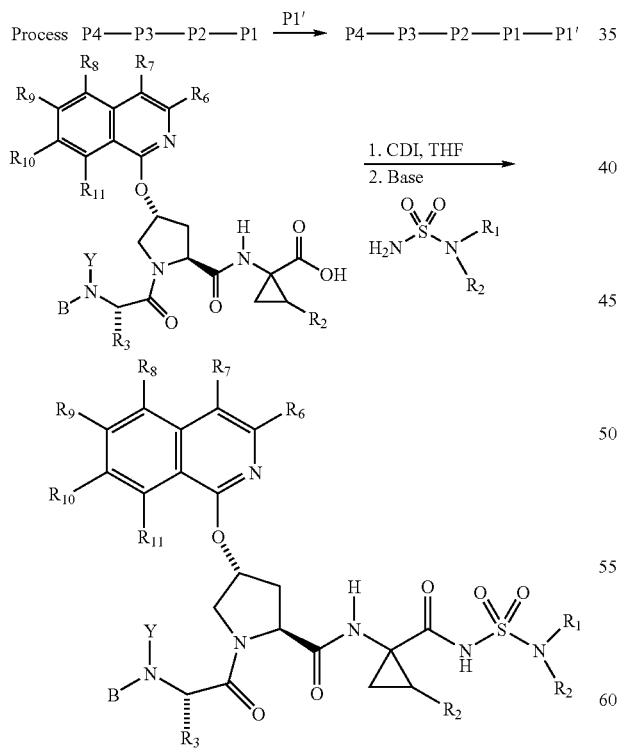

Scheme II

An alternative process for the construction of compounds of Formula I is shown in Scheme III. Therein the P1' sulfamide element is coupled to the P1 element using the process employed in Scheme II. The resulting P1-P1' moiety can then be deprotected at it's amino terminus. In this general example a Boc protecting group is employed but one skilled in the art would recognize that a number of suitable amino protecting groups could be employed in this process. Said Boc protecting group can be removed using acid such as trifluoroacetic acid in a solvent such as dichloroethane to provide the deprotected amine as the TFA salt. Said TFA amine salt can be directly employed in the subsequent coupling reaction or as an alternative the TFA amine salt can be first converted to the HCl amine salt, and this HCl amine salt is used in said coupling reaction as shown in Scheme III. The coupling of said HCl amine salt (3) with the carboxyl terminus a P4-P3-P2 intermediate can be achieved using coupling reagents, such as HATU, in solvents such as dichloromethane to provide compounds of Formula I (4).

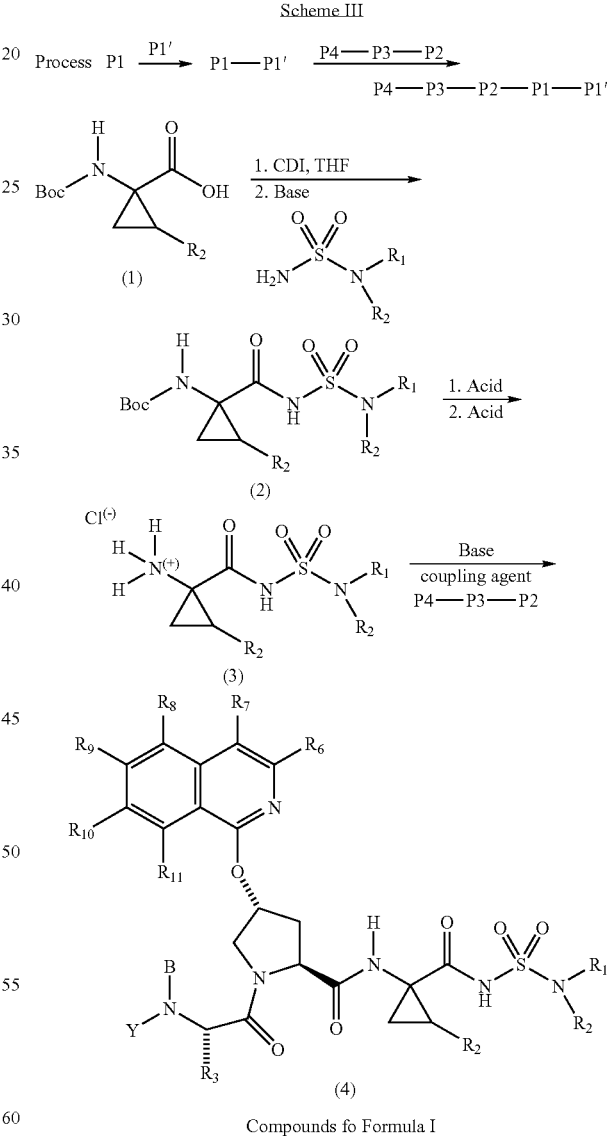

Compounds fo Formula I

An alternative process for the construction of compounds of Formula I is shown in Scheme IV. Herein the hydrochloride salt of the P1-P1' terminal amine (1) is coupled to the free carboxyl group of the P2 element using coupling agents such as PyBOP, in the presence of a base such as diisopropyl amine, and in a solvent such as methylene chloride. The resulting P2-P1-P1' intermediate can be converted to compounds of Formula I in a two step process wherein the first step is deprotection of the P2 amine terminus using an acid such as TFA in a solvent such as methylene chloride. The resulting trifluoroacetic acid salt can be coupled with the carboxyl terminus of the P4-P3 element using standard coupling agents such as PyBop in the presence of base such as diisopropyl amine, and using solvents such methylene chloride to provide compounds of Formula I (4).

The P4-P3-P2 intermediate utilized in the above schemes can be constructed as previously described with a further description of this process shown in general Scheme V. Therein the free carboxyl terminus of the P4-P3 intermediate (1), can be coupled to the amino terminus of the P2 element to provide the P4-P3-P2 dipeptide (2). The carboxyl terminus of the P4-P3-P2 intermediate can be deprotected by saponification of the ester group to provide P4-P3-P2 as the free carboxylic acid (3). Intermediates like (3) can be converted to compounds of Formula I using the methods described herein.

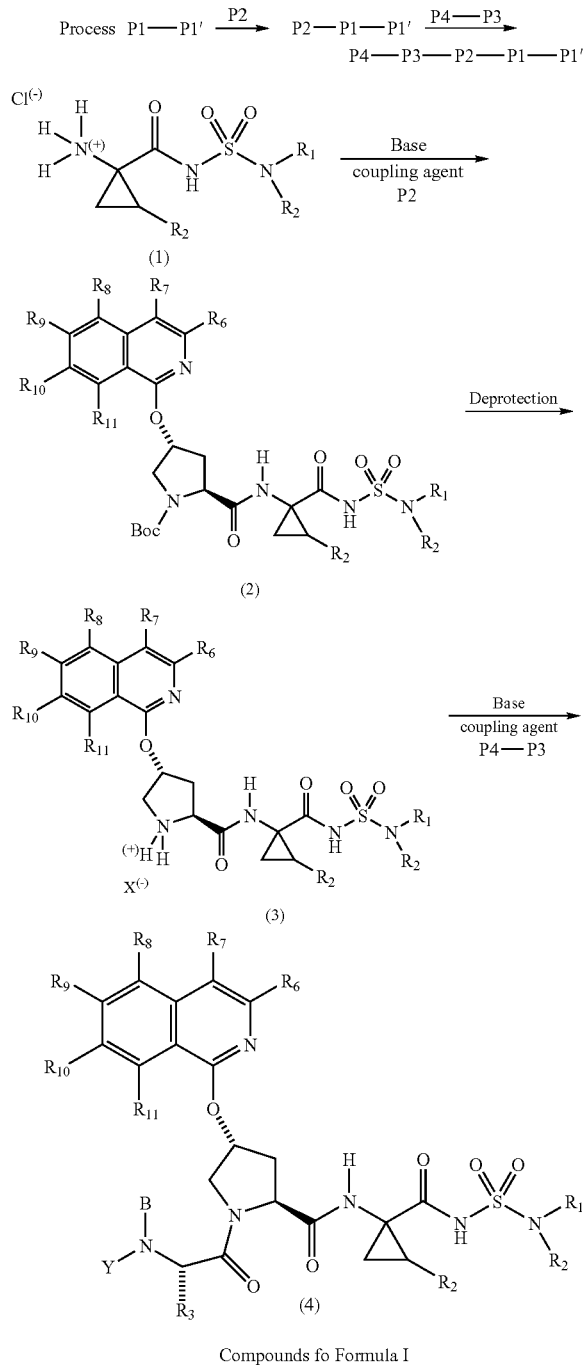

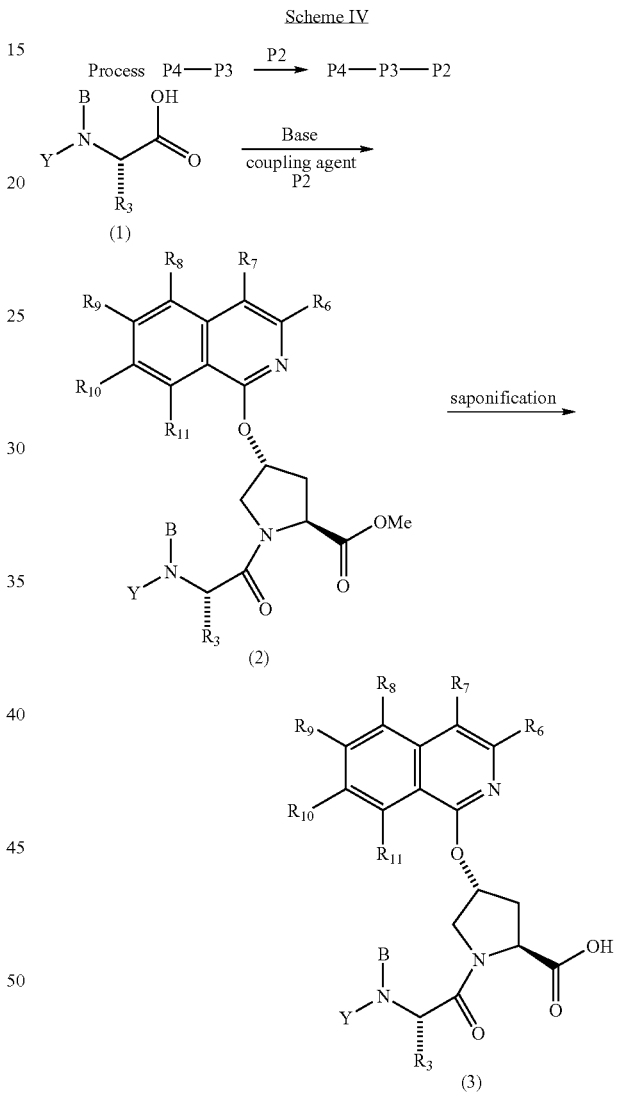

Compounds of Formula 1 can also be converted into other compounds of Formula I as described herein. An example of such a process is shown in Scheme VI wherein a compound of Formula I (1) which bears a Boc group at the P4 position is converted to a compound of Formula I (3) wherein said compound bears a urea group at the P4 position. The conversion of (1) to (3) can be carried out in a two step process the first of which is the conversion of (1) to amine (2) by treatment of (1) with an acid such as TFA in a solvent such as methylene chloride. The resulting amine TFA salt can be treated with an isocyanate in the presence of one equivalent of base to provide a compound of Formula I (3)

wherein the P3 moiety is capped with a urea. As previously noted one skilled in the art will recognize that intermediate (2) can be used as starting materials for the preparation of compounds of Formula I wherein the P3 group is capped with an amide or a sulfonamide, or thiourea, or a sulfamide. The construction of said compounds of Formula I can be achieved using standard conditions for the formation of said P4 functionalities from amines.3

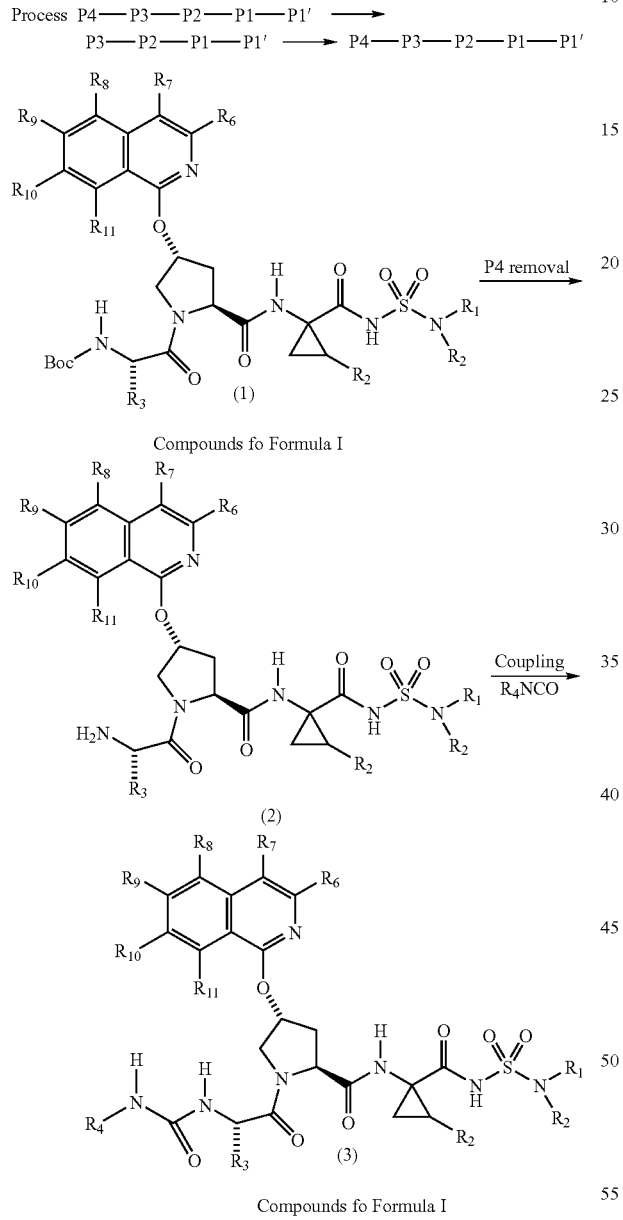

Compounds fo Formula I

In the construction of compounds of Formula I, the P1' terminus is incorporated into the molecules using one of the general processes outlined above and described in more detail below. These P1' sulfamides can be prepared in a two step process using chlororsulfonylisocyanate as starting material. Said isocynate can be hydrolyzed to the corresponding chlorosulfamoyl chloride by treatment with water in a solvent such as THF. The intermediate sulfamoylchloride upon treatment with an amine, in the presence of a base, provides the desired sulfamide derivatives.

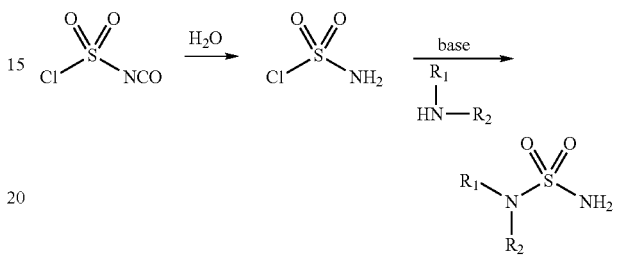

The P1 elements utilized in generating compounds of Formula I are in some cases commercially available, but are otherwise synthesized using the methods described herein and subsequently incorporated into compounds of Formula I using the methods described herein. The substituted P1 cyclopropylamino acids can be synthesized following the general process outline in Scheme VIII.

Treatment of commercially available or easily synthesized imine (1) with 1,4-dihalobutene (2) in presence of a base produces, provides the resulting imine (3). Acid hydrolysis of 3 then provides 4, which has an allyl substituent syn to the carboxyl group as a major product. The amine moiety of 4 can protected using a Boc group to provide the fully protected amino acid 5. This intermediate is a racemate which can be resolved by an enzymatic process wherein the ester moiety of 5 is cleaved by a protease to provide the corresponding carboxylic acid. Without being bound to any particular theory, it is believed that this reaction is selective in that one of the enantiomers undergoes the reaction at a much greater rate than its mirror image providing for a kinetic resolution of the intermediate racemate. In the examples cited herein, the more preferred stereoisomer for integration into compounds of Formula I is 5a which houses the (1R,2S) stereochemistry. In the presence of the enzyme, this enantiomer does not undergo ester cleavage and thereby this enantiomer 5a is recovered from the reaction mixture. However, the less preferred enantiomer, 5b with houses the (1S,2R) stereochemistry undergoes ester cleavage, i.e., hydrolysis, to provide the free acid 6. Upon completion of this reaction, the ester 5a can be separated from the acid product 6 by routine methods such as, for example, aqueous extraction methods or chromatography.

Scheme VIII

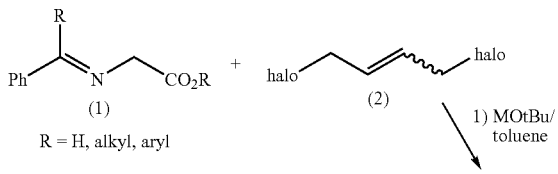

R = H, alkyl, aryl

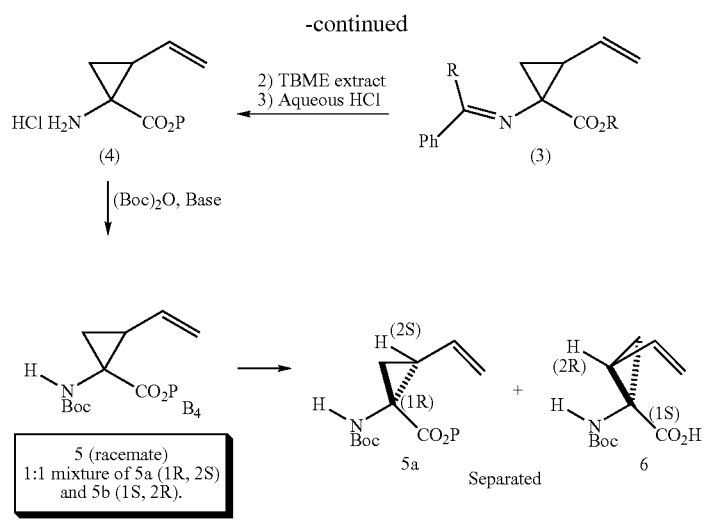

Procedures for making P2 intermediates and compounds of Formula I are shown in the Schemes below. It should be noted that in many cases reactions are depicted for only one position of an intermediate. However, it is to be understood that such reactions could be used to impart modifications to other positions within this intermediate. Moreover, said intermediates, reaction conditions and methods given in the specific examples are broadly applicable to compounds with other substitution patterns. The general Schemes outlined below are followed with examples herein. Both general and specific examples are non-limiting, as for example the isoquinoline nucleus is shown as part of the general scheme, Scheme IX, however, this pathway represents a viable process for the construction of alternate heterocycle substituents as replacements for the isoquinoline element, such as quinolines, or pyridines.

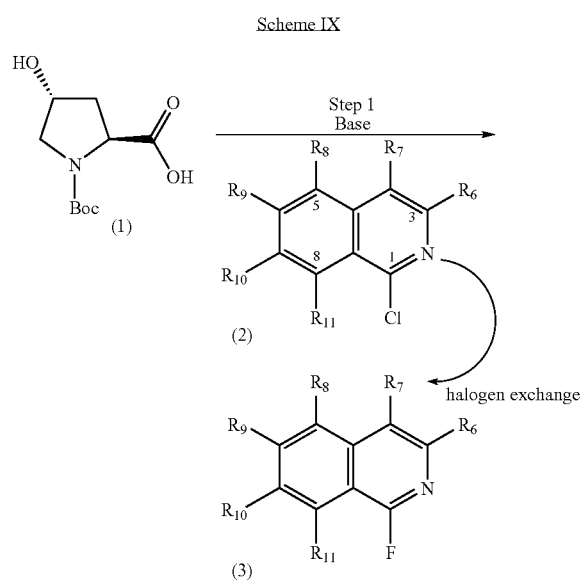

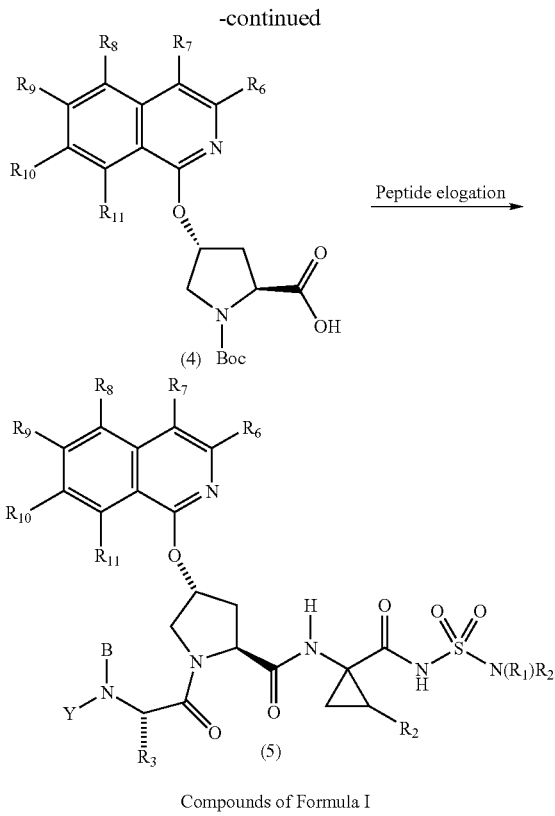

Scheme IX shows the coupling of an N-protected C4-hydroxyproline moiety with a heterocycle to form intermediate (4) and the subsequent modification of said intermediate (4) to a compound of Formula I by the process of peptide elongation as described herein. It should be noted that in the first step, that is the coupling of the C4-hydroxy proline group with the heteroaryl element, a base is employed. One skilled in the art would recognized that this coupling can be done using bases such as potassium tert-butoxide, or sodium hydride, in solvent such as DMF or DMSO or THF. This coupling to the isoquinoline ring system occurs at the C1 position (numbering for isoquinoline ring system shown in intermediate 2 of Scheme IX) and is directed by the chloro group which is displaced in this process. It should be noted that the alternative leaving groups can be utilized at this position such as a fluoro as shown in the Scheme. Said fluoro intermediates (3) are available from the corresponding chloro compound using literature procedures described herein. It should also be noted that the position of the leaving group (chloro or fluoro) in a given ring system can vary as shown in Scheme X, wherein the leaving group (fluoro in this example) is in the C6 position of the isoquinoline ring system of intermediate (2).

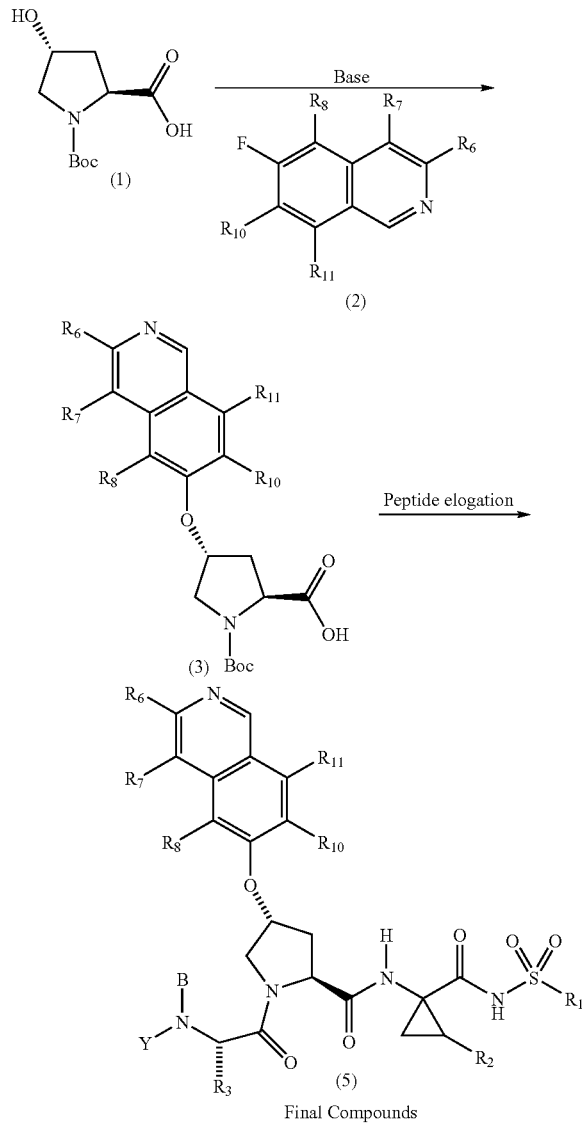

It should be further noted that the position of the ring heteroatom(s) in intermediates like (2) of Scheme IX and Scheme X is also variable, as defined by the term heterocycle described herein. In Scheme X intermediate (2) can be coupled to a C4 hydroxy proline derivative to provide the P2 element (3). This C6-substituted isoquinoline derivative can be converted to compounds of Formula I using the methods described herein.

An alternative to the method described above for the coupling of the C4-hydroxyproline to aromatics and heteroaromatics, is provided in the Mitsunobu reaction as depicted in

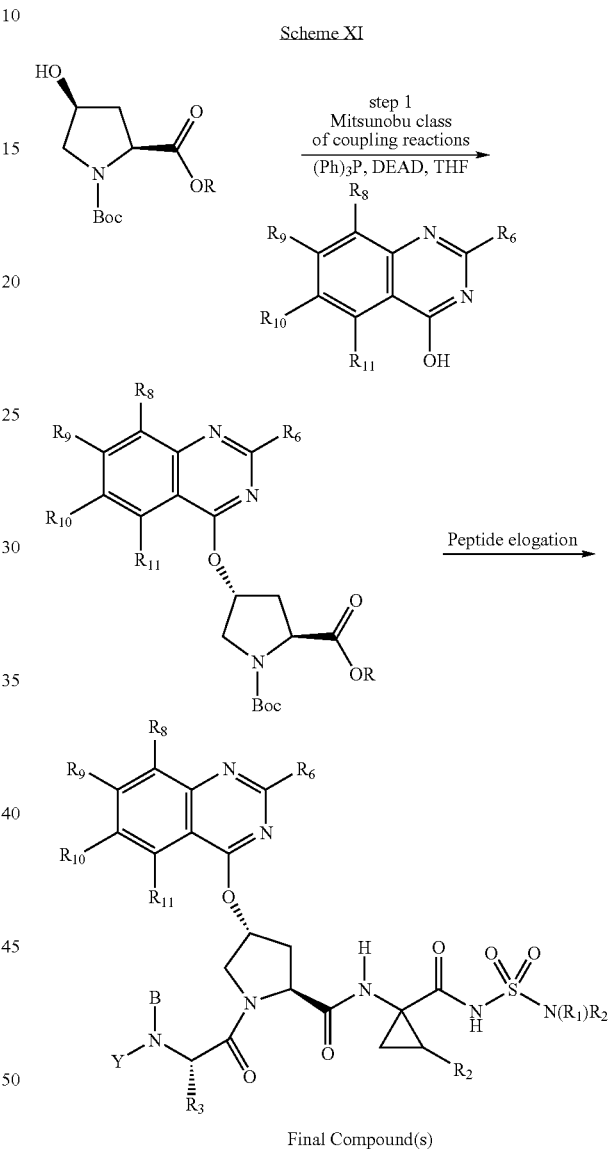

step 1 of Scheme XI. In this general reaction Scheme a C4-hydroxy proline derivative is coupled to a quinazoline ring system. This reaction makes use of reagents such as triphenylphosphine and DEAD (diethylazodicarboxylate) in aprotic solvents such as THF or dioxane and can be used for the formation of aryl and heteroaryl ethers. Note that in the course of this coupling reaction the stereochemistry of the C4 chiral center in the C4-hydroxyproline derivative is inverted and thereby it is necessary to use the C4-hydroxyproline derivative housing the (S) stereochemistry at the C4 position as starting material. (as shown in Scheme XI). It should be noted that numerous modifications and improvements of the Mitsunobu reaction have been described in the literature, the teachings of which are incorporated herein.

In a subset of examples herein, isoquinolines are incorporated into the final compounds and specifically into the P2 region of said compounds. One skilled in the art would recognize that a number of general methods are available for the synthesis of isoquinolines. Moreover, said isoquinolines generated by these methods can be readily incorporated into final compounds of Formula I using the processes described herein. One general methodology for the synthesis of isoquinolines is shown in Scheme XII, wherein cinnamic acid derivatives, shown in general form as structure (2) are

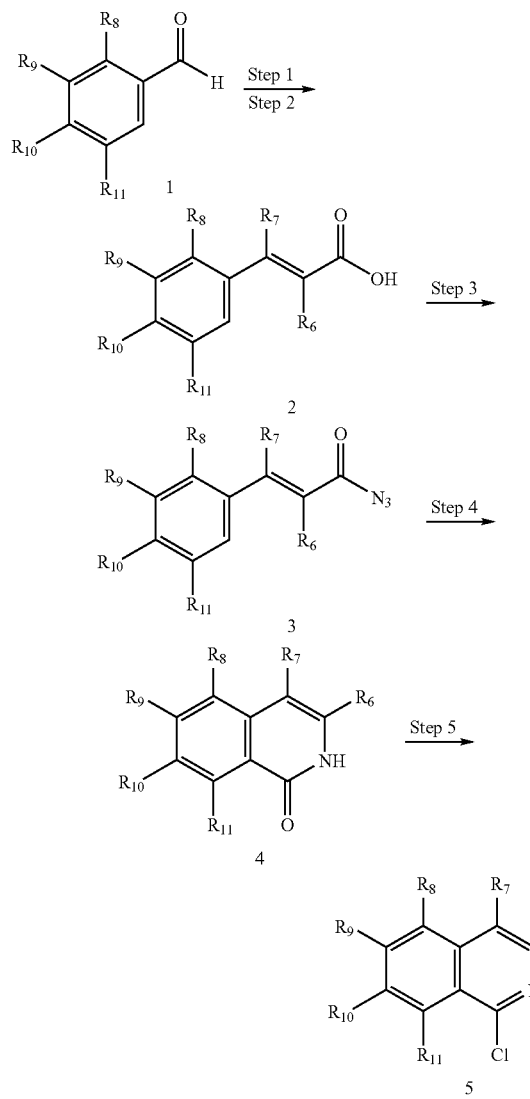

Reference: N. Briet at al, Tetrahedron, 2002, 5761 converted to 1-chloroisoquinolines in a four step process. Said chloroisoquinolines can be subsequently used in coupling reactions to C4-hydroxyproline derivatives as described herein. The conversion of cinnamic acids to chloroquinolines begins with the treatment of cinnamic acid with an alkylcholorformate in the presence of a base. The resulting anhydride is then treated with sodium azide which results in the formation of an acylazide (3) as shown in the Scheme. Alternate methods are available for the formation of acylazides from carboxylic acids as for example said carboxylic acid can be treated with diphenylphosphorylazide (DPPA) in an aprotic solvent such as methylene chloride in the presence of a base. In the next step of the reaction sequence the acylazide (3) is coverted to the corresponding isoquinolone (4) as shown in the Scheme. In the event the acylazide is heated to a temperature of approximately 190 degress celcius in a high boiling solvent such a diphenylmethane. This reaction is general and provides moderate to good yields of substituted isoquinolone from the corresponding cinnamic acid derivatives. It should noted that said cinnamic acid derivatives are available commercially or can be obtained from the corresponding benzaldehyde (1) derivative by direct condensation with malonic acid or derivatives thereof and also by employing a Wittig reaction. The intermediate isoquinolones (4) of Scheme XII can be converted to the corresponding 1-chloroisoquinoline by treatment with phosphorous oxychloride. This reaction is general and can be applied to any of the isoquinolones, quinolones or additional heterocycles as shown herein to covert a hydroxy substituent to the corresponding chloro compound when said hydroxy is in conjugation with a nitrogen atom in said heterocylic ring systems.

An alternative method for the synthesis of the isoquinoline ring system is the Pomeranz-Fritsh procedure. This general method is outlined in Scheme XIII. The process begins with the conversion of a benzaldehyde derivative (1) to a functionalized imine (2). Said imine is then converted to the isoquinoline ring system by treatment with acid at elevated

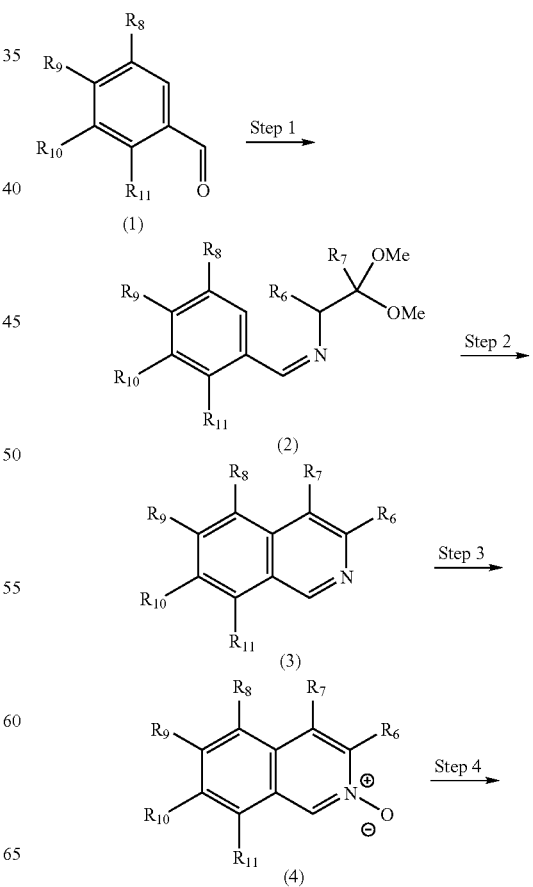

-continued

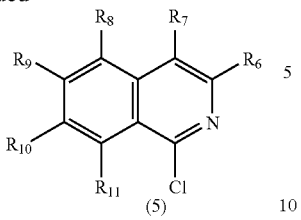

Pomeranz-Fritsch synthesis
K. Hirao, R. Tsuchiya, Y. Yano, H. Tsue, Heterocycles 42(1) 1996, 415-422 temperature. This isoquinoline synthesis of Scheme XIII is general, and it should be noted that this process is particularly useful in procuring isoquinoline intermediates that are substituted at the C8 position (note: in intermediate (3) of Scheme XIII the C8 position of the isoquinoline ring is substituted with substutuent $R_{11}$). The intermediate isoquinolines (3) can be converted to the corresponding 1-chloroquinolines (5) in a two step process as shown. The first step in this sequence is the formation of the isoquinoline N-oxide(4) by treatment of isoquinoline (3) with meta-chloroperbenzoic acid in an aprotic solvent such as dichloromethane. Intermediate (4) can be converted to the corresponding 1-chloroquinoline by treatment with phosphorous oxychloroide in refluxing chloroform. Note this two step process is general and can be employed to procure chloroisoquinolines and chloroquinolines from the corresponding isoquinolines and quinolines respectively.

Another method for the synthesis of the isoquinoline ring system is shown in Scheme XIV. In this process an ortho-alkylbenzamide derivative (1) is treated with a strong Scheme XIV

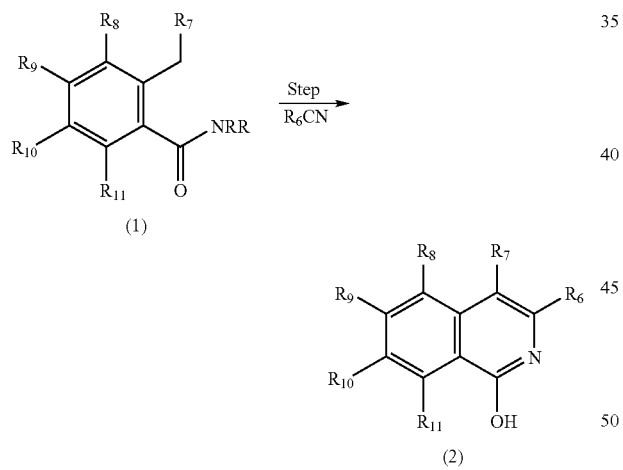

base such as tert-butyl lithium in a solvent such as THF at low temperature. To this reaction mixture is then added a nitrile derivative, which undergoes an addition reaction with the anion derived from deprotonation of (1), resulting in the formation of (2). This reaction is general and can be used for the formation of substituted isoquinolines. Intermediate (2) of Scheme XIV can be converted to the corresponding 1-chloroquinoline by the methods described herein.

An additional method for the synthesis of isoquinolines is shown in Scheme XV. The deprotonation of intermediate (1) using tert-butyl lithium is described above. In the present method however, said intermediate anion is trapped by an ester, resulting in the formation of intermediate (2) as shown below. In a subsequent reaction ketone (2) is condensed with ammoniumn acetate at elevated temperature providing for the formation of quinolone (3). This reaction is general and can be applied for the construction of substituted isoquinolones which can then be converted to the corresponding 1-chloroisoquinolines as described herein.

Scheme XV

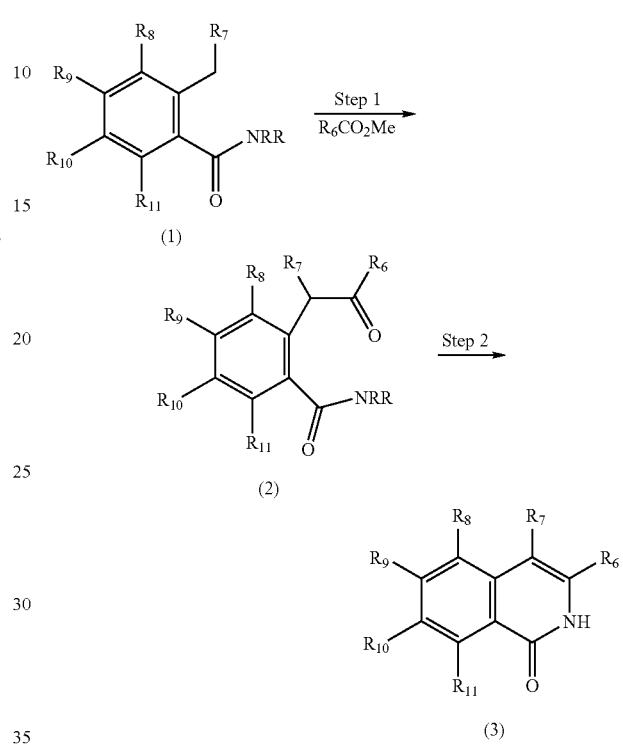

Yet an additional method for the construction of isoquinolines is found in Scheme XVI. In the first step of this process an ortho-alkylarylimine derivatives such as (1) is subjected to deprotonation conditions (sec-butyl lithium, THF) and the resulting anion is quenched by Scheme XVI

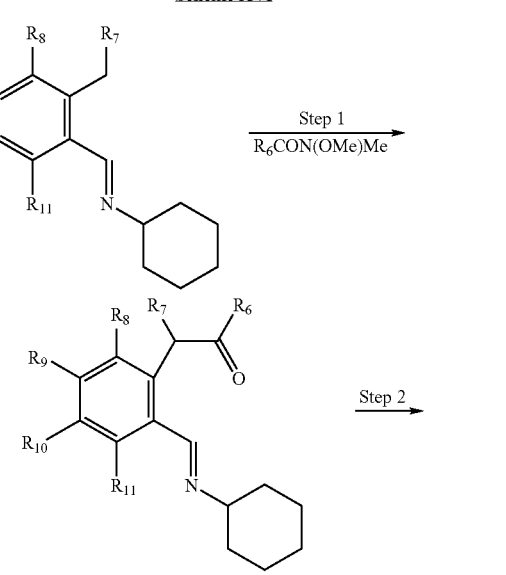

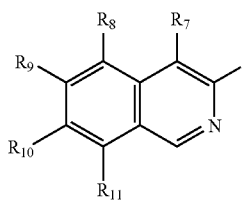

L. Flippin, J. Muchowski, JOC, 1993, 2631-2632 the addition of an activated carboxylic acid derivative such as a Weinreb amide. The resulting keto imine (2) can be converted to the corresponding isoquinoline by condensation with ammonium acetate at elevated temperatures. This method is general and can be used for the synthesis of substituted isoquinolines. Said isoquinolines can be converted to the corresponding 1-chloroquinoline by the methods described herein.

The heterocycles described herein, and which are incorporated into the compounds of Formula I can be further functionalized. One skilled in the art will recognize that additional functionalization of said heterocycles can be done either before or after incorporation of these functionalities into compounds of Formula I. The following Schemes illustrate this point. For example Scheme XVII shows the conversion of a 1-chloro-6-fluoro-isoquinoline Scheme XVII

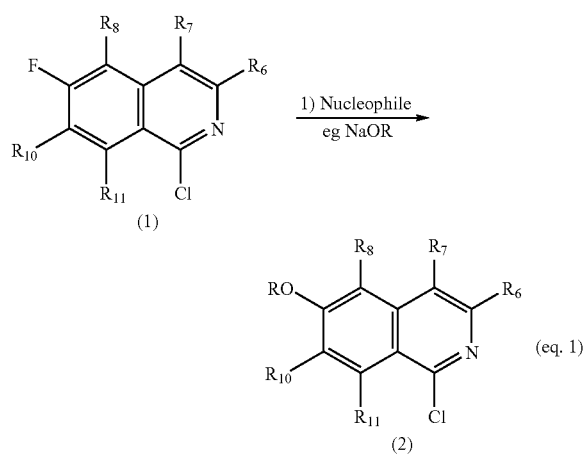

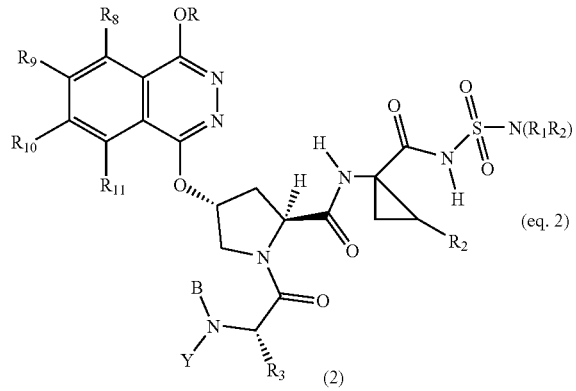

to the corresponding 1-chloro-6-alkoxy-isoquinoline species, by treatment of (1) of (eq. 1) with a sodium or potassium alkoxide species in the alcohol solvent from which the alkoxide is derived at room temperature. In some cases it may be necessary to heat the reaction to drive it to completion. Said chloroquinoline can be incorporated into a compound of Formula I using the art described herein.

Modifications of a P2 heterocyclic element can also be done after it's incorporation into compounds of Formula I as shown in (eq.2) of Scheme VXII. Specifically compounds such as (1) in (eq. 2) which contain a leaving group in the pthalazine nucleus can be displaced by a nucleophile such as an alkoxide in solvents such as the corresponding alcohol from which the alkoxide is derived. These reaction scan be conducted at room temperature but in some cases it may be necessary to heat the reaction to drive it to completion.

Scheme XVIII provides a general example for the modification of heterocycles as defined herein by employing palladium mediated coupling reactions. Said couplings can be employed to functionalize a heterocycle at each position of the ring system providing said ring is suitably activated or functionalized, as for example with a chloride as shown in the Scheme. This sequence begins with 1-chloroisoquinoline (1) which upon treatment with metachloroperbenzoic acid can be converted to the corresponding N-oxide (2). Said intermediate (2) can be converted to the corresponding 1,3-dichloroisoquinoline (3) by treatment with phosphorous oxychloride in refluxing chloroform. Intermediate (3) can be coupled with N-Boc-4-hydroxyproline by the methods described herein to provide intermediate (5) as shown in the Scheme. Intermediate (5) can undergo a Suzuki coupling with an aryl boronic acid, in the presence of a palladium reagent and base, and in a solvent such as THF or toluene or DMF to provide the C3-arylisoquinoline intermediate (6). Heteroarylboronic acids can also be employed in this Pd mediated coupling process to provide C3-heteroarylisoquinolines. Intermediate (6) can be converted into final compounds of Formula I by the methods described herein.

Scheme XVIII

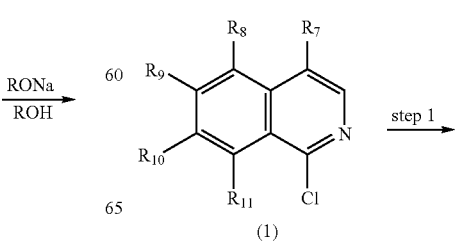

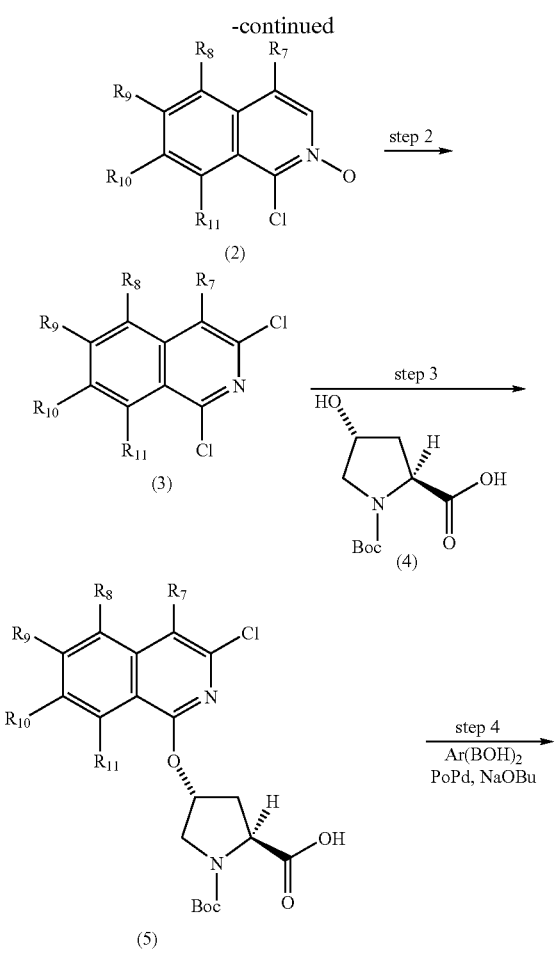

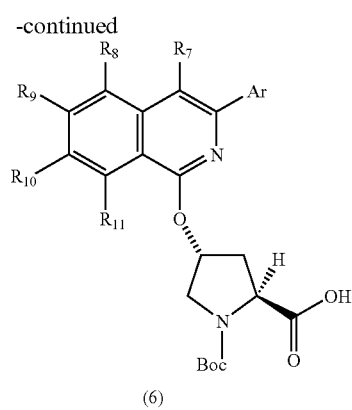

Palladium mediated couplings of heteroaryl systems with aryl or heteroaryl elements can also be employed at a later synthetic stage in the construction of compounds of Formula I as shown in Scheme IXX. Therein tripeptide acylsulfonamide intermediate (1) is coupled to a 1-chloro-3-bromoisoquinoline (2) using the previously described process of alkoxide displacement of an heteroarylhalo moiety to provide intermediate (3). The coupling of (1) and (2) is most efficient in the presence of a catalyst such as lanthanum chloride as described herein. The isoquinoline ring system of intermediate (3) can be further functionalized by employing either Suzuki couplings (Process 1: subjecting (3) to heteroaryl or aryl boronic acids in the presence of a palladium catalyst such as palladium tetra(triphenylphosphine) and a base such as cesium carbonate in solvents such as DMF) or Stille couplings (Process 2: subjecting (3) to heteraryl or aryl tin derivatives in the presence of palladium catalyst such as palladium tetra(triphenylphosphine in solvents such as toluene).

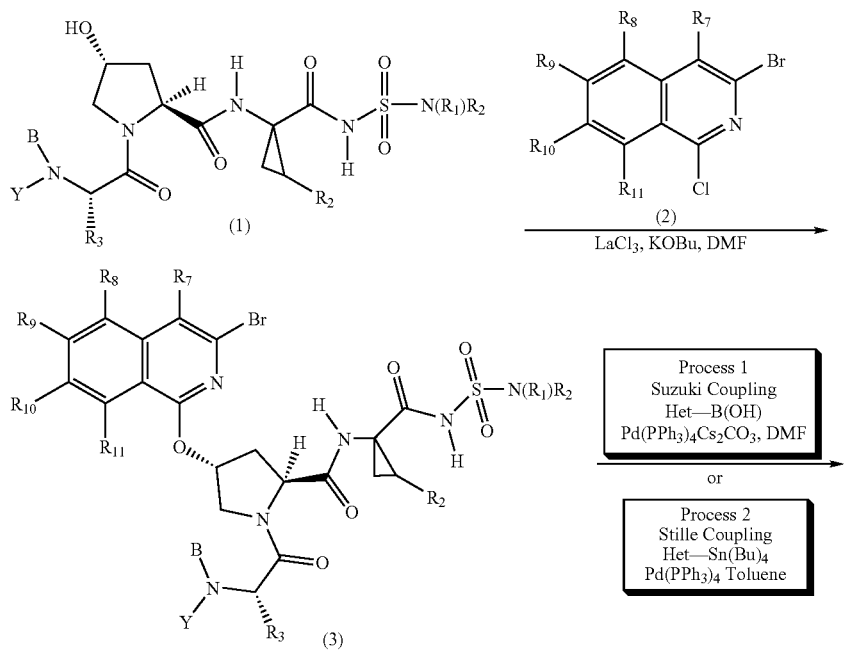

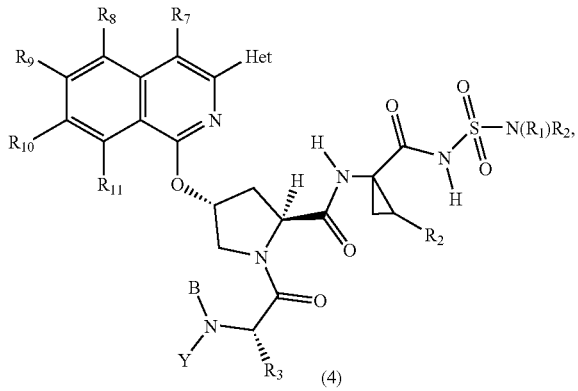

(4)

Palladium reactions can also be employed to couple C4-amino proline elements with functionalized heterocycles. Scheme XX shows intermediate (1) coupling with a fumctionalized isoquinoline in the presence of a palladium catalyst and a base in a solvent such as toluene. Intermediates like (3) can be converted to compounds of Formula I using the methods described herein.

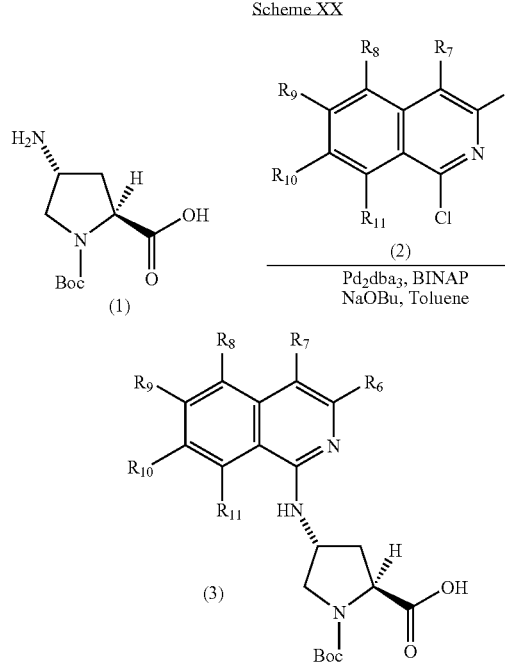

The construction of functionalized isoquinoline ring systems is also possible employing [4+2] cycloaddition reactions. For example (Scheme XXI) the use of vinyl isocyantes (1) in cycloaddition reactions with benzyne precusors (2) provides functionalized isoquinolones (3). Said isoquinolines can be incorporated into compounds of Formula I using the methods described herein.

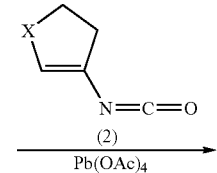

Compounds of the invention can also be prepared by utilizing methods known to thise skilled in the art, such as, for example, the methods described in patent application WO 03/099274, published Dec. 3, 2003. For example, WO 03/099274 provides extensive examples and teachings on the prepration of proline derivatives as intermediates and these intermediates can be used in the preparation of compound of Formula 1.

The present invention also provides compositions comprising a compound of the present invention, or a pharmaceutically acceptable salt, solvate or prodrug thereof, and a pharmaceutically acceptable carrier. Pharmaceutical compositions of the present invention comprise a therapeutically effective amount of a compound of the invention, or a pharmaceutically acceptable salt, solvate or prodrug thereof, and a pharmaceutically acceptable carrier, with a pharmaceutically acceptable carrier, e.g., excipient, or vehicle diluent.

The active ingredient, i.e., compound, in such compositions typically comprises from 0.1 weight percent to 99.9 percent by weight of the composition, and often comprises from about 5 to 95 weight percent.

Thus, in one aspect of the invention, there is provided a composition comprising the compound of formula 1 and a pharmaceutically acceptable carrier. Preferably, the composition further comprises a compound having anti-HCV activity. As used herein, the term "anti-HCV activity" means the compound is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH and a nucleoside analog for the treatment of an HCV infection. Often, the other compound having anti-HCV activity is effective to inhibit the function of target in the HCV life cycle other than the HCV serine protease.

In one preferred aspect, the compound having anti-HCV activity is an interferon. Preferably, the interferon is selected from the group consisting of interferon alpha 2B, pegylated interferon alpha, consensus interferon, interferon alpha 2A and lymphoblastiod interferon tau.

In another aspect of the invention, the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In one preferred aspect of the invention, the composition comprises a compound of the invention, an interferon and ribavirin.

In another preferred aspect of the invention, the compound having anti-HCV activity is a small molecule compound. As used herein, the term "small molecule compound" means a compound having a molecular weight of less than 1,500 daltons, preferably less than 1000 daltons. Preferably, the small molecule compound is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, inosine monophophate dehydrogenase ("IMPDH") and a nucleoside analog for the treatment of an HCV infection.

Certain illustrative HCV inhibitor compounds which can be administered with the compounds of the present invention include those disclosed in the following publications: WO 02/04425 A2 published Jan. 17, 2002, WO 03/007945 A1 published Jan. 30, 2003, WO 03/010141 A2 published Feb. 6, 2003, WO 03/010142 A2 published Feb. 6, 2003, WO 03/010143 A1 published Feb. 6, 2003, WO 03/000254 A1 published Jan. 3, 2003, WO 01/32153 A2 published May 10, 2001, WO 00/06529 published Feb. 10, 2000, WO 00/18231 published Apr. 6, 2000, WO 00/10573 published Mar. 2, 2000, WO 00/13708 published Mar. 16, 2000, WO 01/85172 A1 published Nov. 15, 2001, WO 03/037893 A1 published May 8, 2003, WO 03/037894 A1 published May 8, 2003, WO 03/037895 A1 published May 8, 2003, WO 02/100851 A2 published Dec. 19, 2002, WO 02/100846 A1 published Dec. 19, 2002, EP 1256628 A2 published Nov. 13, 2002, WO 99/01582 published Jan. 14, 1999, WO 00/09543 published Feb. 24, 2000.

Table 1 below lists some illustrative examples of compounds that can be administered with the compounds of this invention. The compounds of the invention can be administered with other anti-HCV activity compounds in combination therapy, either jointly or separately, or by combining the compounds into a composition.

TABLE 1

| Brand Name | Type of Inhibitor or Target | Source Company |
|---|---|---|
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon - α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/ immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/ SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/ Ribavirin | PEGylated IFN-α2b/ribavirin | Schering-Plough Corporation, Kenilworth, NJ |

TABLE 1-continued

| Brand Name | Type of Inhibitor or Target | Source Company |
| --- | --- | --- |
| Zadazim | immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |
| VX-950/LY-570310 | serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Israel |

The pharmaceutical compositions of this invention may be administered orally, parenterally or via an implanted reservoir. Oral administration or administration by injection are preferred. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intrasynovial, intrasternal, intrathecal, and intralesional injection or infusion techniques.

When orally administered, the pharmaceutical compositions of this invention may be administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added. Other suitable carriers for the above noted compositions can be found in standard pharmaceutical texts, e.g. in "Remington's Pharmaceutical Sciences", 19th ed., Mack Publishing Company, Easton, Pa., 1995.

The pharmaceutical compositions can be prepared by known procedures using well-known and readily available ingredients. The compositions of this invention may be formulated so as to provide quick, sustained or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, beadlets, lozenges, sachets, elixirs, suspensions, emulsions, solutions, syrups, aerosols, (as a solid or in a liquid medium), soft and hard gelatin capsules, suppositories, sterile injectable solutions, sterile packaged powders and the like. Further details concerning the design and preparation of suitable delivery forms of the pharmaceutical compositions of the invention are known to those skilled in the art.

Dosage levels of between about 0.01 and about 1000 milligram per kilogram ("mg/kg") body weight per day, preferably between about 0.5 and about 250 mg/kg body weight per day of the compounds of the invention are typical in a monotherapy for the prevention and treatment of HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this invention comprise a combination of a compound of the invention and one or more additional therapeutic or prophylactic agent, both the compound and the additional agent are usually present at dosage levels of between about 10 to 100%, and more preferably between about 10 and 80% of the dosage normally administered in a monotherapy regimen.

When these compounds or their pharmaceutically acceptable enantiomers, diastereomers, salts, solvates or prodrugs are formulated together with a pharmaceutically acceptable carrier, the resulting composition may be administered in vivo to mammals, such as man, to inhibit HCV serine protease or to treat or prevent HCV virus infection.

Accordingly, another aspect of this invention provides methods of inhibiting HVC serine protease activity in patients by administering a compound of the present invention or a pharmaceutically acceptable salt or solvate thereof.

In one aspect of the invention, there is provided a method of inhibiting the function of the HCV serine protease comprising contacting the HCV serine protease with a compound of the invention. In another aspect, there is provided a method of treating an HCV infection in a patient, comprising administering to the patient a therapeutically effective amount of the compound of the invention, or a pharmaceutically acceptable solvate, prodrug or salt thereof.

Preferably, the method of administering the compound is effective to inhibit the function of the HCV serine protease. In a preferred aspect, the method further comprises administering another compound having anti-HCV activity (as described above) prior to, after or concurrently with a compound of the invention.

The compounds of the invention may also be used as laboratory reagents. Compounds may be instrumental in providing research tools for designing of viral replication assays, validation of animal assay systems and structural biology studies to further enhance knowledge of the HCV disease mechanisms. Further, the compounds of the present invention are useful in establishing or determining the binding site of other antiviral compounds, for example, by competitive inhibition.

The compounds of this invention may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

Further, the compounds and compositions of the invention can be used for the manufacture of a medicament for treating an HCV infection in a patient.

EXAMPLES

The specific examples that follow illustrate the syntheses of the compounds of the instant invention, and are not to be construed as limiting the invention in sphere or scope. The methods may be adapted to variations in order to produce compounds embraced by this invention but not specifically disclosed. Further, variations of the methods to produce the same compounds in somewhat different manner will also be evident to one skilled in the art.

Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts (δ) are reported in parts per million. Flash chromatography was carried out on silica gel ($SiO_2$) according to Still's flash chromatography technique (W. C. Still et al., J. Org. Chem., (1978), 43, 2923).

All Liquid Chromatography (LC) data were recorded on a Shimadzu LC-10AS liquid chromatograph using a SPD-10AV UV-Vis detector and Mass Spectrometry (MS) data were determined with a Micromass Platform for LC in electrospray mode (ES+).

Unless otherwise noted, in the following examples each compound was analyzed by LC/MS, using one of seven methodologies, having the following conditions.

Columns:
  (Method A)—YMC ODS S7 C18 3.0×50 mm
  (Method B)—YMC ODS-A S7 C18 3.0×50 mm
  (Method C)—YMC S7 C18 3.0×50 mm
  (Method D)—YMC Xterra ODS S7 3.0×50 mm
  (Method E)—YMC Xterra ODS S7 3.0×50 mm
  (Method F)—YMC ODS-A S7 C18 3.0×50 mm
  (Method G)—YMC C18 S5 4.6×50 mm]
Gradient: 100% Solvent A/0% Solvent B to 0% Solvent A/100% Solvent B
Gradient time: 2 min. (A, B, D, F, G); 8 min. (C, E)
Hold time: 1 min. (A, B, D, F, G); 2 min. (C, E)
Flow rate: 5 milliliters/min ("mL/min")
Detector Wavelength: 220 nanometer ("nm")
Solvent A: 10% MeOH/90% $H_2O$/0.1% TFA
Solvent B: 10% $H_2O$/90% MeOH/0.1% TFA.

The abbreviations used in the present application, including particularly in the illustrative examples which follow, are well-known to those skilled in the art. Some of the abbreviations used are as follows:

| | |
|---|---|
| rt | room temperature |
| Boc | tert-butyloxycarbonyl |
| DMSO | dimethylsulfoxide |
| EtOAc | ethyl acetate |
| t-BuOK | potassium t-butoxide |
| $Et_2O$ | diethyl ether |
| TBME | tert-butylmethyl ether |
| THF | tetrahydrofuran |
| CDI | carbonyldiimidazole |
| DBU | 1,8-diazabicyclo[5.4.0]undec-7-ene |
| TFA | trifluoroacetic acid |
| NMM | N-methylmorpholine |
| HATU | O-7-azabenzotriazol-1-yl |
| HBTU | O-{1H-benzotriazol-1-yl)-N,N,N',N'-tetramethyluronium hexafluorophosphate |
| HOBT | N-hydroxybenzotriazole |
| PyBrop | bromo-bis-pyrrolidine-phosphonium hexafluorophosphate |
| DMF | dimethylformamide |
| MeOH | methanol |
| EDTA | ethylenediaminetetraacetic acid |
| HRMS | high resolution mass spectrometry |
| DMAP | 4-dimethylaminopyridine |
| DIPEA | diisopropylethylamine |
| DCM | dichloromethane |
| DCE | dichloroethane |

Preparation of Intermediates:

Example 1

Preparation of 4-(Isoquinolin-1-yloxy)-pyrrolidine-1,2-dicarboxylic acid 1-tert-butyl ester

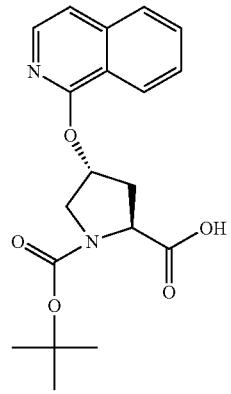

A suspension of Boc-L-4-hydroxyproline (N-Boc(2S, 4R)-hydroxyproline) (3.85 g 16.6 millimole ("mmol") (CHEM-IMPEX International) in DMSO (60 mL) was cooled in an ice bath for ~3 minutes, and then t-BuOK (4.66 g, 41.5 mmol) was added. Stirring and cooling in the ice bath was continued for a few minutes until a solid mass formed. At this time the reaction mixture was allowed to warm to rt over 1.5 h to give a clear colorless solution. 1-Chloroisoquinoline (3.0 g, 18.3 mmol) was added in two portions 10 min apart. The reaction was stirred for 24 h at rt. The dark reaction mixture was partitioned between ether (200 mL) and water (600 mL). The aqueous phase was acidified to pH 4 using 4N HCl. The resulting milky yellow solution was extracted with ether (4×200 mL). The combined ether extracts were dried ($MgSO_4$), filtered, and concentrated in vacuo to give a golden oil. Flash chromatography (2–4% MeOH/$CH_2Cl_2$) gave 5.69 g (96%) of 4-(isoquinolin-1-yloxy)-pyrrolidine-1,2-dicarboxylic acid 1-tert-butyl ester as an off-white solid: LC-MS (Method A, retention time: 3.06 min), MS m/z 359 ($M^+$+1).

Example 2

Preparation of 4-(6-Methoxy-isoquinolin-1-yloxy)-pyrrolidine-1,2-dicarboxylic acid 1-tert-butyl ester

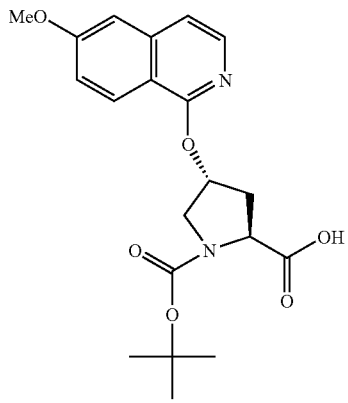

Step 1 of Example 2

Preparation of 6-Methoxy-2H-isoquinolin-1-one

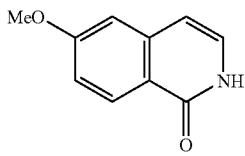

6-Methoxy-2H-isoquinolin-1-one

To a solution of 3-methoxy cinnamic acid (11.04 g, 62 mmol), triethylamine (12.52 g, 124 mmol) in acetone (80 mL) was added ethyl chloroformate dropwise at 0° C. After stirring at this temperature for 1 h, aqueous $NaN_3$ (6.40 g, 100 mmol in 35 mL $H_2O$) was added dropwise and the reaction mixture was stirred for 16 h at the ambient temperature. Water (100 mL) was added to the mixture and the volatile was removed in vacuo. The resulting slurry was extracted with toluene (3×50 mL) and the combined organic layers were dried over $MgSO_4$. This dried solution was added dropwise to a heated solution of diphenylmethane (50 mL) and tributylamine (30 mL) at 190° C. The toluene was distilled off as added. After complete addition, the reaction temperature was raised to 210° C. for 2 h. After cooling, the precipitated product was collected by filtration, washed with hexane (2×50 mL), dried to yield a white solid (5.53 g, 51%), MS m/z 176 ($M^+$+H).

Step 2 of Example 2

Preparation of 1-chloro-6 methoxy isoquinoline

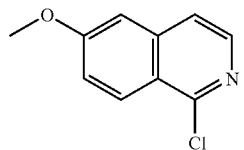

6-Methoxy-2H-isoquinolin-1-one in $POCl_3$ was heated to gentle reflux for 3 h then evaporated in vacuo. The residue was poured into ice-water (20 mL) and neutralized to pH 10 with 10 M NaOH. Extracted with $CHCl_3$. The organic layer was washed with brine, dried over $MgSO_4$, filtered, evaporated. The residue was purified by flash chromatography (hexane-EtOAc) to afford a white solid.

$^1$H NMR (CD$_3$OD) δ 3.98 (s, 3H), 7.34–7.38 (m, 2H), 7.69 (d, J=5.5 Hz, 1H), 8.10 (d, J=6.0 Hz, 1H), 8.23 (d, J=9.5 Hz, 1H), MS m/z 194 ($M^+$+H).

Step 3 of Example 2

Preparation of 4-(6-Methoxy-isoquinolin-1-yloxy)-pyrrolidine-1,2-dicarboxylic acid 1-tert-butyl ester

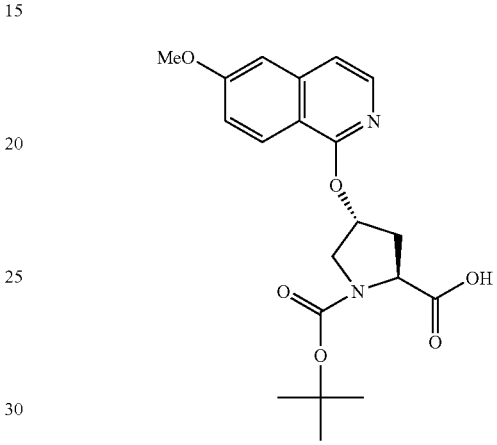

As described in Example 1 except that 1-chloro-6-methoxy-isoquinoline was used in place of 1-chloro-isoquinoline. $^1$H NMR (400 MHz, CD$_3$OD) δ 1.41 (m, 9H), 2.44 (m, 1H), 2.75 (m, 1H), 3.82–3.92 (m, 2H), 3.96 (s, 3H), 4.45 (m, 1H), 5.50 (m, 1H), 7.20 (m, 1H), 7.27 (d, J=5.14 Hz, 1H), 7.41 (d, J=2.45 Hz, 1H), 7.48–7.59 (m, 3H), 8.00–8.05 (m, 2H), 8.08 (d, J=9.29 Hz, 1H). LC-MS (retention time: 2.140 min.), MS m/z 465 (MH$^+$).

Example 3

Preparation of P1 Elements for Incorporation Into Compounds of Formula I

I. Preparation of racemic (1R,2S)/(1S,2R)-1-amino-2-vinylcyclopropane carboxylic acid ethyl ester hydrochloride (Method A and Method B) and chiral resolution of this racemate for the preparation of N-(1R,2S)-1-amino-2-vinylcyclopropane carboxylic acid ethyl ester hydrochloride (Method C)

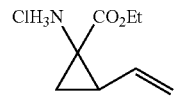

The named compound was made racemic by each of the following methods A and B. This racemate could also be resolved to afford chiral Boc-(1R,2S)-1-amino-2-vinylcyclopropyl carboxylic acid ester which was deprotected under acid conditions to afford (1R,2S)-1-amino-2-vinylcyclopropane carboxylic acid ester hydrochloride (Method C).

Method A

A.1 Preparation of N-Benzyl Imine of Glycine Ethyl Ester

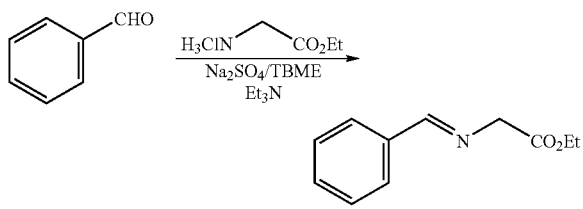

Glycine ethyl ester hydrochloride (303.8 g, 2.16 mole) was suspended in tert-butylmethyl ether (1.6 L). Benzaldehyde (231 g, 2.16 mole) and anhydrous sodium sulfate (154.6 g, 1.09 mole) were added and the mixture cooled to 0° C. using an ice-water bath. Triethylamine (455 mL, 3.26 mole) was added dropwise over 30 min and the mixture stirred for 48 h at rt. The reaction was then quenched by addition of ice-cold water (1 L) and the organic layer was separated. The aqueous phase was extracted with tert-butylmethyl ether (0.5 L) and the combined organic phases washed with a mixture of saturated aqueous $NaHCO_3$ (1 L) and brine (1 L). The solution was dried over $MgSO_4$, concentrated in vacuo to afford 392.4 g of the N-benzyl imine product as a thick yellow oil that was used directly in the next step. $^1$H NMR ($CDCl_3$, 300 MHz) δ 1.32 (t, J=7.1 Hz, 3H), 4.24 (q, J=7.1 Hz, 2H), 4.41 (d, J=1.1 Hz, 2H), 7.39–7.47 (m, 3H), 7.78–7.81 (m, 2H), 8.31 (s, 1H).

A.2 Preparation of racemic N-Boc-(1R,2S)/(1S,2R)-1-amino-2-vinylcyclopropane carboxylic acid ethyl ester

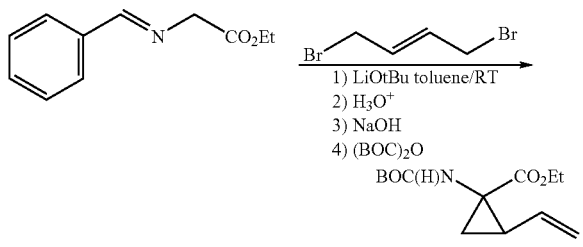

To a suspension of lithium tert-butoxide (84.06 g, 1.05 mol) in dry toluene (1.2 L), was added dropwise a mixture of the N-benzyl imine of glycine ethyl ester (100.4 g, 0.526 mol) and trans-1,4-dibromo-2-butene (107.0 g, 0.500 mol) in dry toluene (0.6 L) over 60 min. After completion of the addition, the deep red mixture was quenched by addition of water (1 L) and tert-butylmethyl ether (TBME, 1 L). The aqueous phase was separated and extracted a second time with TBME (1 L). The organic phases were combined, 1 N HCl (1 L) was added and the mixture stirred at room temperature for 2 h. The organic phase was separated and extracted with water (0.8 L). The aqueous phases were then combined, saturated with salt (700 g), TBME (1 L) was added and the mixture cooled to 0° C. The stirred mixture was then basified to pH 14 by the dropwise addition of 10 N NaOH, the organic layer separated, and the aqueous phase extracted with TBME (2×500 mL). The combined organic extracts were dried ($MgSO_4$) and concentrated to a volume of 1 L. To this solution of free amine, was added $BOC_2O$ or di-tert-butyldicarbonate (131.0 g, 0.6 mol) and the mixture stirred 4 days at rt. Additional di-tert-butyldicarbonate (50 g, 0.23 mol) was added to the reaction, the mixture refluxed for 3 h, and was then allowed cool to room temperature overnight. The reaction mixture was dried over $MgSO_4$ and concentrated in vacuo to afford 80 g of crude material. This residue was purified by flash chromatography (2.5 Kg of $SiO_2$, eluted with 1% to 2% $MeOH/CH_2Cl_2$) to afford 57 g (53%) of racemic N-Boc-(1R,2S)/(1S,2R)-1-amino-2-vinylcyclopropane carboxylic acid ethyl ester as a yellow oil which solidified while sitting in the refrigerator: $^1$H NMR ($CDCl_3$, 300 MHz) δ 1.26 (t, J=7.1 Hz, 3H), 1.46 (s, 9H), 1.43–1.49 (m, 1H), 1.76–1.82 (br m, 1H), 2.14 (q, J=8.6 Hz, 1H), 4.18 (q, J=7.2 Hz, 2H), 5.12 (dd J=10.3, 1.7 Hz, 1H), 5.25 (br s, 1H), 5.29 (dd, J=17.6, 1.7 Hz, 1H), 5.77 (ddd, J=17.6, 10.3, 8.9 Hz, 1H); MS m/z 254.16 (M-1)

A.3 Preparation of Racemic (1R,2S)1(1S,2R) 1-amino-2-vinylcyclopropane carboxylic acid ethyl ester hydrochloride

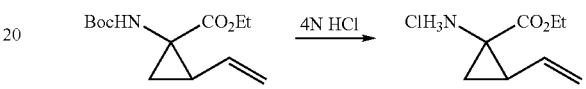

N-Boc-(1R,2S)/(1S,2R)-1-amino-2-vinylcyclopropane carboxylic acid ethyl ester (9.39 g, 36.8 mmol) was dissolved in 4 N HCl/dioxane (90 ml, 360 mmol) and was stirred for 2 h at rt. The reaction mixture was concentrated to supply (1R,2S)/(1S,2R)-1-amino-2-vinylcyclopropane carboxylic acid ethyl ester hydrochloride in quanitative yield (7 g, 100%). $^1$H NMR (methanol-$d_4$) δ 1.32 (t, J=7.1 Hz, 3H), 1.72 (dd, J=10.2, 6.6 Hz, 1H), 1.81 (dd, J=8.3, 6.6 Hz, 1H), 2.38 (q, J=8.3 Hz, 1H), 4.26–4.34 (m, 2H), 5.24 (dd, 10.3, 1.3 Hz, 1H) 5.40 (d, J=17.2 Hz, 1H), 5.69–5.81 (m, 1H).

Method B

Preparation of Racemic (1R,2S)/(1S,2R) 1-amino-2-vinylcyclopropane carboxylic acid ethyl ester hydrochloride

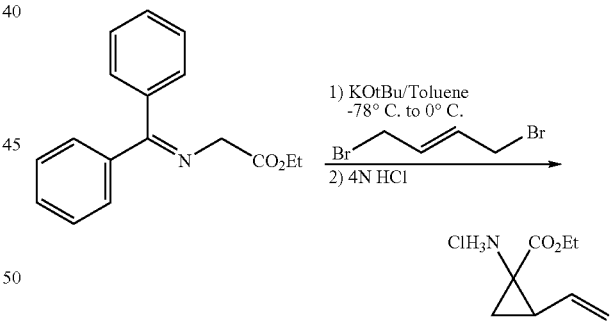

To a solution of potassium tert-butoxide (11.55 g, 102.9 mmol) in THF (450 mL) at -78° C. was added the commercially available N,N-dibenzyl imine of glycine ethyl ester (25.0 g, 93.53 mmol) in THF (112 mL). The reaction mixture was warmed to 0° C., stirred for 40 min, and was then cooled back to -78° C. To this solution was added trans-1,4-dibromo-2-butene (20.0 g, 93.50 mmol), the mixture stirred for 1 h at 0° C. and was cooled back to -78° C. Potassium tert-butoxide (11.55 g, 102.9 mmol) was added, the mixture immediately warmed to 0° C., and was stirred one more hour before concentrating in vacuo. The crude product was taken up in $Et_2O$ (530 mL), 1N aq. HCl solution (106 mL, 106 mmol) added and the resulting biphasic mixture stirred for 3.5 h at rt. The layers were separated and the aqueous layer was washed with Et₂O (2×) and basified with a saturated aq. NaHCO₃ solution. The desired amine was extracted with Et₂O (3×) and the combined organic extract was washed with brine, dried (MgSO₄), and concentrated in vacuo to obtain the free amine. This material was treated with a 4N HCl solution in dioxane (100 mL, 400 mmol) and concentrated to afford (1R,2S)/(1S,2R)-1-amino-2-vinylcyclopropane carboxylic acid ethyl ester hydrochloride as a brown semisolid (5.3 g, 34% yield) identical to the material obtained from procedure A, except for the presence of a small unidentified aromatic impurity (8%).

Method C

Resolution of N-Boc-(1R,2S)/(1S,2R)-1-amino-2-vinylcyclopropane carboxylic acid ethyl ester

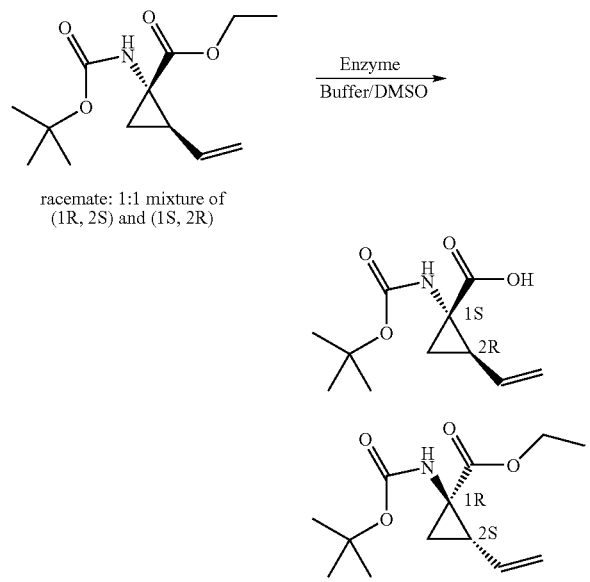

Resolution A

To an aqueous solution of sodium phosphate buffer (0.1 M, 4.25 liter ("L"), pH 8) housed in a 12 Liter jacked reactor, maintained at 39° C., and stirred at 300 rpm was added 511 grams of Acalase 2.4 L (about 425 mL) (Novozymes North America Inc.). When the temperature of the mixture reached 39° C., the pH was adjusted to 8.0 by the addition of a 50% NaOH in water. A solution of the racemic N-Boc-(1R,2S)/(1S,2R)-1-amino-2-vinylcyclopropane carboxylic acid ethyl ester (85 g) in 850 mL of DMSO was then added over a period of 40 min. The reaction temperature was then maintained at 40° C. for 24.5 h during which time the pH of the mixture was adjusted to 8.0 at the 1.5 h and 19.5 h time points using 50% NaOH in water. After 24.5 h, the enantio-excess of the ester was determined to be 97.2%, and the reaction was cooled to room temperature (26° C.) and stirred overnight (16 h) after which the enantio-excess of the ester was determined to be 100%. The pH of the reaction mixture was then adjusted to 8.5 with 50% NaOH and the resulting mixture was extracted with MTBE (2×2 L). The combined MTBE extract was then washed with 5% NaHCO₃ (3×100 mL), water (3×100 mL), and evaporated in vacuo to give the enantiomerically pure N-Boc-(1R,2S)/-1-amino-2-vinylcyclopropane carboxylic acid ethyl ester as light yellow solid (42.55 g; purity: 97% @210 nm, containing no acid; 100% enantiomeric excess ("ee"). The aqueous layer from the extraction process was then acidified to pH 2 with 50% H₂SO₄ and extracted with MTBE (2×2 L). The MTBE extract was washed with water (3×100 mL) and evaporated to give the acid as light yellow solid (42.74 g; purity: 99% @ 210 nm, containing no ester).

NMR observed chemical shift
Solvent: CDCl₃ (proton δ 7.24 ppm, C-13 δ 77.0 ppm)
Bruker DRX-500C: proton 500.032 MHz, carbon 125.746 MHz

| Position | Proton (pattern) ppm | C-13 ppm | Proton (pattern) ppm | C-13 ppm |
|---|---|---|---|---|
| 1 | — | 40.9 | — | 40.7 |
| 2 | 2.10 (q, J = 9.0 Hz) | 34.1 | 2.17 (q, J = 9.0 Hz) | 35.0 |
| 3a | 1.76 (br) | 23.2 | 1.79 (br) | 23.4 |
| 3b | 1.46 (br) | | 1.51,(br) | |
| 4 | — | 170.8 | — | 175.8 |
| 5 | 5.74 (ddd, J = 9.0, 10.0, 17.0 Hz) | 133.7 | 5.75 (m) | 133.4 |
| 6a | 5.25 (d, J = 17.0 Hz) | 117.6 | 5.28 (d, J = 17.0 Hz) | 118.1 |
| 6b | 5.08 (dd, J = 10.0, 1.5 Hz) | | 5.12 (d, J = 10.5 Hz) | |
| 7 | — | 155.8 | — | 156.2 |
| 8 | — | 80.0 | — | 80.6 |
| 9 | 1.43 (s) | 28.3 | 1.43 (s) | 28.3 |
| 10 | 4.16 (m) | 61.3 | — | — |
| 11 | 1.23 (t, J = 7.5 Hz) | 14.2 | — | — |

Resolution B

To 0.5 mL 100 mM Heps•Na buffer (pH 8.5) in a well of a 24 well plate (capacity: 10 mL/well), 0.1 mL of Savinase 16.0 L (protease from *Bacillus clausii*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 h, enantio-excess of the ester was determined to be 44.3% as following: 0.1 mL of the reaction mixture was removed and mixed well with 1 mL ethanol; after centrifugation, 10 microliter ("μl") of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 μl of the supernatant was analyzed with the chiral HPLC and enantio-excess of the ester was determined to be 100%.

Resolution C

To 0.5 ml 100 mM Hep•Na buffer (pH 8.5) in a well of a 24 well plate (capacity: 10 mL/well), 0.1 ml of Esperase 8.0 L, (protease from *Bacillus halodurans*) (Novozymes North America Inc.) and a solution of the racemic N-Boc-(1R,2S)/(1S,2R)-1-amino-2-vinylcyclopropane carboxylic acid ethyl ester (10 mg) in 0.1 mL of DMSO were added. The plate was sealed and incubated at 250 rpm at 40° C. After 18 hour, enantio-excess of the ester was determined to be 39.6% as following: 0.1 mL of the reaction mixture was removed and mixed well with 1 mL ethanol; after cenrifugation, 10 µl of the supernatant was analyzed with the chiral HPLC. To the remaining reaction mixture, 0.1 mL of DMSO was added, and the plate was incubated for additional 3 days at 250 rpm at 40° C., after which four mL of ethanol was added to the well. After centrifugation, 10 µl of the supernatant was analyzed with the chiral HPLC and enantio-excess of the ester was determined to be 100%.

Samples analysis was carried out in the following manner:

1) Sample preparation: About 0.5 ml of the reaction mixture was mixed well with 10 volume of EtOH. After centrifugation, 10 µl of the supernatant was injected onto HPLC column.

2) Conversion determination:
Column: YMC ODS A, 4.6×50 mm, S-5 µm
Solvent: A, 1 millimolar ("mM") HCl in water; B, MeCN
Gradient: 30% B for 1 min; 30% to 45% B over 0.5 min; 45% B for 1.5 min; 45% to 30% B over 0.5 min.
Flow rate: 2 mL/min
UV Detection: 210 nm
Retention time: acid, 1.2 min; ester, 2.8 min.

3) Enantio-excess determination for the ester:
Column: CHIRACEL OD-RH, 4.6×150 mm, S-5 µm
Mobile phase: MeCN/50 mM $HClO_4$ in water (67/33)
Flow rate: 0.75 mL/min.
UV Detection: 210 mn.
Retention time:
(1S,2R) isomer as acid: 5.2 min;
Rcaemate: 18.5 min and 20.0 min;
(1R,2S) isomer as ester: 18.5 min.

II. Preparation of N-Boc-(1R,2S)-1-amino-2-cyclopropylcyclopropane carboxylic acid ethyl ester

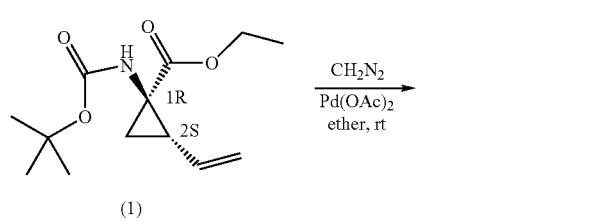

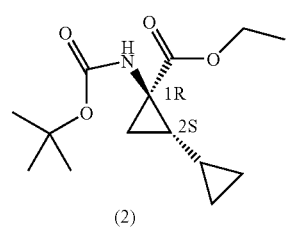

A solution of N-Boc-(1R,2S)-1-amino-2-vinylcyclopropane carboxylic acid (255 mg, 1.0 mmol) in ether (10 mL) was treated with palladium acetate (5 mg, 0.022 mmol). The orange/red solution was placed under an atmosphere of $N_2$. An excess of diazomethane in ether was added dropwise over the course of 1 h. The resulting solution was stirred at rt for 18 h. The excess diazomethane was removed using a stream of nitrogen. The resulting solution was concentrated by rotary evaporation to give the crude product. Flash chromatography (10% EtOAc/hexane) provided 210 mg (78%) of N-Boc-(1R,2S)-1-amino-2-cyclopropylcyclopropane carboxylic acid ethyl ester as a colorless oil. LC-MS (retention time: 2.13, similar to method A except: gradient time 3 min, Xterra MS C18 S7 3.0×50 mm column), MS m/e 270 ($M^+$+1).

III. 1-tert-butoxycarbonylamino-cyclopropane-carboxylic acid is commercially available

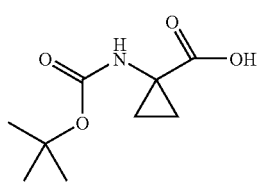

IV. Preparation of 1-aminocyclobutanecarboxylic acid methyl ester hydrochloride

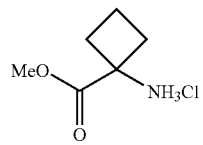

1-aminocyclobutanecarboxylic acid (100 mg, 0.869 mmol)(Tocris) was dissolved in 10 mL of MeOH, HCl gas was bubbled in for 2 h. The reaction mixture was stirred for 18 h, and then concentrated in vacuo to give 144 mg of a yellow oil. Trituration with 10 mL of ether provided 100 mg of the titled product as a white solid. $^1$H NMR ($CDCl_3$) δ 2.10–2.25 (m, 1H), 2.28–2.42 (m, 1H), 2.64–2.82 (m, 4H), 3.87 (s, 3H), 9.21 (br s, 3H).

V. Preparation of racemic (1R,2R)/(1S,2S) 1-Amino-2-ethylcyclopropanecarboxylic acid tert-butyl ester, shown below

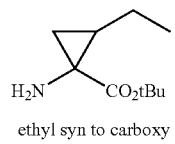

ethyl syn to carboxy

Step 1: Preparation of 2-Ethylcyclopropane-1,1-dicarboxylic acid di-tert-butyl ester, shown below.

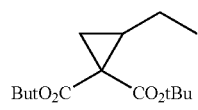

To a suspension of benzyltriethylammonium chloride (21.0 g, 92.2 mmol) in a 50% aqueous NaOH solution (92.4 g in 185 mL H$_2$O) was added 1,2-dibromobutane (30.0 g, 138.9 mmol) and di-tert-butylmalonate (20.0 g, 92.5 mmol). The reaction mixture was vigorously stirred 18 h at rt, a mixture of ice and water was then added. The crude product was extracted with CH$_2$Cl$_2$ (3×) and sequentially washed with water (3×), brine and the organic extracts combined. The organic layer was dried (MgSO$_4$), filtered and concentrated in vacuo. The resulting residue was flash chromatographed (100 g SiO$_2$, 3% Et$_2$O in hexane) to afford the titled product (18.3 g, 67.8 mmol, 73% yield) which was used directly in the next reaction.

Step 2: Preparation of racemic 2-Ethylcyclopropane-1,1-dicarboxylic acid tert-butyl ester, shown below.

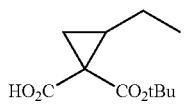

The product of Step 1 (18.3 g, 67.8 mmol) was added to a suspension of potassium tert-butoxide (33.55 g, 299.0 mmol) in dry ether (500 mL) at 0° C., followed by H$_2$0 (1.35 mL, 75.0 mmol) and was vigorously stirred overnight at rt. The reaction mixture was poured in a mixture of ice and water and washed with ether (3×). The aqueous layer was acidified with a 10% aq. citric acid solution at 0° C. and extracted with EtOAc (3×). The combined organic layers were washed with water (2×), brine, dried (MgSO$_4$) and concentrated in vacuo to afford the titled product as a pale yellow oil (10 g, 46.8 mmol, 69% yield).

Step 3: Preparation of (1R,2R)/(1S,2S) 2-Ethyl-1-(2-trimethylsilanylethoxycarbonylamino)cyclopropane-carboxylic acid tert-butyl ester, shown below.

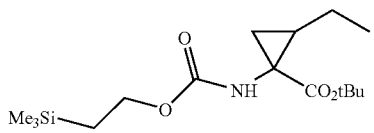

To a suspension, of the product of Step 2 (10 g, 46.8 mmol) and 3 g of freshly activated 4A molecular sieves in dry benzene (160 mL), was added Et$_3$N (7.50 mL, 53.8 mmol) and DPPA (11 mL, 10.21 mmol). The reaction mixture was refluxed for 3.5 h, 2-trimethylsilyl-ethanol (13.5 mL, 94.2 mmol) was then added, and the reaction mixture was refluxed overnite. The reaction mixture was filtered, diluted with Et$_2$O, washed with a 10% aqueous citric acid solution, water, saturated aqueous NaHCO$_3$, water (2×), brine (2×), dried (MgSO$_4$) and concentrated in vacuo. The residue was suspended with 10 g of Aldrich polyisocyanate scavenger resin in 120 mL of CH$_2$Cl$_2$, stirred at rt overnite and filtered to afford the titled product (8 g, 24.3 mmol; 52%) as a pale yellow oil: $^1$H NMR (CDCl$_3$) δ 0.03 (s, 9H), 0.97 (m, 5H), 1.20 (bm, 1H), 1.45 (s, 9H), 1.40–1.70 (m, 4H), 4.16 (m, 2H), 5.30 (bs, 1H).

Step 4: Preparation of racemic (1R,2R)/(1S,2S) 1-Amino-2-ethylcyclopropanecarboxylic acid tert-butyl ester, shown below.

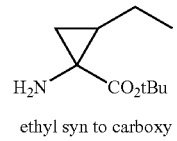

ethyl syn to carboxy

To the product of Step 3 (3 g, 9 mmol) was added a 1.0 M TBAF solution in THF (9.3 mL, 9.3 mmol) and the mixture heated to reflux for 1.5 h, cooled to rt and then diluted with 500 mL of EtOAc. The solution was successively washed with water (2×100 mL), brine (2×100 mL), dried (MgSO$_4$), concentrated in vacuo to provide the title intermediate VI. Preparation of chiral (1R,2S)-1-amino-2-vinylcyclopropane carboxylic acid ethyl ester hydrochloride N-BOC (1R,2S)-1-amino-2-vinylcyclopropanecarboxylic acid ethyl ester (8.5 g, 33.3 mmol) was stirred under an N$_2$ atmosphere with 200 mL of 4N HCl/dioxane (Aldrich) at rt for 3 h. The solvent was removed under reduced pressure keeping the temperature below 40 C. This gave 6.57 g (~100%) of (1R,2S)-1-amino-2-vinylcyclopropanecarboxylic acid ethyl ester hydrochloride as a light tan solid. $^1$H NMR (300 MHz, CD$_3$OD) δ 1.31 (t, J=7.0 Hz, 3H), 1.69–1.82 (m, 2H), 2.38 (q, J=8.8 Hz, 1H), 4.29 (q, J=7.0 Hz, 2H), 5.22 (d, J=10.3 Hz, 1H), 5.40 (d, J=17.2 Hz, 1H), 5.69–5.81 (m, 1H). LC-MS (Method J, retention time: 0.58 min), MS m/z 156 (M$^+$+1).

Example 4

General Procedure for the Preparation of Sulfamides

-continued

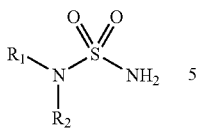

The intermediate sulfamoyl chloride was prepared by addition of water (1 equiv) in THF to a cold (−20° C.) stirred solution of chlorosulfonyl isocyanate (1 equiv) in THF and the resulting solution allowed to warm to 0° C. To this solution was added anhydrous Et$_3$N (1 equiv) followed by requisite secondary amine (1 equiv). The reaction mixture was warmed to room temperature, then filtered and the filtrate was rotary evaporated to afford the desired sulfamides.

Examples 5–18

Preparation of Compounds 1–13.

The key step in the preparation of Compounds 1–13 is the coupling of a tripeptide carboxylic acid and a sulfamide to provide the desired tripeptide sulfamide: The general reaction scheme of this key step is shown below:

Scheme I

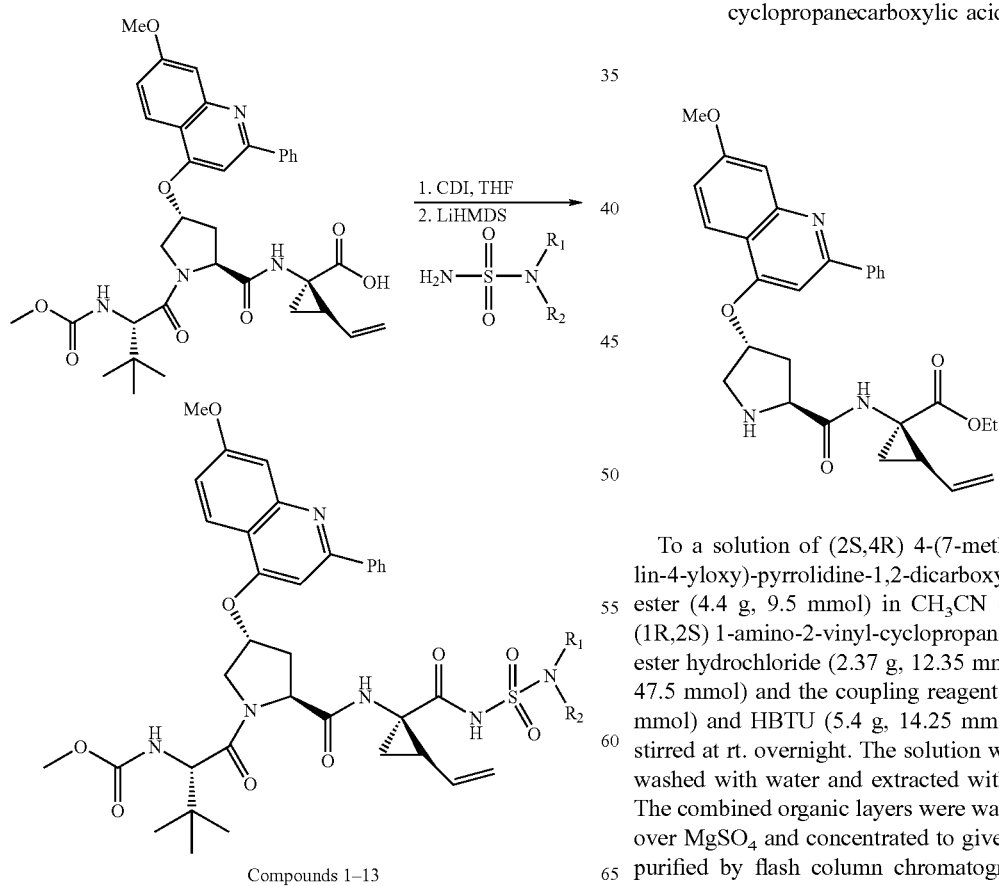

Compounds 1–13

Example 5

Preparation of 1-{[1-(2-Methoxycarbonylamino-3,3-dimethyl-butyryl)-4-(7-methoxy-2-phenyl-quinolin-4-yloxy)-pyrrolidine-2-carbonyl]-amino}-2-vinyl-cyclopropanecarboxylic acid

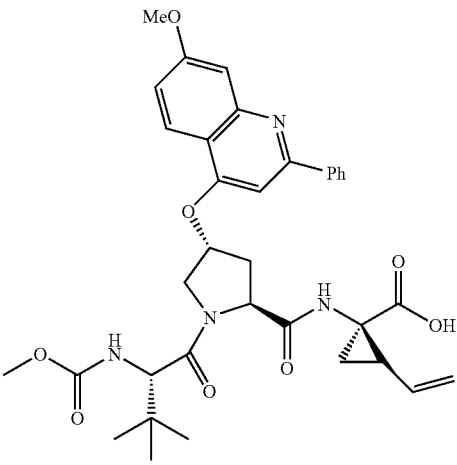

Step 1 of Example 5

Preparation of 1-{[4-(7-Methoxy-2-phenyl-quinolin-4-yloxy)-pyrrolidine-2-carbonyl]-amino}-2-vinyl-cyclopropanecarboxylic acid ethyl ester

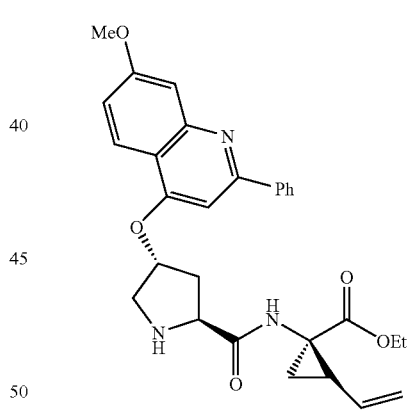

To a solution of (2S,4R) 4-(7-methoxy-2-phenyl-quinolin-4-yloxy)-pyrrolidine-1,2-dicarboxylic acid 1-tert-butyl ester (4.4 g, 9.5 mmol) in CH$_3$CN (100 mL) was added (1R,2S) 1-amino-2-vinyl-cyclopropanecarboxylic acid ethyl ester hydrochloride (2.37 g, 12.35 mmol), DIEA (8.27 mL, 47.5 mmol) and the coupling reagent HOBt (2.18 g, 14.25 mmol) and HBTU (5.4 g, 14.25 mmol). The solution was stirred at rt. overnight. The solution was then concentrated, washed with water and extracted with ethyl acetate twice. The combined organic layers were washed with brine, dried over MgSO$_4$ and concentrated to give yellowish oil. It was purified by flash column chromatography (silica gel, 1:1 EtOAc:Hexanes ) to give yellowish foam as coupling product. Then it was dissolved in 4N HCl in dioxane (20 mL).

The reaction mixture was stirred at rt. for 4 hr. Then it was concentrated and the crude product was further purified by Prep. HPLC to give yellowish solid as TFA salt. (4.5 g, 77% yield). $^1$H NMR (400 MHz, CD$_3$OD) δ1.23 (t, J=7.09 Hz, 3H), 1.46 (dd, J=9.66, 5.50 Hz, 1H), 1.78 (dd, J=8.07, 5.38 Hz, 1H), 2.23 (m, 1H), 2.59 (m, 1H), 2.95 (m, 1H), 3.90–3.99 (m, 2H), 4.05 (s, 3H), 4.14 (q, J=7.09 Hz, 2H), 4.68 (dd, J=10.27, 7.58 Hz, 1H), 4.86(m, 1H), 5.12 (dd, J=10.27, 1.47 Hz, 1H), 5.30 (dd, J=17.00, 1.34 Hz, 1H), 5.76 (m, 1H), 5.96 (s, 1H), 7.45 (dd, J=9.29, 2.45 Hz, 1H), 7.54 (d, J=2.20 Hz, 1H), 7.62 (s, 1H), 7.68–7.77 (m, 3H), 8.05 (m, 2H), 8.38 (d, J=9.29 Hz, 1H). LC-MS (retention time: 1.243 min.), MS m/z 502 (MH$^+$).

Step 2 of Example 5

Preparation of 1-{[1-(2-Methoxycarbonylamino-3,3-dimethyl-butyryl)-4-(7-methoxy-2-phenyl-quinolin-4-yloxy)-pyrrolidine-2-carbonyl]-amino}-2-vinyl-cyclopropanecarboxylic acid ethyl ester

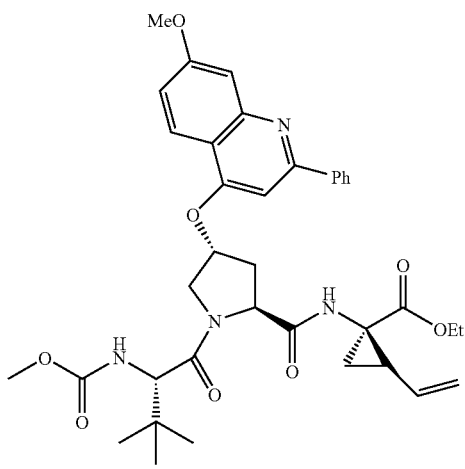

To a solution of 1-{[4-(7-methoxy-2-phenyl-quinolin-4-yloxy)-pyrrolidine-2-carbonyl]-amino}-2-vinyl-cyclopropanecarboxylic acid ethyl ester (600 mg, 1.115 mmol) in CH$_3$CN (20 mL) was 2-methoxycarbonylamino-3,3-dimethyl-butyric acid (317 mg, 1.673 mmol), DIEA (0.97 mL, 5.575 mmol) and the coupling reagent HOBt (256 mg, 1.673 nunol) and HBTU (634 g, 1.673 mmol). The solution was stirred at rt. overnight. Then it was concentrated, washed with water and extracted with ethyl acetate twice. The combined organic layers were washed with brine, dried over MgSO$_4$ and concentrated to give yellowish oil. It was then purified by Prep. HPLC column to give a yellowish oil as product. (410 mg, 47% yield).$^1$H NMR (400 MHz, CD$_3$OD) δ1.03 (s, 9H), 1.22 (t, J=7.09 Hz, 3H), 1.41 (dd, J=9.41, 5.26 Hz, 1H), 1.71 (dd, J=8.19, 5.26 Hz, 1H), 2.17 (m, 1H), 2.50 (m, 1H), 2.77 (m, 1H), 3.33 (s, 3H), 4.03 (s, 3H), 4.04–4.14 (m, 3H), 4.18 (s, 1H), 4.61–4.69 (m, 2H), 4.86 (m, 1H), 5.08 (dd, J=10.27, 1.71 Hz, 1H), 5.25 (d, J=17.11 Hz, 1H), 5.72–5.82 (m, 2H), 7.39 (dd, J=9.29, 2.20 Hz, 1H), 7.51 (m, 1H), 7.63 (m, 1H), 7.69–7.77 (m, 3H), 8.06 (m, 2H), 8.35 (d, J=9.29 Hz, 1H), 8.75 (s, 1H). LC-MS (retention time: 2.857 min.), MS m/z 673 (MH$^+$).

Step 3 of Example 5

Preparation of 1-{[1-(2-Methoxycarbonylamino-3,3-dimethyl-butyryl)-4-(7-methoxy-2-phenyl-quinolin-4-yloxy)-pyrrolidine-2-carbonyl]-amino}-2-vinyl-cyclopropanecarboxylic acid

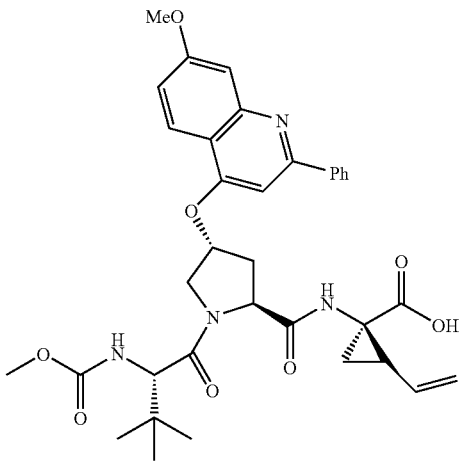

To a solution of 1-{[1-(2-methoxycarbonylamino-3,3-dimethyl-butyryl)-4-(7-methoxy-2-phenyl-quinolin-4-yloxy)-pyrrolidine-2-carbonyl]-amino}-2-vinyl-cyclopropane-carboxylic acid ethyl ester (410 mg, 0. 52 mmol) in THF (20 mL), methanol (11.5 mL) and water (3.8 mL) mixture, lithium hydroxide monohydrate (328 mg, 7.82 mmol) was added. The reaction mixture was stirred at rt for overnight. Then it was acidified with 1N HCl solution and concentrated. The residue was extracted with EtOAc twice and the organic layers were combined. Then it was dried (MgSO$_4$) and concentrated to give an off-white solid. (230 mg, 69% yield). $^1$H NMR (400 MHz, CD$_3$OD) δ 1.02 (s, 9H), 1.43 (dd, J=9.54, 5.14 Hz, 1H), 1.68 (dd, J=8.07, 5.14 Hz, 1H), 2.17 (m, 1H), 2.57 (m, 1H), 2.75 (m, 1H), 3.34 (s, 3H), 4.03 (s, 3H), 4.06 (m, 1H), 4.18 (s, 1H), 4.60–4.70 (m, 2H), 4.88 (m, 1H), 5.08 (dd, J=10.39, 1.59 Hz, 1H), 5.25 (dd, J=17.36, 1.71 Hz, 1H), 5.77–5.87 (m, 2H) 7.38 (dd, J=9.29, 2.20 Hz, 1H), 7.50 (m, 1H), 7.62 (m, 1H), 7.69–7.78 (m, 3H), 8.03–8.07 (m, 2H), 8.36 (d, J=9.20 Hz, 1H). LC-MS (retention time: 2.177 min.), MS m/z 645 (MH$^+$).

Example 6

Preparation of Compound 1:

Compound 1

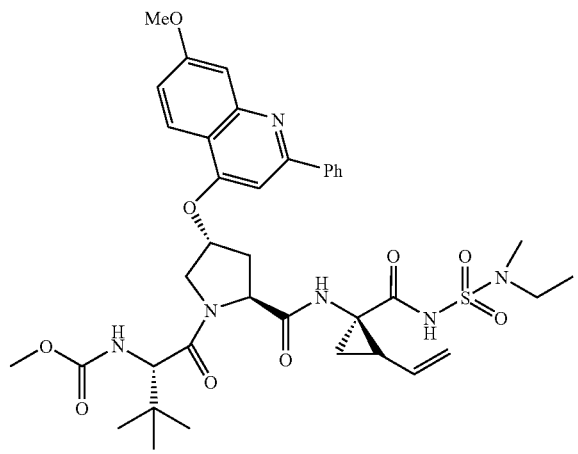

To a solution of 1-{[1-(2-methoxycarbonylamino-3,3-dimethyl-butyryl)-4-(7-methoxy-2-phenyl-quinolin-4-yloxy)-pyrrolidine-2-carbonyl]-amino}-2-vinyl-cyclopropane-carboxylic acid (40 mg, 0.0527 mmol) in THF (5 mL), CDI (12.8 mg, 0.0791 mmol) was added and the reaction mixture was heated under reflux for 45 min. In another round-bottomed flask, LiHMDS (1.0 M solution in hexanes, 0.21 mL, 0.21 mmol) was added to a solution of N-ethyl-methylsulfamide (29 mg, 0.21 mmol) in THF (5 mL) and the reaction mixture was stirred at rt for 1 h. Two reaction mixtures were added together and stirred at rt for 2 h. Water was added to quench the reaction and the reaction solution was extracted with EtOAc. The oraganic layer was separated and dried over MgSO$_4$. Evaporation of solvent gave crude product which was purified by Prep. HPLC to afford desired N-acylsulfamide. (18.4 mg, 40% yield). $^1$H NMR (400 MHz, CD$_3$OD) δ1.03 (s, 9H), 1.14(t, J=7.21 Hz, 3H), 1.37 (dd, J=9.29, 5.38 Hz, 1H), 1.84 (dd, J=8.07, 5.62 Hz, 1H), 2.17 (dd, J=17.36, 8.80 Hz, 1H), 2.40 (m, 1H), 2.72 (m, 1H), 2.87 (s, 3H), 3.20–3.30(m, 2H), 3.36 (s, 3H), 4.04 (s, 3H), 4.11 (dd, J=12.35, 2.81 Hz, 1H), 4.21 (s, 1H), 4.53–4.65 (m, 2H), 4.82 (m, 1H), 5.11 (dd, J=10.15, 1.59 Hz, 1H), 5.26 (d, J=16.87 Hz, 1H), 5.70 (m, 1H), 5.84 (s, br, 1H), 7.41 (dd, J=9.29, 2.20 Hz, 1H), 7.52 (d, J=2.20 Hz, 1H), 7.64 (s, 1H) 7.68–7.80 (m, 3H), 8.03–8.10 (m, 2H), 8.34 (d, J=9.29 Hz, 1H), 9.16 (s, 1H). LC-MS (retention time: 2.333 min.), MS m/z 765 (MH$^+$).

Example 7

Preparation of Compound 2

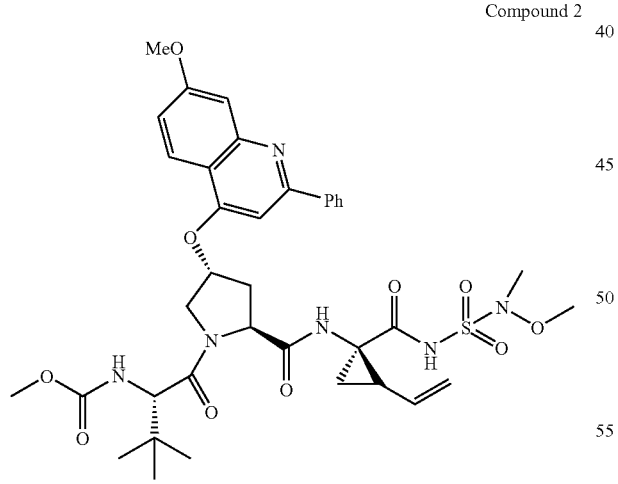

Compound 2

Compound 2 was prepared by the route shown in Scheme 1 of Example 5 and as described for Compound 1 of Example 6. In the case of Compound 2 however, the acylsulfamide employed was synthesized using methoxymethylamine in place of methylethylamine. LC-MS (retention time: 2.070 min.), MS m/z 767 (MH$^+$).

Example 8

Preparation of Compound 3

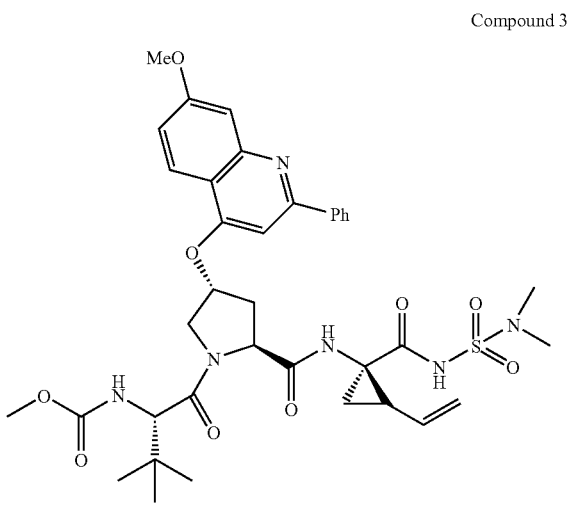

Compound 3

Compound 3 was prepared by the route shown in Scheme 1 of Example 5 and as described for Compound 1 of Example 6. In the case of Compound 3 however, the acylsulfamide employed was synthesized using dimethylamine in place of methylethylamine. LC-MS (retention time: 2.243 min.), MS m/z 751 (MH$^+$).

Example 9

Preparation of Compound 4

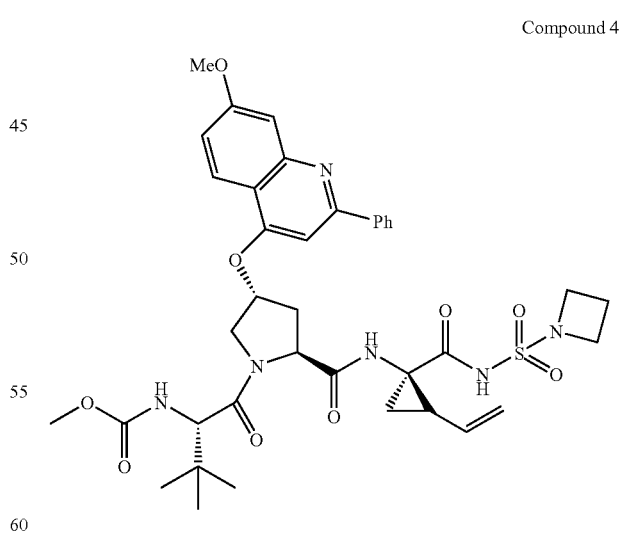

Compound 4

Compound 4 was prepared by the route shown in Scheme 1 of Example 5 and as described for Compound 1 of Example 6. In the case of Compound 4 however, the acylsulfamide employed was synthesized using azetidine in place of methylethylamine. LC-MS (retention time: 2.223 min.), MS m/z 763 (MH$^+$).

Example 10

Preparation of Compound 5

Compound 5

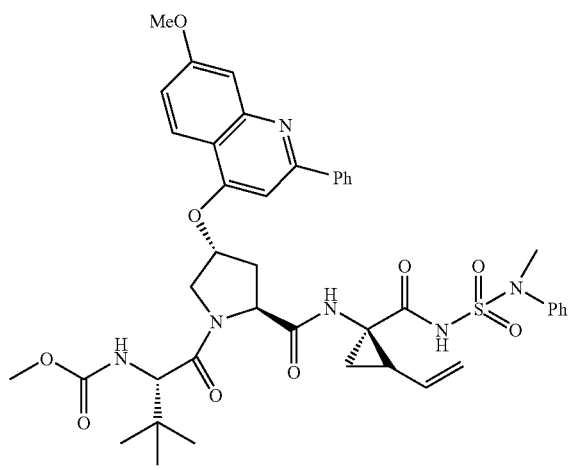

Compound 5 was prepared by the route shown in Scheme 1 of Example 5 and as described for Compound 1 of Example 6. In the case of Compound 5 however, the acylsulfamide employed was synthesized using N-methylaniline in place of methylethylamine. LC-MS (retention time: 2.503 min.), MS m/z 813 (MH$^+$).

Example 11

Preparation of Compound 6

Compound 6

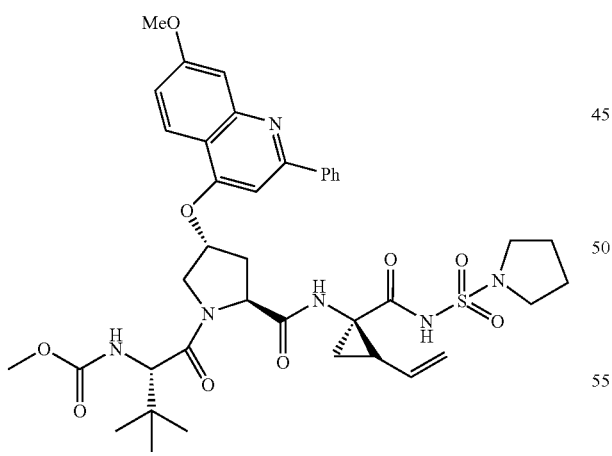

Compound 6 was prepared by the route shown in Scheme 1 of Example 5 and as described for Compound 1 of Example 6. In the case of Compound 6 however, the acylsulfamide employed was synthesized using pyrrolidine place of methylethylamine $^1$H NMR(400 MHz, CD$_3$OD) δ 1.02(s, 9H), 1.37 (dd, J=9.3 Hz, 5.1 Hz, 1H), 1.82–1.90 (m, 5H), 2.19 (m, 1H), 2.40 (m, 1H), 2.74 (m, 1H), 3.31–3.49 (m, 7H), 4.04 (s, 3H), 4.11 (m, 1H), 4.21 (s, 1H), 4.54–4.64 (m, 2H), 4.85 (m, 1H), 5.11(d, J=10.3 Hz, 1H), 5.28 (d, J=17.1 Hz, 1H), 5.69 (m, 1H), 5.84 (s, br, 1H), 7.41 (dd, J=9.3 Hz, 1.9 Hz, 1H), 7.52 (d, J=2.4 Hz, 1H), 7.63 (s, 1H), 7.68–7.77 (m, 3H), 8.06 (m, 2H), 8.34 (d, J=9.3 Hz, 1H). LC-MS (retention time: 2.340 min.), MS m/z 777 (MH$^+$).

Example 12

Preparation of Compound 7

Compound 7

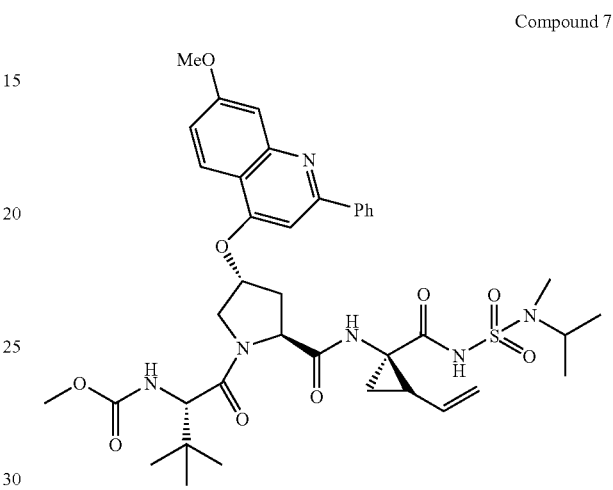

Compound 7 was prepared by the route shown in Scheme 1 of Example 5 and as described for Compound 1 of Example 6. In the case of Compound 7 however, the acylsulfamide employed was synthesized using isopropylmethylamie in place of methylethylamine. LC-MS (retention time: 2.420 min.), MS m/z 779 (MH$^+$).

Example 13

Preparation of Compound 8

Compound 8

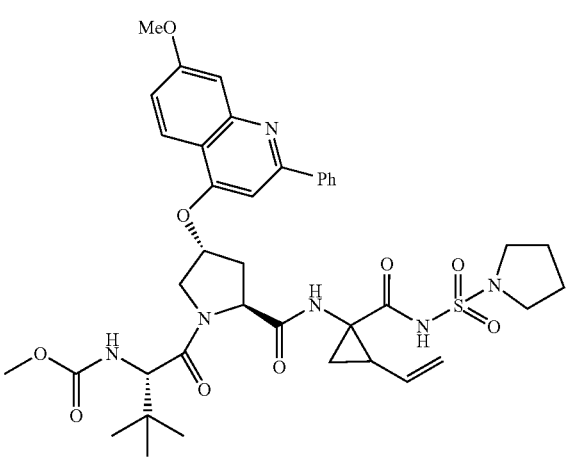

Compound 2 was prepared by the route shown in Scheme 1 of Example 5 and as described for Compound 1 of Example 6. In the case of Compound 8 however, the acylsulfamide employed was synthesized using pyrrolidine in place of methylethylamineand a racemic P1 element. MS m/z 777 (MH+).

Example 14

Preparation of Compound 9

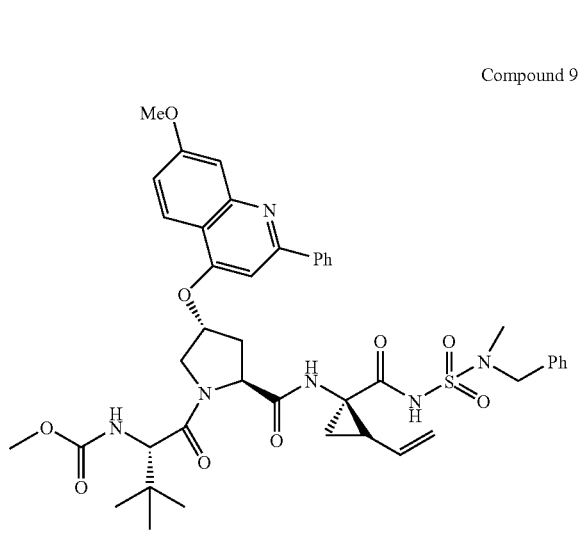

Compound 9

Compound 2 was prepared by the route shown in Scheme 1 of Example 5 and as described for Compound 1 of Example 6. In the case of Compound 9 however, the acylsulfamide employed was synthesized using methylbenzylamine in place of methylethylamine. LC-MS (retention time: 2.430 min.), MS m/z 827 (MH+).

Example 15

Preparation of Compound 10

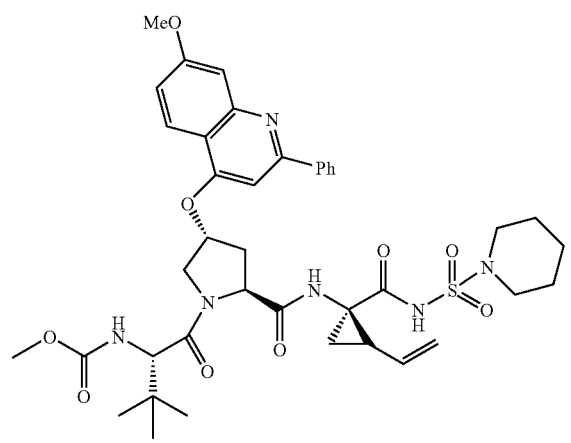

Compound 10

Compound 10 was prepared by the route shown in Scheme 1 of Example 5 and as described for Compound 1 of Example 6. In the case of Compound 10 however, the acylsulfamide employed was synthesized using piperidine in place of methylethylamine. LC-MS (retention time: 2.453 min.), MS m/z 791 (MH+).

Example 16

Preparation of Compound 11

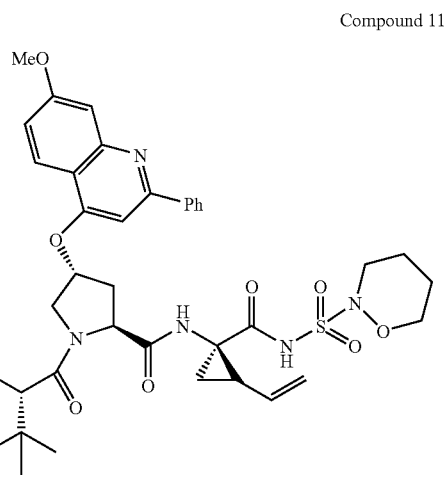

Compound 11

Compound 11 was prepared by the route shown in Scheme 1 of Example 5 and as described for Compound 1 of Example 6. In the case of Compound 11 however, the acylsulfamide employed was synthesized using tetrahydro-2H-1,2-oxazine in place of methylethylamine. LC-MS (retention time: 2.317 min.), MS m/z 793 (MH+).

Example 17

Preparation of Compound 12

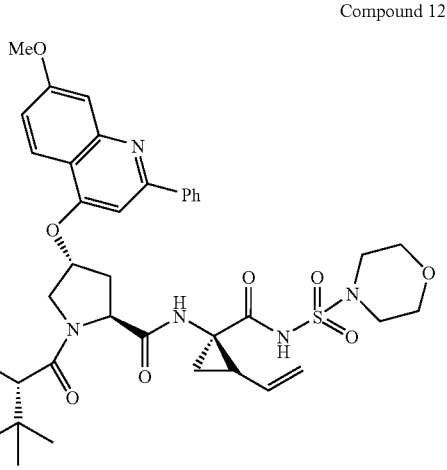

Compound 12

Compound 12 was prepared by the route shown in Scheme 1 of Example 5 and as described for Compound 1 of Example 6. In the case of Compound 12 however, the acylsulfamide employed was synthesized using morpholine in place of methylethylamine. $^1$H NMR(400 MHz, CD$_3$OD) δ 1.02(s, 9H), 1.38 (dd, J=9.1 Hz, 5.6 Hz, 1H), 1.88 (dd, J=8.1 Hz, 5.6 Hz, 1H), 2.21 (m, 1H), 2.40 (m, 1H), 2.75 (m, 1H), 3.36 (s, 3H), 3.66 (m, 4H), 4.04 (s, 3H), 4.10 (dd, J=12.5 Hz, 2.9 Hz, 1H), 4.21 (s, 1H), 4.55–4.65 (m, 2H), 4.85 (m, 5H), 5.15(dd, J=10.3 Hz, 1.5 Hz, 1H), 5.29 (dd, J=17.1 Hz, 1.5 Hz, 1H), 5.70 (m, 1H), 5.83 (s, br, 1H), 7.41 (dd, J=9.3 Hz, 2.2 Hz, 1H), 7.52 (d, J=2.2 Hz, 1H), 7.63 (s, 1H), 7.69–7.79 (m, 3H), 8.07 (m, 2H), 8.34 (d, J=9.3 Hz, 1H). LC-MS (retention time: 2.210 min.), MS m/z 793 (MH$^+$).

Example 18

Preparation of Compound 13

Compound 13

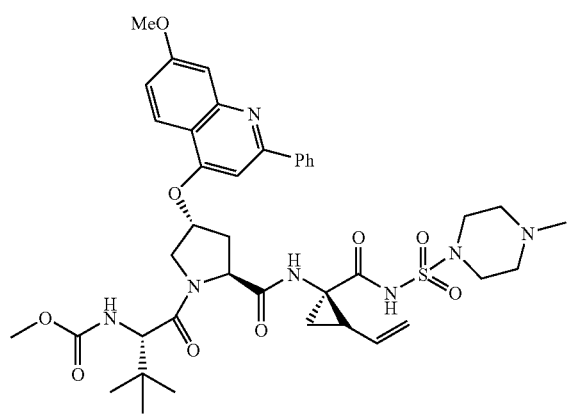

Compound 13 was prepared by the route shown in Scheme 1 of Example 5 and as described for Compound 1 of Example 6. In the case of Compound 13 however, the acylsulfamide employed was synthesized using N-methylpiperizine in place of methylethylamine. LC-MS (retention time: 1.923 min.), MS m/z 806 (MH$^+$).

Examples 19–27

Preparation of Compounds 14–22

Example 19

General scheme for the preparation of Compounds 14–22

Scheme 2

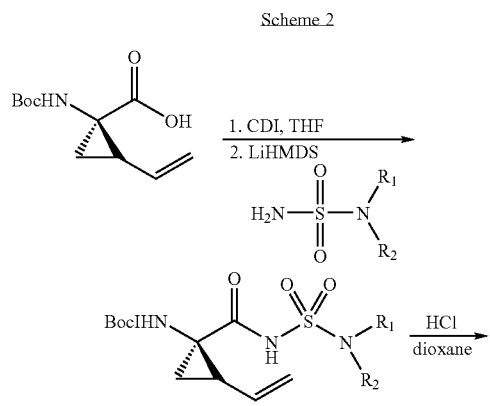

-continued

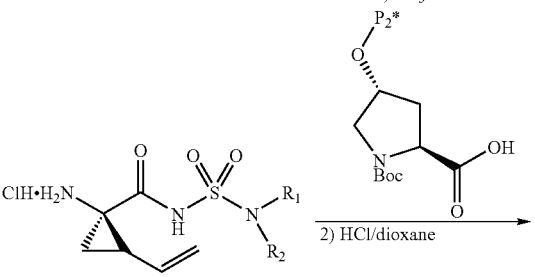

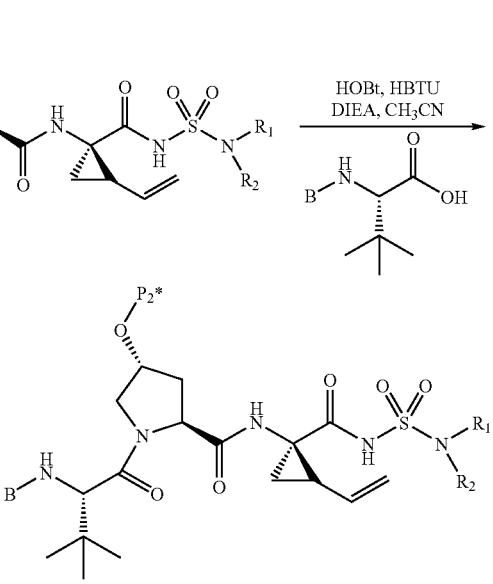

Compound 14

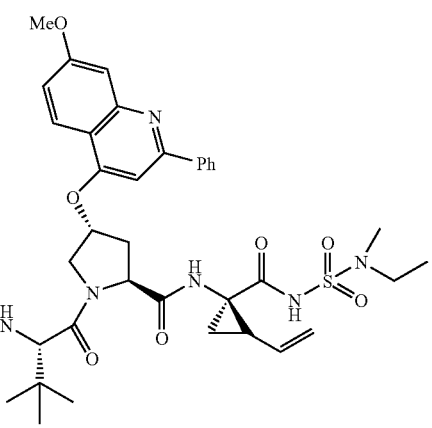

Step 1 of Example 19

To a solution of (1R,2S) 1-tert-butoxycarbonylamino-2-vinyl-cyclopropanecarboxylic acid (217 mg, 1.194 mmol) in THF (5 mL), CDI (290 mg, 1.791 mmol) was added and the reaction mixture was heated under reflux for 45 min. In another round-bottomed flask, LiHMDS (1.0 M solution in hexanes, 2.4 mL, 2.4 mmol) was added to a solution of N-ethylmethylsulfamide (330 mg, 2.388 mmol) in THF (5 mL) and the reaction mixture was stirred at rt for 1 h. Two reaction mixtures were added together and stirred at rt for 2 h. Water was added to quench the reaction and the reaction solution was extracted with EtOAc. The oraganic layer was separated and dried over MgSO$_4$. Evaporation of solvent gave crude product which was purified by Prep. HPLC to afford desired N-acylsulfamide. N-acylsulfamide was then dissolved in 4N HCl solution in dioxane (2 mL) and stirred at rt for 4 h. Evaporation of solution give brownish oil as HCl salt. (112 mg, 33% yield). $^1$H NMR (400 Mz, CD$_3$OD) δ 1.16 (t, J=7.21 Hz, 3H), 1.68 (dd, J=10.03, 7.83 Hz, 1H), 2.15 (m, 1H), 2.37 (m, 1H), 2.89 (s, 3H), 3.30 (m, 2H), 5.31 (d, J=10.27 Hz, 1H), 5.42 (d, J=17.12 Hz, 3H), 5.68 (m, 1H). LC-MS (retention time: 0.883 min.), MS m/z 270 (M+Na$^+$).

Step 2 of Example 19

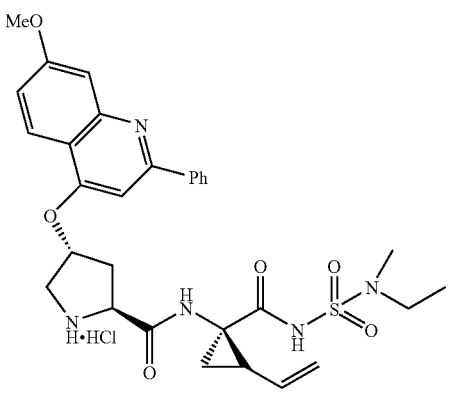

To a solution of (2S,4R)4-(7-methoxy-2-phenyl-quinolin-4-yloxy)-pyrrolidine-1,2-dicarboxylic acid 1-tert-butyl ester (62.5 mg, 0.135 mmol) in CH$_3$CN (10 mL) was added the acylsulfamide-P1-amino acid (42 mg, 0.148 mmol), DIEA (0.12 mL, 0.675 mmol) and the coupling reagent HOBt (31 mg, 0.203 mmol) and HBTU (77 mg, 0.203 mmol). The solution was stirred at rt for overnight. Then it was concentrated, washed with water and extracted with ethyl acetate twice. The combined organic layers were washed with brine, dried over MgSO$_4$ and concentrated to give yellow oil. It was purified by Prep. HPLC column to give a colorless thick oil which was then dissolved in 4N HCl in dioxane (2 mL). The reaction mixture was stirred at rt. for overnight. Evaporation of solvent gave the desired product as a hydrochloride salt (62 mg, yellowish oil, 68% yield). $^1$H NMR (400 MHz, CD$_3$OD) δ 1.14 (t, J=7.21 Hz, 3H), 1.32 (dd, J=9.78, 5.62 Hz, 1H), 1.90 (dd, J=7.58, 5.62 Hz, 1H), 2.31 (m, 1H), 2.51 (m, 1H), 2.86 (s, 3H), 3.06 (m, 1H), 3.20–3.30(m, 2H), 3.56 (m, 1H), 3.72 (m, 2H), 3.96 (m, 1H), 4.06 (s, 3H), 4.80(m, 1H), 5.13 (d, J=10.52 Hz, 1H), 5.29 (d, J=16.87 Hz, 1H), 5.60 (m, 1H), 5.97 (s, 1H), 7.49 (dd, J=9.29, 1.96 Hz, 1H), 7.57 (d, J=1.96 Hz, 1H), 7.63 (s, 1H), 7.68–7.79 (m, 3H), 8.08 (m, 2H), 8.50 (d, J=9.29 Hz, 1H). LC-MS (retention time: 1.810 min.), MS m/z 594 (MH$^+$).

Step 3 of Example 19

Compound 14

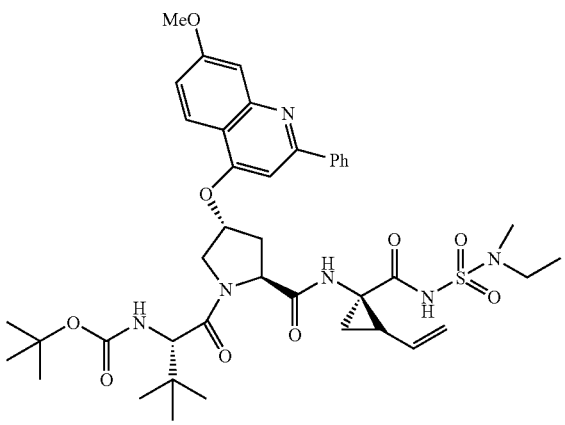

To a solution of dipeptide sulfamide (product of step 2 of Example 19, 14 mg, 0.021 mmol) in CH$_3$CN (5 mL) was added N-boc-L-t-leucine (7.3 mg, 0.0315 mmol), DIEA (0.022 mL, 0.126 mmol) and the coupling reagent HOBt (4.8 mg, 0.0315 mmol) and HBTU (12 mg, 0.0315 mmol). The solution was stirred at rt for overnight. Then it was concentrated, washed with water and extracted with ethyl acetate twice. The combined organic layers were washed with brine, dried over MgSO$_4$ and concentrated to give yellow oil. It was purified by Prep. HPLC column to give a white solid as final product. (9.0 mg, 53% yield). $^1$H NMR (400 MHz, CD$_3$OD) δ 1.02 (s, 9H), 1.13 (t, J=7.09 Hz, 3H), 1.25 (s, 9H), 1.37 (m, 1H), 1.82 (m, 1H), 2.15 (m, 1H), 2.30 (m, 1H), 2.64 (m, 1H), 2.87 (s, 3H), 3.20–3.30(m, 2H), 3.94(s, 3H), 4.07 (m, 1H), 4.25 (m, 1H), 4.47–4.63 (m, 3H), 5.09 (d, J=10.51 Hz, 1H), 5.25 (d, J=17.37 Hz, 1H), 5.56 (s, br, 1H), 5.71 (m, 1H), 6.66 (d, J=9.05 Hz, 1H), 7.07 (m, 1H), 7.24 (s, 1H), 7.38 (d, J=1.96 Hz, 1H), 7.46–7.56 (m, 3H), 8.01–8.09 (m, 3H). LC-MS (retention time: 2.563 min.), MS m/z 807 (MH$^+$).

Example 20

Preparation of Compound 15

Compound 15

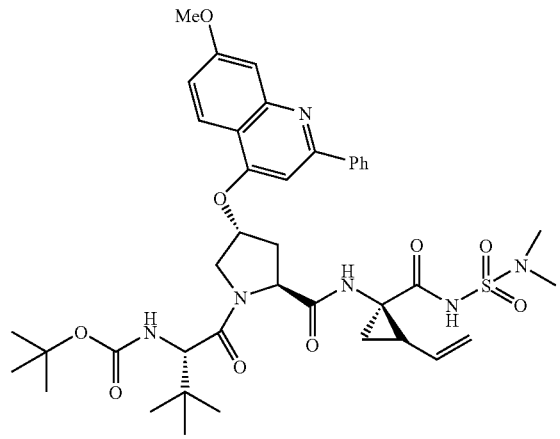

Compound 15 was prepared by the route shown in Scheme 2 of Example 19 and as described for Compound 14 of Example 19. In the case of Compound 15 however, the acylsulfamide employed was synthesized using dimethylamine in place of methylethylamine. LC-MS (retention time: 2.463 min.), MS m/z 793 (MH+).

Example 21

Preparation of Compound 16

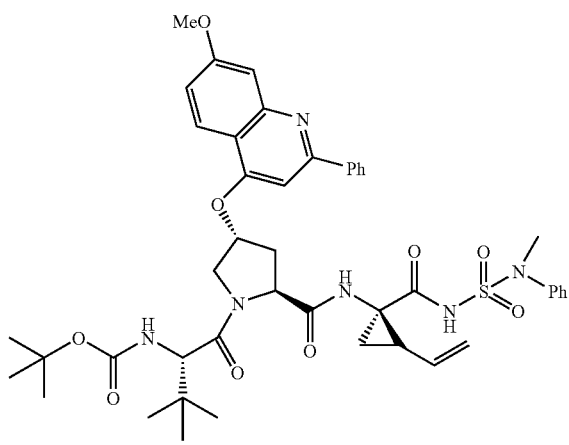

Compound 16

Compound 16 was prepared by the route shown in Scheme 2 of Example 19 and as described for Compound 14 of Example 19. In the case of Compound 16 however, the acylsulfamide employed was synthesized using N-methylaniline in place of methylethylamine. LC-MS (retention time: 2.723 min.), MS m/z 856 (MH+).

Example 22

Preparation of Compound 17

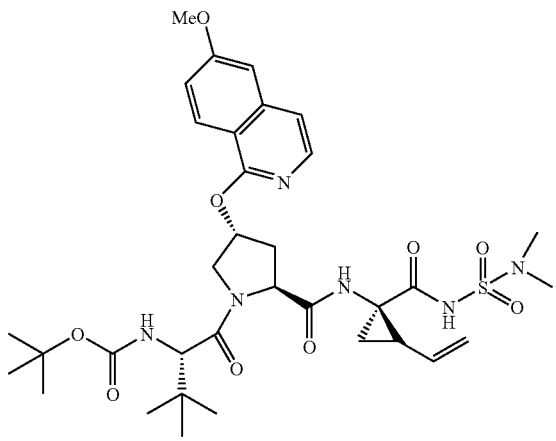

Compound 17

Compound 17 was prepared by the route shown in Scheme 2 of Example 19 and as described for Compound 14 of Example 19. In the case of Compound 17 however, the acylsulfamide employed was synthesized using dimethylamine in place of methylethylamine, and 6-methoxy-1-chloroisoquinoline was used in place of 2-phenyl-4-chloro-7-methoxyquinoline. LC-MS (retention time: 2.807 min.), MS m/z 717 (MH+).

Example 23

Preparation of Compound 18

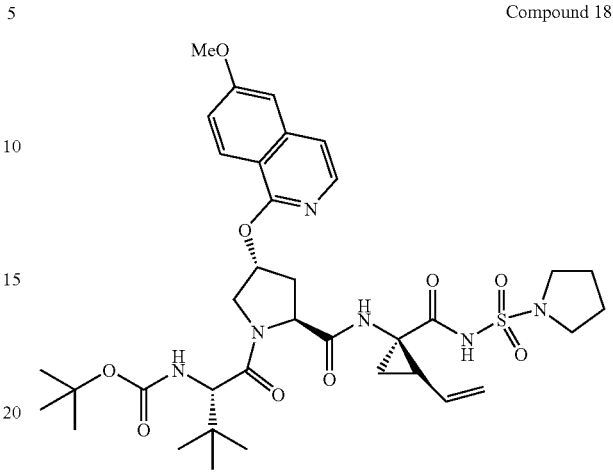

Compound 18

Compound 18 was prepared by the route shown in Scheme 2 of Example 19 and as described for Compound 14 of Example 19. In the case of Compound 18 however, the acylsulfamide employed was synthesized using pyrrolidine in place of methylethylamine, and 6-methoxy-1-chloroisoquinoline was used in place of 2-phenyl-4-chloro-7-methoxyquinoline. LC-MS (retention time: 2.927 min.), MS m/z 743 (MH+).

Example 24

Preparation of Compound 19

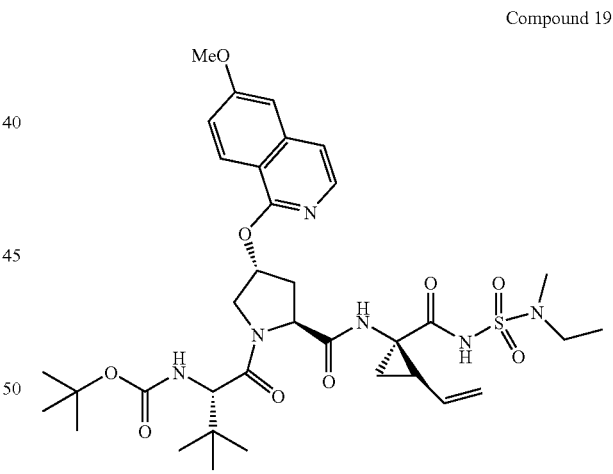

Compound 19

Compound 19 was prepared by the route shown in Scheme 2 of Example 19 and as described for Compound 14 of Example 19. In the case of Compound 19 however, 6-methoxy-1-chloroisoquinoline was used in place of 2-phenyl-4-chloro-7-methoxyquinoline. $^1$H NMR (400 MHz, CD$_3$OD) δ 1.02 (s, 9H), 1.14 (t, J=7.21 Hz, 3H), 1.25 (s, 9H), 1.37 (m, 1H), 1.81 (m, 1H), 2.13–2.30(m, 2H), 2.57 (m, 1H), 2.87 (s, 3H), 3.20–3.30(m, 2H), 3.90 (s, 3H), 4.04(m, 1H), 4.23 (m, 1H), 4.42 (d, J=12.22 Hz, 1H), 4.46–4.60(m, 2H), 5.11 (d, J=10.27 Hz, 1H), 5.29 (d, J=16.87 Hz, 1H), 5.70 (m, 1H), 5.81 (s, br, 1H), 6.60 (d, J=8.56 Hz, 1H), 7.08 (d, J=8.07 Hz, 1H), 7.16 (d, J=2.45 Hz, 1H), 7.23 (d, J=5.87 Hz, 1H), 7.87 (d, J=5.87 Hz, 1H), 8.06 (d, J=9.05 Hz, 1H). LC-MS (retention time: 2.910 min.), MS m/z 731 (MH+).

Example 25

Preparation of Compound 20

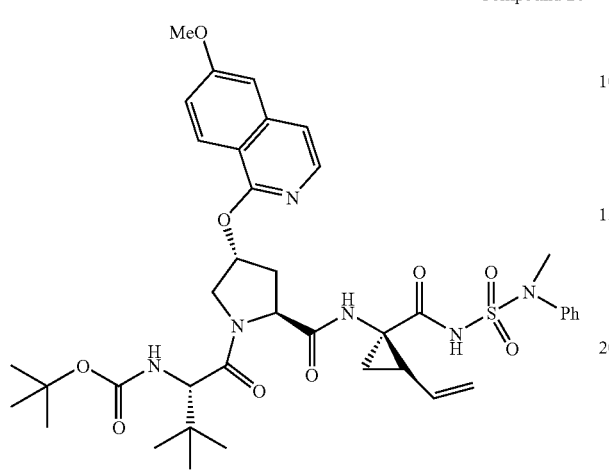

Compound 20

Compound 20 was prepared by the route shown in Scheme 2 of Example 19 and as described for Compound 14 of Example 19. In the case of Compound 20 however, the acylsulfamide employed was synthesized using N-methylaniline in place of methylethylamine, and 6-methoxy-1-chloroisoquinoline was used in place of 2-phenyl-4-chloro-7-methoxyquinoline. $^1$H NMR (400 MHz, CD$_3$OD) δ 0.95 (s, 9H), 1.26 (s, 9H), 1.41 (m, 1H), 1.87 (m, 1H), 2.12–2.25 (m, 2H), 2.50 (dd, J=13.94, 7.09 Hz, 1H), 3.39 (s, 3H), 3.89 (s, 3H), 4.02 (m, 1H), 4.19 (d, J=9.29 Hz, 1H), 4.31–4.47 (m, 2H), 4.57 (s, 1H), 5.17 (d, J=10.27 Hz, 1H), 5.31 (d, J=16.63 Hz, 1H), 5.73–5.90 (m, 2H), 6.56 (d, J=9.29 Hz, 1H), 7.04 (d, J=8.56 Hz, 1H), 7.15 (d, J=1.96 Hz, 1H), 7.22 (d, J=5.87 Hz, 1H), 7.24–7.40 (m, 5H), 7.86 (d, J=5.87 Hz, 1H), 8.03 (d, J=9.05 Hz, 1H). LC-MS (retention time: 3.017 min.), MS m/z 779 (MH$^+$).

Example 26

Preparation of Compound 21

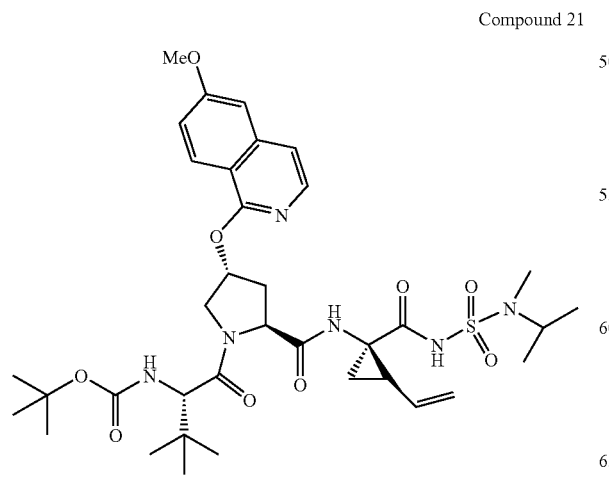

Compound 21

Compound 21 was prepared by the route shown in Scheme 2 of Example 19 and as described for Compound 14 of Example 19. In the case of Compound 21 however, the acylsulfamide employed was synthesized using methylisopropylamine in place of methylethylamine, and 6-methoxy-1-chloroisoquinoline was used in place of 2-phenyl-4-chloro-7-methoxyquinoline. LC-MS (retention time: 2.963 min.), MS m/z 768 (M+Na$^+$).

Example 27

Preparation of Compound 22

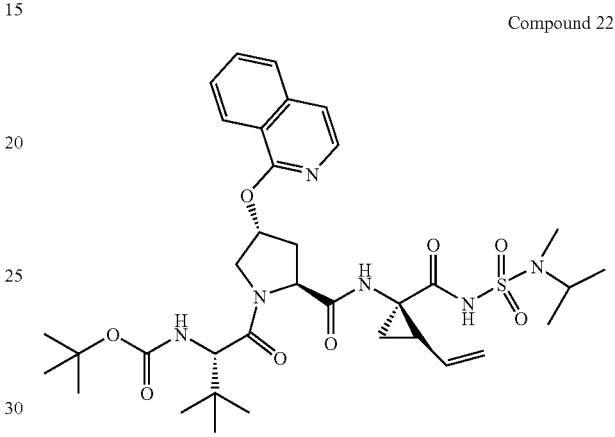

Compound 22

Compound 22 was prepared by the route shown in Scheme 2 of Example 19 and as described for Compound 14 of Example 19. In the case of Compound 22 however, the acylsulfamide employed was synthesized using methylisopropylamine in place of methylethylamine, and 1-chloroisoquinoline was used in place of 2-phenyl-4-chloro-7-methoxyquinolin LC-MS (retention time: 2.993 min.), MS m/z 737 (M+Na$^+$).

Example 28

Compound 23

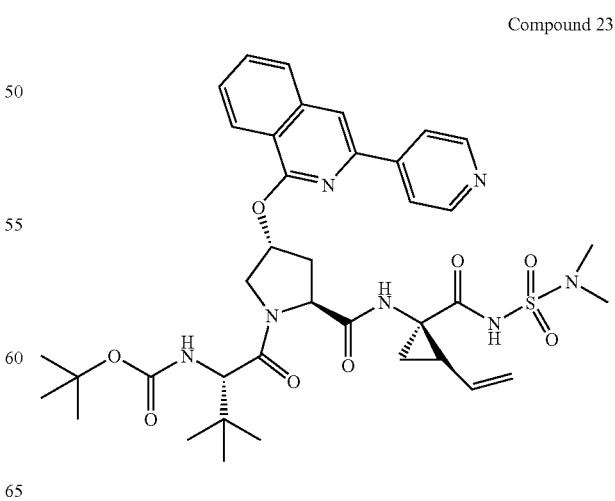

Compound 23

Compound 23 can be prepared by synthesis methods such as described herein.

Example 29

Biological Studies

Recombinant HCV NS3/4A protease complex
FRET peptide assay

The purpose of this in vitro assay was to measure the inhibition of HCV NS3 protease complexes, derived from the BMS strain, H77 strain or J416S strain, as described below, by compounds of the present invention. This assay provides an indication of how effective compounds of the present invention would be in inhibiting HCV proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, J. Clin. Microbiol., 31(6), 1493–1503 (1993)). The amino acid sequence of the nonstructural region, NS2–5B, was shown to be >97% identical to HCV genotype 1a (H77) and 87% identical to genotype 1b (J4L6S). The infectious clones, H77 (1a genotype) and J4L6S (1b genotype) were obtained from R. Purcell (NIH) and the sequences are published in Genbank (AAB67036, see Yanagi, M., Purcell, R. H., Emerson, S. U. and Bukh, J. Proc. Natl. Acad. Sci. U.S.A. 94(16), 8738–8743 (1997); AF054247, see Yanagi, M., St Claire, M., Shapiro, M., Emerson, S. U., Purcell, R. H. and Bukh, J, Virology 244 (1), 161–172. (1998)).

The H77 and J4L6S strains were used for production of recombinant NS3/4A protease complexes. DNA encoding the recombinant HCV NS3/4A protease complex (amino acids 1027 to 1711) for these strains were manipulated as described by P. Gallinari et al. (see Gallinari P, Paolini C, Brennan D, Nardi C, Steinkuhler C, De Francesco R. Biochemistry. 38(17):5620–32, (1999)). Briefly, a three-lysine solubilizing tail was added at the 3'-end of the NS4A coding region. The cysteine in the P1 position of the NS4A–NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen) and the NS3/4A complex was expressed in *Escherichia. coli* strain BL21 (DE3) (Invitrogen) following the protocol described by P. Gallinari et al. (see Gallinari P, Brennan D, Nardi C, Brunetti M, Tomei L, Steinkuhler C, De Francesco R., J Virol. 72(8):6758–69 (1998)) with modifications. Briefly, the NS3/4A protease complex expression was induced with 0.5 millimolar (mM) Isopropyl β-D-1-thiogalactopyranoside (IPTG) for 22 hours (h) at 20° C. A typical fermentation (1 Liter (L)) yielded approximately 10 grams (g) of wet cell paste. The cells were resuspended in lysis buffer (10 mL/g) consisting of 25 mM N-(2-Hydroxyethyl)Piperazine-N'-(2-Ethane Sulfonic acid) (HEPES), pH 7.5, 20% glycerol, 500 mM Sodium Chloride (NaCl), 0.5% Triton X-100, 1 microgram/milliliter ("µg/mL") lysozyme, 5 mM Magnesium Chloride ($MgCl_2$), 1 µg/ml DnaseI, 5 mM β-Mercaptoethanol (βME), Protease inhibitor—Ethylenediamine Tetraacetic acid (EDTA) free (Roche), homogenized and incubated for 20 minutes (min) at 4° C. The homogenate was sonicated and clarified by ultra-centrifugation at 235000 g for 1 h at 4° C. Imidazole was added to the supernatant to a final concentration of 15 mM and the pH adjusted to 8.0. The crude protein extract was loaded on a Nickel—Nitrilotriacetic acid (Ni-NTA) column pre-equilibrated with buffer B (25 mM HEPES, pH 8.0, 20% glycerol, 500 mM NaCl, 0.5% Triton X-100, 15 mM imidazole, 5 mM βME). The sample was loaded at a flow rate of 1 mL/min. The column was washed with 15 column volumes of buffer C (same as buffer B except with 0.2% Triton X-100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton x-100, 10 mM βME). Sample was loaded at a flow rate of 1 mL/min. NS3/4A protease complex-containing fractions were pooled and concentrated to approximately 0.5 mg/ml. The purity of the NS3/4A protease complexes, derived from the BMS, H77 and J4L6S strains, were judged to be greater than 90% by SDS-PAGE and mass spectrometry analyses.

The enzyme was stored at −80° C., thawed on ice and diluted prior to use in assay buffer. The substrate used for the NS3/4A protease assay was RET S1 (Resonance Energy Transfer Depsipeptide Substrate; AnaSpec, Inc. cat # 22991) (FRET peptide), described by Taliani et al. in Anal. Biochem. 240(2):60–67 (1996). The sequence of this peptide is loosely based on the NS4A/NS4B natural cleavage site for the HCV NS3 protease except there is an ester linkage rather than an amide bond at the cleavage site. The peptide substrate was incubated with one of the three recombinant NS3/4A protease complexes, in the absence or presence of a compound of the present invention, and the formation of fluorescent reaction product was followed in real time using a Cytofluor Series 4000.

The reagents were as follow: HEPES and Glycerol (Ultrapure) were obtained from GIBCO-BRL. Dimethyl Sulfoxide (DMSO) was obtained from Sigma. β-Mercaptoethanol was obtained from Bio Rad.

Assay buffer: 50 mM HEPES, pH 7.5; 0.15 M NaCl; 0.1% Triton; 15% Glycerol;10 mM βME. Substrate: 2 µM final concentration (from a 2 mM stock solution in DMSO stored at −20° C.). HCV NS3/4A protease type 1a (1b), 2–3 nM final concentration (from a 5 µM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 µg/ml Bovine Serum Albumin (Sigma) to the assay buffer and reducing the end protease concentration to 300 pM.

The assay was performed in a 96-well polystyrene black plate from Falcon. Each well contained 25 µl NS3/4A protease complex in assay buffer, 50 µl of a compound of the present invention in 10% DMSO/assay buffer and 25 µl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 min.

The percent inhibition was calculated with the following equation:

$$100-[(\delta F_{inh}/\delta F_{con}) \times 100]$$

where δF is the change in fluorescence over the linear range of the curve. A non-linear curve fit was applied to the inhibition-concentration data, and the 50% effective concentration ($IC_{50}$) was calculated by the use of Excel Xl-fit software using the equation, $y=A+((B-A)/(1+((C/x)^D)))$.

All of the compounds tested were found to inhibit the activity of the NS3/4A protease complex with IC50's of 1.2 µM or less. Further, compounds of the present invention, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the in vitro selectivity of the compounds of the present invention in inhibiting HCV NS3/4A protease complex as compared to other serine or cysteine proteases.

The specificities of compounds of the present invention were determined against a variety of serine proteases: human neutrophil elastase (HNE), porcine pancreatic elastase (PPE) and human pancreatic chymotrypsin and one cysteine protease: human liver cathepsin B. In all cases a 96-well plate format protocol using colorimetric p-nitroaniline (pNA) substrate specific for each enzyme was used as described previously (PCT Patent Application No. WO 00/09543) with some modifications to the serine protease assays. All enzymes were purchased from Sigma while the substrates were from Bachem.

Each assay included a 2 h enzyme-inhibitor pre-incubation at room temperature followed by addition of substrate and hydrolysis to ~30% conversion as measured on a Spectramax Pro microplate reader. Compound concentrations varied from 100 to 0.4 µM depending on their potency.

The final conditions for each assay were as follows:

50 mM Tris(hydroxymethyl)aminomethane hydrochloride (Tris-HCl) pH 8, 0.5 M Sodium Sulfate ($Na_2SO_4$), 50 mM NaCl, 0.1 mM EDTA, 3% DMSO, 0.01% Tween-20 with:

133 µM succ-AAA-pNA and 20 nM HNE or 8 nM PPE; 100 µM succ-AAPF-pNA and 250 pM Chymotrypsin.

100 mM $NaHPO_4$ (Sodium Hydrogen Phosphate) pH 6, 0.1 mM EDTA, 3% DMSO, 1 mM TCEP (Tris(2-carboxyethyl)phosphine hydrochloride), 0.01% Tween-20, 30 µM Z-FR-pNA and 5 nM Cathepsin B (enzyme stock activated in buffer containing 20 mM TCEP before use).

The percentage of inhibition was calculated using the formula:

$$[1-((UV_{inh}-UV_{blank})/(UV_{ctl}-UV_{blank}))] \times 100$$

A non-linear curve fit was applied to the inhibition-concentration data, and the 50% effective concentration ($IC_{50}$) was calculated by the use of Excel Xl-fit software.

HCV Replicon Cell-based Assay

An HCV replicon whole cell system was established as described by Lohmann V, Korner F, Koch J, Herian U, Theilmann L, Bartenschlager R., Science 285(5424):110-3 (1999). This system enabled us to evaluate the effects of our HCV Protease compounds on HCV RNA replication. Briefly, using the HCV strain 1b sequence described in the Lohmann paper (Assession number:AJ238799), an HCV cDNA was generated encoding the 5' internal ribosome entry site (IRES), the neomycin resistance gene, the EMCV (encephalomyocarditis viurs)-IRES and the HCV nonstructural proteins, NS3–NS5B, and 3' non-translated region (NTR). In vitro transcripts of the cDNA were transfected into the human hepatoma cell line, Huh7. Selection for cells constitutively expressing the HCV replicon was achieved in the presence of the selectable marker, neomycin (G418). Resulting cell lines were characterized for positive and negative strand RNA production and protein production over time.

Huh7 cells, constitutively expressing the HCV replicon, were grown in Dulbecco's Modified Eagle Media (DMEM) containing 10% Fetal calf serum (FCS) and 1 mg/ml G418 (Gibco-BRL). Cells were seeded the night before ($1.5 \times 10^4$ cells/well) in 96-well tissue-culture sterile plates. Compound and no compound controls were prepared in DMEM containing 4% FCS, 1:100 Penicillin/Streptomysin, 1:100 L-glutamine and 5% DMSO in the dilution plate (0.5% DMSO final concentration in the assay). Compound/DMSO mixes were added to the cells and incubated for 4 days at 37° C. After 4 days, plates were rinsed thoroughly with Phosphate-Buffered Saline (PBS) (3 times 150 µl). The cells were lysed with 25 µl of a lysis assay reagent containing the FRET peptide (RET S1, as described for the in vitro enzyme assay). The lysis assay reagent was made from 5× cell Luciferase cell culture lysis reagent (Promega #E153A) diluted to 1× with distilled water, NaCl added to 150 mM final, the FRET peptide diluted to 10 µM final from a 2 mM stock in 100% DMSO. The plate was then placed into the Cytofluor 4000 instrument which had been set to 340 nm excitation/490 nm emission, automatic mode for 21 cycles and the plate read in a kinetic mode. $EC_{50}$ determinations were carried out as described for the $IC_{50}$ determinations.

Two different secondary assays were used to confirm $EC_{50}$ determinations from the replicon FRET assay. These included a quantitative RNA assay and a transient luciferase cell reporter assay. For the quantitative RNA assay, compound/no compound controls were incubated with the cells as described for the replicon FRET assay. After 4 days, cells were lyzed using the Rneasy kit (Qiagen). Purified total RNA was normalized using RiboGreen (Jones L J, Yue S T, Cheung C Y, Singer V L, Anal. Chem., 265(2):368–74 (1998)) and relative quantitation of HCV RNA expression assessed using the Taqman procedure (Kolykhalov A A, Mihalik K, Feinstone S M, Rice C M, Journal of Virology 74, 2046–2051 (2000)) and the Platinum Quantitative RT-PCR Thermoscript One-Step kit (Invitrogen cat # 11731-015). Briefly, RNA made to a volume of 5 µl (≦1 ng) was added to a 20 µl Ready-Mix containing the following: 1.25× Thermoscript reaction mix (containing Magnesium Sulfate and 2-deoxynucleoside 5'-triphosphates (dNTPs)), 3 mM dNTPs, 200 nM forward primer (sequence: 5'-gggagagccatagtggtctgc-3'), 600 nM reverse primer (5'-cccaaatctccaggcattga-3'), 100 nM probe (5'-6-FAM-cggaattgccaggacgaccgg-BHQ-1-3')(FAM: Fluorescein-aminohexyl amidite; BHQ: Black Hole Quencher), 1 µM Rox reference dye (Invitrogen cat # 12223-012) and Thermoscript Plus Platinum Taq polymerase mixture. All primers were designed with ABI Prism 7700 software and obtained from Biosearch Technologies, Novato, Calif. Samples containing known concentrations of HCV RNA transcript were run as standards. Using the following cycling protocol (50° C., 30 min; 95° C., 5 min; 40 cycles of 95° C., 15 seconds (s), 60° C., 1 min), HCV RNA expression was quantitated as described in the Perkin Elmer manual using the ABI Prism 7700 Sequence Detector.

The luciferase reporter assay was also used to confirm compound potency in the replicon. Utilization of a replicon luciferase reporter assay was first described by Krieger et al (Krieger N, Lohmann V, and Bartenschlager R, J. Virol. 75(10):4614–4624 (2001)). The replicon construct described for our FRET assay was modified by replacing the resistance gene neomycin with the Blasticidin-resistance gene fused to the N-terminus of the humanized form of *Renilla* luciferase (restriction sites Asc1/Pme1 used for the subcloning). The adaptive mutation at position 1179 (serine to isoleucine) was also introduced (Blight K J, Kolykhalov, A A, Rice, C M, Science 290(5498): 1972–1974). The luciferase reporter assay was set up by seeding huh7 cells the night before at a density of $2 \times 10^6$ cells per T75 flask. Cells were washed the next day with 7.5 ml Opti-MEM. Following the Invitrogen protocol, 40 µl DMRIE-C was vortexed with 5 ml Opti-MEM before adding 5 µg HCV reporter replicon RNA. The mix was added to the washed huh7 cells and left for 4 h at 37° C. In the mean time, serial compound dilutions and no compound controls were prepared in DMEM containing 10% FCS and 5% DMSO in the dilution plate (0.5% DMSO final concentration in the assay). Compound/DMSO mixes were added to each well of a 24-well plate. After 4 h, the transfection mix was aspirated, and cells washed with 5 ml of Opti-MEM before trypsinization. Trypsinized cells were resuspended in 10% DMEM and seeded at $2 \times 10^4$ cells/well in the 24-well plates containing compound or no compound controls. Plates were incubated for 4 days. After 4 days, media was removed and cells washed with PBS. 100 µl 1×*Renilla* Luciferase Lysis Buffer (Promega) was immediately added to each well and the plates either frozen at −80° C. for later analysis, or assayed after 15 min of lysis. Lysate (40 µl) from each well was transferred to a 96-well black plate (clear bottom) followed by 200 µl 1×Renilla Luciferase assay substrate. Plates were read immediately on a Packard TopCount NXT using a luminescence program.

The percentage inhibition was calculated using the formula below:

$$\% \text{ control} = \frac{\text{average luciferase signal in experimental wells (+ compound)}}{\text{average luciferase signal in DMSO control wells (− compound)}}$$

The values were graphed and analyzed using XLFit to obtain the $EC_{50}$ value.

Biological Examples

Representative compounds of the invention were assessed in the HCV replicon cell assay described above and/or in several of the outlined specificity assays described above. For example, Compound 9 was found to have an $IC_{50}$ of 128 nM against the BMS strain of the NS3/4A protease complex in the enzyme assay described above. Similar potency values were obtained with the published H77 ($IC_{50}$ of 62 nM) and J4L6S ($IC_{50}$ of 41 nM) strains. The $EC_{50}$ value in the replicon assay was 403 nM. In the specificity assays, Compound 9 was found to have the following activity: HNE=46 µM; PPE>200 µM; Chymotrypsin>200 µM; Cathepsin B>50 µM (assay interference at higher concentrations). These results indicate this family of compounds are highly specific for the NS3 protease and have utility for inhibiting HCV replicon replication.

The compounds inhibited below were tested for biological activity according to the HCV replican cell assay described above and were found to have activities set forth in Table 2 below. The activity ranges were classified into the following groups: for $IC_{50}$, and $EC_{50}$, A (least active)>1.5 µM; B 0.15–1.5 µM; C (most active) <0.15 µM. Preferably, the $IC_{50}$ values are from about 0.001–1 µM, and most preferably less than 0.1 µM. Preferably, the $EC_{50}$ values are from about 0.001 to 25 µM, more preferably from about 0.001–1 µM and most preferably less than about 0.1 µM.

| Cmpd | Activity Range IC50 | Activity Range EC50 |
|---|---|---|
| 1 | C | C |
| 2 | C | B |
| 3 | C | C |
| 4 | C | B |
| 5 | C | C |
| 6 | C | B |
| 7 | C | B |
| 8 | C | B |
| 9 | C | B |
| 10 | C | B |
| 11 | B | A |
| 12 | B | |
| 13 | B | A |
| 14 | C | C |
| 15 | C | C |
| 16 | C | C |
| 17 | C | B |
| 18 | C | C |
| 19 | C | C |
| 20 | C | C |
| 21 | B | B |
| 22 | B | |
| 23 | C | C |

Although the invention has been described with respect to specific aspects, those skilled in the art will recognize that other aspects are intended to be included within the scope of the claims which follow. Further, the disclosures of documents referenced herein, e.g., U.S. Pat. No. 6,323,180 and U.S. Patent Application Publication No. 20020111313, are incorporated herein, in their entirety, by reference.

What is claim is:

1. A compound having the formula

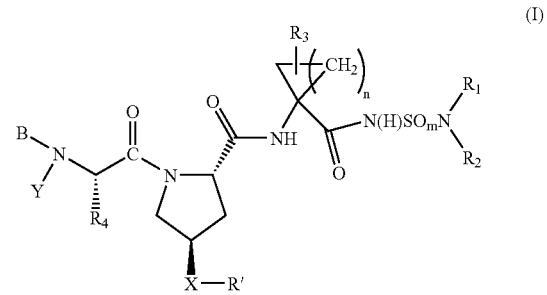

wherein:

(a) $R_1$ and $R_2$ are each independently $C_{1-8}$ alkyl, $C_{3-7}$ cycloalkyl $C_{4-10}$ alkylcycloalkyl, $C_{1-6}$ alkoxy, $C_{6-10}$ aryl, $C_{7-14}$ alkylaryl, $C_{9-14}$ cycloalkylaryl, $C_{7-14}$ alkoxyaryl, $C_{9-14}$ cycloalkoxyaryl, 5–7 membered heteroaryl or $C_{7-14}$ alkylheteroaryl; or $R_1$ and $R_2$, together with the nitrogen atom to which they are attached, join to form a 4–8 membered monocyclic heterocycle;

(b) m is 1 or 2;

(c) n is 1 or 2;

(d) $R_3$ is H; or $C_{1-6}$ alkyl, $C_{2-6}$ alkenyl or $C_{3-7}$ cycloalkyl, each optionally substituted with halogen;

(e) $R_4$ is $C_{1-8}$ alkyl optionally substituted with halo, cyano, amino, $C_{1-6}$ dialkylamino, $C_{6-10}$ aryl, $C_{7-14}$ alkylaryl, $C_{1-6}$ alkoxy, carboxy, hydroxy, aryloxy, $C_{7-14}$ alkylaryloxy, $C_{2-6}$ alkylester or $C_{8-15}$ alkylarylester; $C_{3-12}$ alkenyl; $C_{3-7}$ cycloalkyl or $C_{4-10}$ alkylcycloalkyl, wherein the cycloalkyl or alkylcycloalkyl are optionally substituted with hydroxy, $C_{1-6}$ alkyl, $C_{2-6}$ alkenyl or $C_{1-6}$ alkoxy; or $R_3$ together with the carbon atom to which it is attached forms a $C_{3-7}$ cycloalkyl group optionally substituted with $C_{2-6}$ alkenyl;

(f) Y is H, phenyl substituted with nitro, pyridyl substituted with nitro, or $C_{1-6}$ alkyl optionally substituted with cyano, hydroxyl or $C_{3-7}$ cycloalkyl; provided that if $R_5$ or $R_6$ is H then Y is H;

(g) B is H, $C_{1-6}$ alkyl, $R_5$—(C=O)—, $R_5O(C=O)$—, $R_5$—N($R_6$)—C(=O)—, $R_5$—N($R_6$)—C(=S)—, $R_5SO_2$—, or $R_5$—N($R_6$)—$SO_2$—;

(h) $R_5$ is (i) $C_{1-10}$ alkyl optionally substituted with phenyl, carboxyl, $C_{1-6}$ alkanoyl, 1–3 halogen, hydroxy, —OC(O)$C_{1-6}$ alkyl, $C_{1-6}$ alkoxy, amino optionally substituted with $C_{1-6}$ alkyl, amido, or (lower alkyl)amido; (ii) $C_{3-7}$ cycloalkyl, $C_{3-7}$ cycloalkoxy, or $C_{4-10}$ alkylcycloalkyl, each optionally substituted with hydroxy, carboxyl, ($C_{1-6}$ alkoxy)carbonyl, amino optionally substituted with $C_{1-6}$ alkyl, amido, or (lower alkyl)amido; (iii) $C_{6-10}$ aryl or $C_{7-16}$ arylalkyl, each optionally substituted with $C_{1-6}$ alkyl, halogen, nitro, hydroxy, amido, (lower alkyl)amido, or amino optionally substituted with $C_{1-6}$ alkyl; (iv) Het; (v) bicyclo(1.1.1)pentane; or (vi) —C(O)O$C_{1-6}$ alkyl, $C_{2-6}$ alkenyl or $C_{2-6}$ alkynyl;

(i) $R_6$ is H; $C_{1-6}$ alkyl optionally substituted with 1–3 halogens; or $C_{1-6}$ alkoxy provided $R_5$ is $C_{1-10}$ alkyl;

(j) X is O, S, SO, $SO_2$, $OCH_2$, $CH_2O$ or NH;

(k) R' is isoquinoline, $C_{6-10}$ aryl or $C_{7-14}$ alkylaryl, each optionally substituted with $R^a$; and (l) $R^a$ is $C_{1-6}$ alkyl, $C_{3-7}$ cycloalkyl, $C_{1-6}$ alkoxy, $C_{3-7}$ cycloalkoxy, halo-$C_{1-6}$ alkyl, $CF_3$, mono- or di-halo-$C_{1-6}$ alkoxy, cyano, halo, thioalkyl, hydroxy, alkanoyl, $NO_2$, SH, amino, $C_{1-6}$ alkylamino, di($C_{1-6}$)alkylamino, di($C_{1-6}$)alkylamide, carboxyl, ($C_{1-6}$)carboxyester, $C_{1-6}$ alkylsulfone, $C_{1-6}$ alkylsulfonamide, di($C_{1-6}$)alkyl(alkoxy)amine, $C_{6-10}$ aryl, $C_{7-14}$ alkylaryl, or a 5–7 membered monocyclic heterocycle;

or a pharmaceutically acceptable salt, solvate or prodrug thereof.

2. The compound of claim 1 wherein $R_1$ and $R_2$ are each independently $C_{1-8}$ alkyl, $C_{3-7}$ cycloalkyl, $C_{4-10}$ alkylcycloalkyl, $C_{1-6}$ alkoxy, $C_{6-10}$ aryl, $C_{7-14}$ alkylaryl, 5–7 membered heteroaryl or $C_{7-14}$ alkylheteroaryl; or $R_1$ and $R_2$, together with the nitrogen atom to which they are attached, join to form a 4–8 membered monocyclic heterocycle.

3. The compound of claim 2 wherein $R_1$ and $R_2$ are each independently $C_{1-8}$ alkyl, $C_{4-10}$ alkylcycloalkyl, $C_{1-6}$ alkoxy, $C_{6-10}$ aryl, $C_{7-14}$ alkylaryl, 5–7 membered heteroaryl or $C_{7-14}$ alkylheteroaryl, or $R_1$ and $R_2$, together with the nitrogen atom to which they are attached, join to form a 5–6 membered monocyclic heterocycle.

4. The compound of claim 1 wherein $R_3$ is $C_{1-6}$ alkyl, $C_{2-6}$ alkenyl or $C_{3-7}$ cycloalkyl.

5. The compound of claim 4 wherein $R_3$ is $C_{2-6}$ alkenyl.

6. The compound of claim 1 wherein $R_4$ is $C_{1-8}$ alkyl optionally substituted with $C_6$ aryl, $C_{1-6}$ alkoxy, carboxy, hydroxy, aryloxy, $C_{7-14}$ alkylaryloxy, $C_{2-6}$ alkylester or $C_{8-15}$ alkylarylester; $C_{3-12}$ alkenyl; $C_{3-7}$ cycloalkyl; or $C_{4-10}$ alkylcycloalkyl.

7. The compound of claim 6 wherein $R_4$ is $C_{1-8}$ alkyl optionally substituted with $C_{1-6}$ alkoxy; or $C_{3-7}$ cycloalkyl.

8. The compound of claim 1 wherein Y is H.

9. The compound of claim 1 wherein B is H, $C_{1-6}$ alkyl, $R_5$—(C=O)—, $R_5O(C=O)$—, $R_5$—N($R_6$)—C(=O)—, $R_5$—N($R_6$)—C(=S)—, $R_5SO_2$—, or $R_5$—N($R_6$)—$SO_2$—.

10. The compound of claim 9 wherein B is $R_5$—(C=O)—, $R_5O(C=O)$—, or $R_5$—N($R_6$)—C(=O)—.

11. The compound of claim 10 wherein B is $R_5O(C=O)$— and $R_5$ is $C_{1-6}$ alkyl.

12. The compound of claim 1 wherein $R_5$ is (i) $C_{1-10}$ alkyl optionally substituted with phenyl, carboxyl, $C_{1-6}$ alkanoyl, 1–3 halogen, hydroxy, $C_{1-6}$ alkoxy; (ii) $C_{3-7}$ cycloalkyl, $C_{3-7}$ cycloalkoxy, or $C_{4-10}$ alkylcycloalklyl; or (iii) $C_{6-10}$ aryl or $C_{7-16}$ arylalkyl, each optionally substituted with $C_{1-6}$ alkyl or halogen.

13. The compound of claim 12 wherein $R_5$ is (i) $C_{1-10}$ alkyl optionally substituted with 1–3 halogen or $C_{1-6}$ alkoxy; or (ii) $C_{3-7}$ cycloalkyl or $C_{4-10}$ alkylcycloalkyl.

14. The compound of claim 1 wherein $R_6$ is H or $C_{1-6}$ alkyl optionally substituted with 1–3 halogens.

15. The compound of claim 14 wherein $R_6$ is H.

16. The compound of claim 1 wherein X is O or NH.

17. The compound of claim 1 wherein R' is isoquinoline; or $C_{6-10}$ aryl optionally substituted with $R^a$.

18. The compound of claim 17 wherein R' is isoquinoline.

19. The compound of claim 18 wherein the heterocycle is substituted with at least one of $C_{1-6}$ alkyl, $C_{1-6}$ alkoxy, halo, $C_{1-6}$ aryl, $C_{7-14}$ alkylaryl, or a 5–7 membered monocyclic heterocycle.

20. The compound of claim 1 wherein $R^a$ is $C_{1-6}$ alkyl, $C_{3-7}$ cycloalkyl, $C_{1-6}$ alkoxy, halo-$C_{1-6}$ alkyl, halo, amino, $C_6$ aryl, or a 5–7 membered monocyclic heterocycle.

21. A compound having the formula

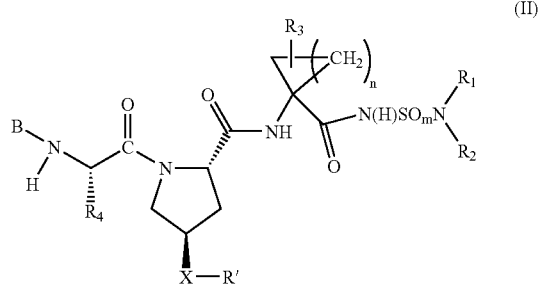

wherein:

(a) $R_1$ and $R_2$ are each independently $C_{1-8}$ alkyl, $C_{3-7}$ cycloalkyl, $C_{4-10}$ alkylcycloalkyl, $C_{1-6}$ alkoxy, $C_{6-10}$ aryl, $C_{7-14}$ alkylaryl, 5–7 membered heteroaryl or $C_{7-14}$ alkylheteroaryl; or $R_1$ and $R_2$, together with the nitrogen atom to which they are attached, join to form a 4–8 membered monocyclic heterocycle;

(b) m is 1 or 2;

(c) n is 1 or 2;

(b) $R_3$ is $C_{1-6}$ alkyl, $C_{2-6}$ alkenyl or $C_{3-7}$ cycloalkyl;

(c) $R_4$ is $C_{1-8}$ alkyl optionally substituted with $C_6$ aryl, $C_{1-6}$ alkoxy, carboxy, hydroxy, aryloxy, $C_{7-14}$ alkylaryloxy, $C_{2-6}$ alkylester, $C_{8-15}$ alkylarylester; $C_{3-12}$ alkenyl; $C_{3-7}$ cycloalkyl; or $C_{4-10}$ alkylcycloalkyl;

(d) B is H, $C_{1-6}$ alkyl, $R_5$—(C=O)—, $R_5O$(C=O)—, $R_5$—N($R_6$)—C(=O)—, $R_5$—N($R_6$)—C(=S)—, $R_5SO_2$—, or $R_5$—N($R_6$)—$SO_2$—;

(e) $R_5$ is (i) $C_{1-10}$ alkyl optionally substituted with phenyl, carboxyl, $C_{1-6}$ alkanoyl, 1–3 halogen, hydroxy, $C_{1-6}$ alkoxy; (ii) $C_{3-7}$ cycloalkyl, $C_{3-7}$ cycloalkoxy, or $C_{4-10}$ alkylcycloalklyl; or (iii) $C_{6-10}$ aryl or $C_{7-16}$ arylalkyl, each optionally substituted with $C_{1-6}$ alkyl or halogen;

(f) $R_6$ is H or $C_{1-6}$ alkyl optionally substituted with 1–3 halogens;

(g) X is O or NH;

(h) R' is isoquinoline; or $C_{6-10}$ aryl optionally substituted with $R^a$; and (i) $R^a$ is $C_{1-6}$ alkyl, $C_{3-7}$ cycloalkyl, $C_{1-6}$ alkoxy, halo-$C_{1-6}$ alkyl, halo, amino, $C_6$ aryl, or a 5–7 membered monocyclic heterocycle;

or a pharmaceutically acceptable salt, solvate or prodrug thereof.

22. The compound of claim 21 wherein $R_1$ and $R_2$ are each independently $C_{1-8}$ alkyl, $C_{4-10}$ alkylcycloalkyl, $C_{1-6}$ alkoxy, $C_{6-10}$ aryl, $C_{7-14}$ alkylaryl, 5–7 membered heteroaryl, $C_{7-14}$ alkylheteroaryl; or $R_1$ and $R_2$, together with the nitrogen atom to which they are attached, join to form a 5–6 membered monocyclic heterocycle.

23. The compound of claim 22 wherein $R_1$ and $R_2$ are each independently $C_{1-3}$ alkyl or $C_{1-3}$ alkoxy.

24. The compound of claim 21 wherein R' is isoquinoline which is substituted with methoxy and at least one of a $C_6$ aryl and a 5–7 membered monocyclic heterocycle.

25. A compound having the formula

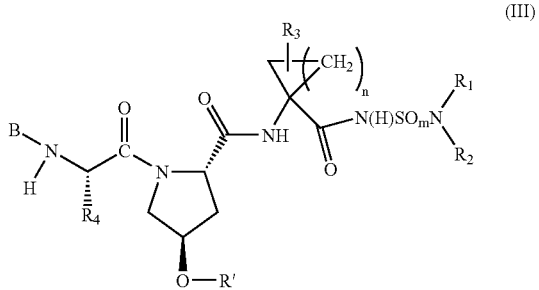

(III)

wherein:

(a) $R_1$ and $R_2$ are each independently $C_{1-8}$ alkyl, $C_{4-10}$ alkylcycloalkyl, $C_{1-6}$ alkoxy, $C_{6-10}$ aryl, $C_{7-14}$ alkylaryl, 5–7 membered heteroaryl or $C_{7-14}$ alkylheteroaryl; or $R_1$ and $R_2$, together with the nitrogen atom to which they are attached, join to form a 5–6 membered monocyclic heterocycle;

(b) m is 1 or 2;

(c) n is 1 or 2;

(d) $R_3$ is $C_{2-6}$ alkenyl;

(e) $R_4$ is $C_{1-8}$ alkyl;

(f) B is $R_5O$(C=O)—, or $R_5$—NH—C(=O)—;

(g) $R_5$ is $C_{1-10}$ alkyl;

(h) R' is isoquinoline optionally substituted with $R^a$; and (i) $R^a$ is $C_{1-6}$ alkyl, $C_{1-6}$ alkoxy, halo, $C_6$ aryl, or a 5–7 membered monocyclic heterocycle;

or a pharmaceutically acceptable salt, solvate or prodrug thereof.

26. The compound of claim 25 wherein $R_1$ and $R_2$ are each independently $C_{1-3}$ alkyl or $C_{1-3}$ alkoxy.

27. The compound of claim 26 wherein $R_1$ is methyl.

28. The compound of claim 26 wherein $R_2$ is methyl or methoxy.

29. The compound of claim 25 wherein $R_3$ is vinyl.

30. The compound of claim 25 wherein $R_4$ is t-butyl.

31. The compound of claim 25 wherein $R_5$ is t-butyl.

32. The compound of claim 25 wherein R' is isoquinoline optionally substituted with $R^a$.

33. The compound of claim 25 wherein $R_1$ is methyl, $R_2$ is methoxy, $R_3$ is vinyl, $R_4$ is t-butyl, $R_5$ is t-butyl, and R' is isoquinoline substituted with at least one $R^a$.

34. The compound of claim 33 wherein $R^a$ is $C_{1-6}$ alkoxy.

35. The compound of claim 34 wherein $R^a$ further includes at least one of $C_6$ aryl or a 5–7 membered monocyclic heterocycle.

36. A composition comprising the compound of claim 1 and a pharmaceutically acceptable carrier.

37. The composition according to claim 36 further comprising another compound having anti-HCV activity.

38. The composition according to claim 37 wherein the other compound having anti-HCV activity is an interferon.

39. The composition according to claim 38 wherein the interferon is selected from the group consisting of interferon alpha 2B, pegylated interferon alpha, consensus interferon, interferon alpha 2A and lymphoblastiod interferon tau.

40. The composition according to claim 37 wherein the other compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

41. The composition according to the claim 36 further comprising an interferon and ribavirin.

42. A method of inhibiting the functioning of the HCV serine protease comprising contacting the protease with the compound of claim 1.

43. A method of treating an HCV infection in a patient, comprising administering to the patient a therapeutically effective amount of the compound of claim 1, or a pharmaceutically acceptable solvate, prodrug or salt thereof.

44. The method according to claim 43 wherein the compound is effective to inhibit the functioning of the HCV serine protease.

45. The method according to claim 43 further comprising administering another compound having anti-HCV activity prior to, after or simultaneously with the compound of claim 1.

46. The method according to claim 45 wherein the other compound having anti-HCV activity is an interferon.

47. The method according to claim 46 wherein the interferon is selected from the group consisting of interferon alpha 2B, pegylated interferon alpha, consensus interferon, interferon alpha 2A, lymphoblastiod interferon tau.

48. The method according to claim 45 wherein the other compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

49. The method according to claim 45 wherein the other compound having anti-HCV activity is a small molecule.

50. The method according to claim 49 wherein the compound having anti-HCV activity is effective to inhibit the functioning of a target selected from the group consisting of HCV metalloprotease, HCV serine protease, HCV polymerase, HCV helicase, HCV NS4B protein, HCV entry, HCV assembly, HCV egress, HCV NS5A protein, IMPDH and a nucleoside of HCV.

51. The method according to claim 49 wherein the other compound having anti-HCV activity is effective to inhibit the functioning of target in the HCV life cycle other than HCV serine protease.

* * * * *